(12) United States Patent
Lippard et al.

(10) Patent No.: US 7,399,639 B2
(45) Date of Patent: Jul. 15, 2008

(54) SENSORS, AND METHODS OF MAKING AND USING THE SAME

(75) Inventors: Stephen J. Lippard, Cambridge, MA (US); Carolyn Crystal Woodroofe, Cambridge, MA (US)

(73) Assignee: Massachusetts Institute of Technology, Cambridge, MA (US)

(*) Notice: Subject to any disclaimer, the term of this patent is extended or adjusted under 35 U.S.C. 154(b) by 616 days.

(21) Appl. No.: 10/429,898

(22) Filed: May 4, 2003

(65) Prior Publication Data

US 2004/0224420 A1 Nov. 11, 2004

(51) Int. Cl.
*G01N 33/20* (2006.01)
*C07D 311/88* (2006.01)
*C07D 405/14* (2006.01)

(52) U.S. Cl. .................... 436/81; 422/61; 436/73; 436/74; 436/79; 436/80; 436/82; 436/83; 436/84; 436/166; 436/169; 436/172; 546/256; 549/223; 549/227; 549/226

(58) Field of Classification Search .......... 422/61; 436/73–74, 79–84, 166, 169, 172; 546/256; 549/223, 225–227
See application file for complete search history.

(56) References Cited

U.S. PATENT DOCUMENTS

| | | | | |
|---|---|---|---|---|
| 4,476,229 A * | 10/1984 | Fino et al. | ................... | 436/500 |
| 4,510,251 A | 4/1985 | Kirkemo et al. | ............. | 436/536 |
| 4,614,823 A | 9/1986 | Kikermo et al. | ............. | 544/300 |
| 5,346,670 A | 9/1994 | Renzoni et al. | ............... | 422/52 |
| 5,453,220 A | 9/1995 | Swager et al. | ............... | 252/582 |
| 5,721,365 A | 2/1998 | Keefer et al. | ................ | 544/382 |
| 5,723,304 A * | 3/1998 | Abuknesha | ................ | 435/7.9 |
| 5,741,657 A * | 4/1998 | Tsien et al. | ................... | 435/18 |
| 5,756,771 A | 5/1998 | Mattingly | ................... | 549/223 |
| 5,986,094 A | 11/1999 | Ghoshal et al. | ............. | 544/230 |
| 6,013,802 A | 1/2000 | Hoyland et al. | ............... | 546/18 |
| 6,051,207 A | 4/2000 | Klaveness et al. | ............. | 424/9.1 |
| 6,063,637 A | 5/2000 | Arnold et al. | ................. | 436/94 |
| 6,221,604 B1 * | 4/2001 | Upadhya et al. | ............... | 435/6 |
| 6,323,309 B1 | 11/2001 | Swager et al. | ............... | 528/380 |
| 7,018,840 B2 * | 3/2006 | Lippard et al. | ................ | 436/73 |
| 2002/0106697 A1 | 8/2002 | Lippard et al. | ............... | 435/7.2 |
| 2003/0008405 A1 | 1/2003 | Lippard et al. | ................ | 436/73 |
| 2003/0178607 A1 | 9/2003 | Swager et al. | ............... | 252/582 |
| 2004/0229300 A1 * | 11/2004 | Frederickson | ............. | 435/7.23 |
| 2005/0112769 A1 * | 5/2005 | Lippard et al. | ................ | 436/81 |

FOREIGN PATENT DOCUMENTS

EP    0 201 751 A2    11/1986

(Continued)

OTHER PUBLICATIONS

Yaron, A. et al, Analytical Biochemistry 1979, 95, 228-235.*

(Continued)

*Primary Examiner*—Arlen Soderquist
(74) *Attorney, Agent, or Firm*—Dana M. Gordon; Foley Hoag LLP

(57) ABSTRACT

The present invention is directed, in part, to sensors for detecting metal ions, and methods of making and using the same.

32 Claims, 27 Drawing Sheets

FOREIGN PATENT DOCUMENTS

| EP | 0 297 303 A2 | | 1/1989 |
|---|---|---|---|
| WO | 02/04562 | * | 1/2002 |

OTHER PUBLICATIONS

Tsien, R.Y. et al, Journal of Cell Biology 1982, 94, 325-334.*
Zavoico, G. B. et al, Journal of Biological Chemistry 1988, 263, 9635-9639.*
Essig-Marcello, J. S. et al, In Vitro Toxicology 1989, 2, 311-324.*
Homolya, L. et al, Journal of Biological Chemistry 1993, 268, 21493-21496.*
Bueb, J.-L. et al, Biochimica et Biophysica Acta, General Subjects 1995, 1244, 79-84.*
Cabantchik, Z. I. et al, Analytical Biochemistry 1996, 233, 221-227.*
DeBernardi, M. A. et al, Proceedings of the National Academy of Sciences of the United States of America 1996, 93, 4577-4582.*
Miyawaki, A. et al, Nature 1997, 338, 882-887.*
Hyrc, K. L. et al, Cell Calcium 1998, 24, 165-175.*
Tombal, B. et al, Cell Calcium 1999, 25, 19-28.*
Berregi, I. et al, Analytical Letters 2000, 33, 277-295.*
Sumner, J. P. et al, Analyst 2002, 127, 11-16.*
Takakusa, H. et al, Journal of the American Chemical Society 2002, 124 1653-1657.*
Gee, K. R. et al, Cell Calcium 2002, 31, 245-251.*
Dias, N. et al, Research in Microbiology 2002, 153, 313-322.*
Hirano, T. et al, Journal of the American Chemical Society 2002, 124, 6555-6562.*
Rizzo, J. et al, Molecular and Cellular Probes 2002, 16, 277-283.*
Dineley, K. E. et al, Molecular Pharmacology 2002, 62, 618-627.*
Falck, J. R. et al, Journal of the American Chemical Society 1981, 103, 7396-7398.*
Shechter, E. et al, FEBS Letters 1982, 139, 121-124.*
Grimes, P. A. et al, Archives of Ophthalmology 1982, 100, 635-639.*
Babcock, D. F., Journal of Biological Chemistry 1983, 258, 6380-6389.*
Araie, M., Experimental Eye Research 1986, 42, 141-150.*
O'Connor, S. et al, In Vitro Toxicology 1991, 4, 197-206.*
Harrison, R. A. P. et al, Molecular Reproduction and Development 1993, 35, 197-208.*
Novak, E. J. et al, Cytometry 1994, 17, 135-141.*
Spencer, C. I. et al, Pfluegers Archiv-European Journal of Physiology 1995, 430, 579-583.*
Cole, L. et al, Protoplasma 1997, 199, 18-29.*
Bracey, D. et al, Journal of Microbiological Methods 1998, 31, 113-125.*
Gultneh, Y. et al, Journal of Inorganic Biochemistry 1999, 75, 7-18.*
Ohtsu, H. et al, Journal of the American Chemical Society 2000, 122), 5733-5741.*
Kawanishi, Y. et al, Angewandte Chemie, International Edition 2000, 39, 3438-3440.*
Blattner, J. R. et al, Analytical biochemistry 2001, 295, 220-226.*
Kuchitsu, K. et al, New Phytologist 2002, 153, 527-533.*
Xu, H. et al, Analyst 2002, 127, 1471-1477.*
Atar, D. et al., "Excitation-Transcription Coupling Mediated by Zinc Influx Through Voltage-dependent Calcium Channels", J. Biol. Chem 1995, 270:2473-2477.
Bergonzi et al.; "Molecular Switches of Fluorescence Operating Through Metal Centred Redox Couples", Coord. Chem. Rev. 170: 31-46 (1998).
Buchen et al.; "Copper Complexes of a p-phenylenediamine-based bis (tridentate) Ligand", J. Chem. Soc. Dalton Trans. pp. 2697-2703, (1997).
Budde, T. et al., "Imaging Free Zinc in Synaptic Terminals in Live Hippocampal Slices", Neuroscience 1997, 79, 347-358.
Burdette, S. C. et al., "Fluorescent Sensors for $Zn^{+2}$ Based on a Fluorescein Platform: Synthesis, Properties and Intracellular Distribution", J. Am. Chem Soc., 2001, 123, 7831-7841.
Burdette, S. C., "Investigation of Zinc Metalloneurochemistry with Fluorescent Sensors Based on Fluorescein Platforms", Ph.D. Thesis, MIT, Oct. 2002.

Burdette, S. C. et al.; "The Rhodafluor Family. An Initial Study of Potential Ratiometric Fluorescent Sensors for $Zn^{2+}$", Inorg. Chem. 2002, 41, 6816-6823.
Burton, H., et al., "Fluorescein Dyes Derived from 2-Methylresorcinol", J. Soc. Chem. Ind. London 1948: 67: 345-347.
Canzoniero, L. M. T. et al., "Measurement of Intracellular Free Zinc in Living Neurons", Neurobiology of Disease 1997, 4, 275-279.
Chenier et al.; "Chiral Tropocoronands: Synthesis and Metal Complex Formation," Tetrahedron Lett., 38:7341-7344 (1997).
Czarnick, A. W., "Desperately Seeking Sensors", Curr. Biol 1995, 2: 423-428.
Da Mota, M. M. et al., "The Co-ordination Number of Transition-Metal Ions. Part VII: An Evaluation of Steric Factors in the Stabilisation of High-spin Five-co-ordinate Nickel (II) Complexes of Multidendate α-Pyridyl Ligands", J. Chem. Soc. (A) 1969, 2036-2042.
De Silva, A. P. et al., "Signaling Recognition Events with Fluorescent Sensors and Switches", Chem. Rev. 1997, 97: 1515-1566.
Fabbrizzi et al.; "Controllable Intramolecular Motions That Generate Fluorescent Signals for a Metal Scorpionate Complex", Angew. Chem. Int. Ed. 37(6): 800-802, (1998).
Fabbrizzi et al.; "Transition Metals as Switches", Acc. Chem. Res. 32:846-853, (1999).
Fahrni, C. J. et al., "Aqueous Coordination Chemistry and Quinoline-Based Fluorescence Probes for the Biological Chemistry of Zinc", J. Am. Chem. Soc. 1999, 121: 11448-11458.
Frederickson, C. J., et al., "A quinoline fluorescence method for visualizing and assaying the histochemically reactive zinc (bouton zinc) in the brain", J. Neurosci. Meth. 1987, 20, 91-103.
Frederickson, C. J., "Neurobiology of Zinc and Zinc-Containing Neurons", Int. Rev. Neurobiol., 1989, 31: 145-238.
Godwin, H. A., et al., "A Fluorescent Zinc Probe Based on Metal-Induced Peptide Folding", J. Am. Chem. Soc. 1996, 118: B16514-6515.
Goral, Vasiliy et al., "Double-level "orthogonal" dynamic combinatorial libraries on transition metal template", Proceedings of the National Academy of Sciences, vol. 98, No. 4, pp. 1347-1352 (2001).
Gruenwedel, D. W., "Multidentate Coordination Compounds. Chelating Properties of Aliphatic Amines Containing α-Pyridyl Residues and Other Aromatic Ring Systems as Donor Groups", Inorg. Chem. 1968, 7: 495-501.
Harrison, N. L., et al., "$Zn^{2+}$: an Endogenous Modulator of Ligand- and Voltage-gated Ion Channels", Neuropharmacology 1994, 33: 935-952.
Hirano, T., et al., "Highly Zinc-Selective Fluorescent Sensor Molecules Suitable for Biological Applications", J. Am. Chem. Soc. 2000, 122: 12399-12400.
Huang, E. P., "Metal Ions and Synaptic Transmission: Think Zinc", Proc. Natl. Acad. Sci. Dec. 1997, 94: 13386-13387.
Maruyama, S. et al., "A Novel, Cell-Permeable, Fluorescent Probe for Ratiometric Imaging of Zinc Ion", J. Am. Chem. Soc. 2002, 124: 10650-10651.
Koike et al., "A Novel Biomimetic Zinc(II)-Fluorophore, Dansylamidoethyl-Pendant Macrocyclic Tetraamine 1,4,7,10-Tetraazacyclododecane (Cyclen)", J. Am. Chem. Soc. 118: 12696-12703 (1996).
Koike et al.; "The First Anionic Sulfonamide-Binding Zinc (II) Complexes with a Macrocyclic Triamine: Chemical Verification of the Sulfonamide Inhibition of Carbonic Anhydrase", J. Am. Chem. Soc. 114:7338-7345 (1992).
Kovacs, Z. et a., "A General Synthesis of Mono- and Disubstituted 1,4,7-Triazacycloonoanes", Tet. Lett. 1995, 51: 9269-9272.
Mahadevan, I. B. et al., "The Synthesis of Zinquin Ester and Zinquin Acid, Zinc(II)-Specific Fluorescing Agents for Use in the Study of Biological Zinc (II)", Aust. J. Chem. 1996, 49: 561-568.
McBryde, W. A. E., "Spectrophotometric Determination of Equilibrium Constants in Solution", Talanta, 21: 979-1004 (1974).
Minta et al.; "Fluorescent Indicators for Cytosolic Calcium Based on Rhodamine and Fluorescein Chromophores", the Journal of Biological Chemistry, 264(14): 8171-8178 (May 15, 1989).

Mizukami, S. et al., "Imaging of caspase-3 activation in HeLa cells stimualted with etoposide using a novel fluorescent probe", FEBS Lett 1999, 453: 356-60.

Nasir, M. S. et al., "The chemical cell biology of zinc: structure and intracellular fluorescence of a zinc-quinolinesulfonamide complex", JBIC 1999, 4: 775-783.

Packard, B. Z. et al., "Characterization of fluorescence quenching in bifluorophoric protease substrates", *Biophys. Chem.*, 67:167-176 (1997).

Packard, B. Z. et al., "Profluorescent protease substrates: Intramolecular dimers described by the exciton model", *Proc. Natl. Acad. Sci. USA* 93:11640-11645 (1996).

Palmiter, R. D. et al., "ZnT-2, a mammalian protein that confers resistance to zinc by facilitating vesicular sequestration", EMBO J. 1996, 15: 1874-1791.

Palmiter, R. D. et al., "ZnT-3, a putative transporter of zinc into synapse vesicles", Proc. Natl. Acad. Sci. USA 1996, 93: 14934-14939.

Pfeiffer et al.; "Nitric Oxide: Chemical Puzzles Posed by a Biological Messenger", Angew. Chem. Int. Ed. 38: 1714-1731, (1999).

Prasad, J. S., et al., "Synthesis of Gadolinium (±)-10-(I-Hydroxypropan-2-yl)-1,4,7,10-tetraazacyclododecane-1,4,7-triyltriacetate *via* Tribenzyl 1,4,7,10-Tetraazacyclododecane-1,4,7-tricarboxylate", J. Chem. Soc. Perkin Trans. 1991, 3329-3332.

Romary, J. K. et al., "New 2-Pyridyl Polyamines. Synthesis, Spectra, and Proton Dissociation Constants", J. Chem. Soc. (C) 1968, 2884-2887.

Sen, R. N. et al., "Aldehydofluorescein and Dyes Derived from it", J. Indian Chem. Soc. 1929, 6: 505-516.

Sen, R. N. et al., "Aldehydo-phenolphthalien and Dyes derived from it", J. Indian Chem. Soc. 1929, 6: 53-63.

Shaughnessy et al.; "A Fluorescence-Based Assay for High-Throughput Screening of Coupling Reactions. Application to Heck Chemistry", J. Am. Chem. Soc. 121: 2123-2132, (1999).

Smith et al.; "The Design and Properties of a Series of Calcium Indicators Which Shift from Rhodamine-like to Fluorescein-like Fluorescence on Binding Calcium", J. Chem. Soc. Perkin Trans. 2, pp. 1195-1204, (1993).

Sumner, J. P. et al., "A Fluroescent Pebble Nanosensor for Intracellular Free Zinc", Analyst 2002, 127: 11-16.

Takakusa, H. et al., "A Novel Design Method of Rationmetric Fluorescent Probes Based on Fluorescence Resonance Energy Transfer Switching by Spectral Overlap Integral", Che. Eur. J. 2003, 9(7): 1479-1485.

Takakusa, H. et al., "Intramolecular Fluorescence Resonance Energy Transfer System with Coumarin Donor Included in β-Cyclodextrin", Anal. Chem. 2001, 73(5): 939-942.

Tanaka, M. et al., "Synthesis and Metal-Ion Binding Properties of Monoazathiacrown Ethers", J. Org. Chem. 2001, 66: 7008-7012.

Thompson, R. B. et al., "Expanded Dynamic Range of Free Zind Ion Determination by Flourescence Anisotropy", Anal. Chem. 1998, 70: 1749-1754.

Thompson, R. B. et al., "Fluorescence microscopy of stimulated Zn(II) release from organotypic cultures of mammalian hippocampus using a carbonic anhydrase-based biosensor system", J. Neuro. Meth. 2000, 96: 35-45.

Tsien, R. Y.; "Fluorescent Probes of Cell Signaling", Ann. Rev. Neurosci., 12:227-253, (1989).

Tsien, R. Y., "Fluorescent and Photochemical Probes of Dynamic Biochemical Signals inside Living Cells", *Am. Chem. Soc.*, 130-146 (1993).

Tsien, R. Y.; "New Calcium Indicators and Buffers with High Selectivity Against Magnesium and Protons: Design, Synthesis, and Properties of Prototype Structures", Biochemistry 19: 2396-2404, (1980).

Uhlig and Döring "Zum Verhalten von Cobalt(II und Eisen (III) bei der Flüssig-Flüssig-Extraction mit Pyridylsubstituierten Benzensulfon-amiden", Z. Anorg. Allg. Chem., 492:52-62, (1982).

Valeur, B. et al., "Tuning of Photoinduced Energy Transfer in a Bichromophoric Coumarin Supermolecule by Cation Binding", J. Phys. Chem. 1992,96: 6545-6549.

von Anderegg et al.; "14. Pyridinderivate als Komplexbildner. XI[1]. Die Thermodynamik der Metallkomplexbildung mit Bis-, Tris- und Tetrakis[(2-pyridyl)methyl]-aminen", Helvetica Chimica Acta, 60: 123-140, (1977).

Walkup, G. K. et al., "A New Cell-Permeable Fluorescent Probe for $Zn^{2+}$", J. Am. Chem. Soc. 2000, 122: 5644-5645.

Walkup, G. K. et al., "Fluorescent Chemosensors for Divalent Zinc Based on Zinc Finger Domains. Enhanced Oxidative Stability, Metal Binding Affinity, and Structural and Functional Characterization", J. Am. Chem. Soc. 1977, 119: 3443-3450.

Walkup, G. K. et al., "Stereoselective Synthesis of Fluorescent α-Amino Acids Containing Oxine (8-Hydroxyquinoline) and Their Peptide Incorporation in Chemosensors for Divalent Zinc", J. Org. Chem. 1998, 63: 6727-6731.

Wang, Fen et al., "Tuning of Binding Selectivity: Metal Control of Organic Guest Binding and Allosteric Perturbation of a Fluorescent Metal Sensor", *J. Org. Chem.*, vol. 64, pp. 8922-8928 (1999).

Zalewski, P. D. et al., "Correlation of apoptosis with change in intracellular labile Zn(II) using Zinquin [(2-methyl-8-ρ-Toluenesulphonadmido-6-quinolyloxy)acetic acid], a new specific fluorescent probe for Zn(II)", Biochem. J. 1993, 296: 403-408.

Zask et al.; "Syntheses and Spectral Properties of Tropocoronands, a New Class of Versatile Metal-Complexing Macrocycles Derived from Aminotropone Imines", Inorg. Chem. 25: 3400-3407, (1986).

Zlokarnik, G. et al., "Quantitation of Transcription and Clonal Selection of Single Living Cells with β-Lactamase as Reporter", Sicence 1998, 279: 84-88.

* cited by examiner

Formula 1

A

B

X = CO₂H, Y = H  Formula 100
X = H, Y = CO₂H  Formula 101

W = CO₂Et, Z = H  Formula 102
W = H, Z = CO₂Et  Formula 103

No Zn

+ Zn

Formula 1  Formula 103  Formula 101

No Zn

+ Zn

Formula 1        Formula 102        Formula 100

Formula 104 (ZnpyrA-1)

Formula 105

SENSORS, AND METHODS OF MAKING AND USING THE SAME

1. GOVERNMENT SUPPORT

The subject invention was made in part with support from the U.S. Government. Accordingly, the U.S. Government has certain rights in this invention.

2. INTRODUCTION

Fluorescent Sensors

Fluorescence technology has revolutionized cell biology and many areas of biochemistry. In certain instances, fluorescent molecules may be used to trace molecular and physiological events in living cells. Certain sensitive and quantitative fluorescence detection devices have made fluorescence measurements an ideal readout for in vitro biochemical assays. In addition fluorescence measurement systems may be useful for determining the presence of analytes in environmental samples. Finally, because certain fluorescence detection systems are rapid and reproducible, fluorescence measurements are often used in high-throughput screening applications. The feasibility of using fluorescence technology for a particular application is often limited by the availability of an appropriate fluorescent sensor.

Zinc in Biological Systems

The importance of metals in biological systems and the general difficulty in measuring metals in living cells makes metal detection a particularly desirable field for the use of fluorescence technology. As one example, zinc is a vital component in many cellular processes. Although the traditional study of the bioinorganic chemistry of $Zn^{2+}$ has focused on structural and enzymatic functions in proteins, the neurobiology of $Zn^{2+}$ has been gaining attention. Whereas most $Zn^{2+}$ in biological systems is tightly bound in proteins and enzymes, a pool of free $Zn^{2+}$ has been imaged in cells. Sub-nanomolar concentrations of $Zn^{2+}$ have been detected in undifferentiated mammalian cells, and higher concentrations, approaching 300 μM, have been imaged in the mossy fiber terminals of the hippocampus. The $Zn^{2+}$ ion has the ability to modulate a variety of ion channels, may play a role in neuronal death during seizures, is pertinent to neurodegenerative disorders, and may be vital to neurotransmission and long-term potentiation.

Although $Zn^{2+}$ is critical to cellular processes, excess zinc ions may be toxic. The levels of $Zn^{2+}$ in the brain and other parts of the body are believed to be regulated by three related $Zn^{2+}$ transport proteins (ZnT-1, ZnT-2, and ZnT-3) and by metallothioneins (MTs), including MT-III and MT-IV which are expressed mainly in the brain. ZnTs and MTs are probably responsible for distributing the required $Zn^{2+}$ to proteins and enzymes, and minimizing the amounts of free $Zn^{2+}$ present in cells. In nerve cells, however, free $Zn^{2+}$ is available for neurological functions because $Zn^{2+}$ can be released from synaptic vesicles and can enter cells through voltage-dependent $Ca^{2+}$ channels. Despite the abundance of research, many aspects of ionic $Zn^{2+}$ in neurobiology remain unclear due to the limited detection methods currently available.

Because metal ion levels may be critical to normal cellular function, a number of diseases may result from, or may be caused by, errors in metabolism of a particular metal ion in the affected individual. For example, abnormal zinc metabolism has been found in some Alzheimer's patients, and low levels of zinc are associated with various behavioral disorders. Diagnosis of errors in such metal ion metabolism may be facilitated by the subject invention.

In part, the present invention is directed to fluorescent sensors for metal ions, and methods of making and using the same.

3. SUMMARY OF THE INVENTION

In part, the present invention is directed to compounds and methods of making and using the same that have (a) a first fluorophore comprising a Lewis base capable of forming a coordination bond with a metal ion, wherein one or more fluorescence properties of the first fluorophore changes upon coordination of the Lewis base to a metal ion; (b) a second fluorophore; and (c) a cleavable linker covalently linking the first fluorophore and the second fluorophore. Such a subject compound may used in certain embodiments for in vivo diagnosis.

As shown in FIG. 17 for one embodiment of the present invention, a subject compound may used to detect and optionally quantify the concentration of a metal ion. Without intending to limit the invention in any way, it is believed that in the embodiment presented in FIG. 17, a subject compound will permeate a cell, whereupon cleavage of the cleavable linker contained in the subject compound by a naturally occurring biological activity will give rise to two compounds containing fluorophores, one of which may be used to detect a metal ion and the other of which may be used as a standard to optionally quantify the concentration of the metal ion by measuring their fluorescence. It may be the case that the cleavage event "traps" the two fluorophores in the cell, because they are no longer able to permeate the cell membrane to any significant extent. In certain embodiments, the metal of interest is $Zn^{2+}$.

The subject compounds, and methods of making and using the same, may achieve a number of desirable results and features, one or more of which (if any) may be present in any particular embodiment of the present invention: (i) a subject compound may bind metal ions with a concomitant change in the fluorescence properties of a fluorophore contained in the compound; (ii) a subject compound may selectively bind a metal ion; (iii) a subject compound may have a $K_d$ near the median concentration of the metal ion under investigation allowing for the concentration of the metal ion in a sample or a patient to be determined; (iv) a subject compound may contain a fluorophore that exhibits an increased quantum yield, a change in emission wavelength or increased brightness among other changes in fluorescence properties upon coordinating a metal ion; (v) excitation wavelengths for a subject compound may exceed 340 nm and emission wavelengths may approach 500 nm; (vi) a subject compound may be capable of in vivo use; and without limitation, (vii) a subject compound may be irreversibly loaded into cells.

In part, the present invention is directed towards fluorophores including a Lewis base that is capable of coordinating to a metal ion. On occasion, the fluorophore is a fluorescein-based ligand or a derivative or analog of fluorescein. In certain aspects, the present invention is directed to improved fluorescence characteristics obtained for fluorescein-based ligands.

In one aspect, a subject compound includes a fluorophore comprising a Lewis base capable of forming a coordination bond with a metal ion, wherein one or more fluorescence properties of the fluorophore changes upon coordination of the Lewis base to a metal ion, and a cleavable chemical moiety.

In one aspect, the present invention is directed to a compound comprising a first fluorophore, a second fluorophore and a cleavable linker covalently linking the first fluorophore and the second fluorophore, wherein the fluorescence of the first and second fluorophores are substantially quenched by one another before the cleavable linker is cleaved, and wherein the first fluorophore is represented by the following generalized structure:

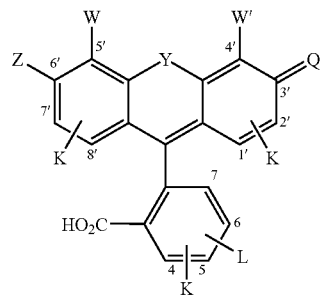

or a tautomer of the generalized structure, wherein, independently for each occurrence:

Y is O, S, Se, NR, or $C(CH_3)_3$, wherein R is an alkyl and R and the methyl groups of $C(CH_3)_2$ are optionally substituted with one or more K's;

Q is O, S or Se;

Z is QH, QU' wherein U' is a hydroxyl-protecting group, or V;

W and W' are each independently hydrogen, K or V;

K is optionally one or more substituents of the indicated moiety other than hydrogen that do not preclude the first fluorophore from fluorescing;

L is the cleavable linker covalently bonded to either the 5 or 6 position of the indicated aromatic ring; and V is a chemical moiety comprising a first Lewis base capable of coordinating to a metal ion, provided that when V occurs in Z and there is an oxygen atom directly bonded to the 6' carbon of the indicated aromatic ring, the Lewis base in V is not that oxygen atom, and wherein one or more fluorescence properties of the first fluorophore change measurably upon coordination of the first Lewis base to a metal ion.

In certain embodiments, the Lewis base contained in V may involve one of the structures depicted in FIGS. 1A and 1B In certain embodiments, the second fluorophore is coumarin or a derivative or analog thereof.

In another aspect, the present invention is directed to a compound comprising (a) a first fluorophore comprising at least one Lewis base capable of forming a coordination bond with a metal ion, wherein one or more fluorescence properties of the first fluorophore changes upon coordination of said Lewis base to a metal ion; (b) a second fluorophore; (c) a cleavable linker covalently linking the first fluorophore and the second fluorophore, wherein the cleavable linker is intended to be cleaved during use of the compound; and (d) the fluorescence of the first and second fluorophores are substantially quenched by one another before the cleavable linker is cleaved.

In another aspect, a subject compound may be represented by the following generalized structure:

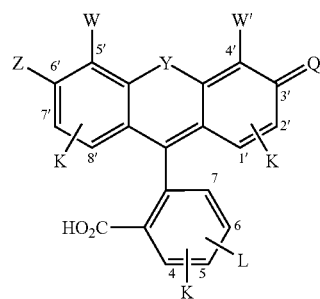

or a tautomer of the generalized structure, wherein, independently for each occurrence:

Y is O, S, Se, NR, or $C(CH_3)_3$, wherein R is an alkyl and R and the methyl groups of $C(CH_3)_2$ are optionally substituted with one or more K's;

Q is O, S or Se;

Z is QH, QU' wherein U' is a hydroxyl-protecting group, or V;

W and W' are each independently hydrogen, K or V;

K is optionally one or more substituents of the indicated moiety other than hydrogen that do not preclude the first fluorophore from fluorescing;

L is a cleavable chemical moiety; and

V is a chemical moiety comprising a first Lewis base capable of coordinating to a metal ion, provided that when V occurs in Z and there is an oxygen atom directly bonded to the 6' carbon of the indicated aromatic ring, the Lewis base in V is not that oxygen atom, and wherein one or more fluorescence properties of the first fluorophore measurably change upon coordination of the first Lewis base to a metal ion.

In certain instances, cleavage of the cleavable moiety L renders the resulting fluorophore-containing portion of the compound less membrane permeable than the subject compound.

In other embodiments, the subject compounds have the structures described in certain of the claims below, all of which claims are hereby incorporated by reference in their entirety into this Summary to describe the present invention.

In another aspect, the present invention is directed to coordination complexes comprising a subject ligand complexed to one or more metal ions.

In another aspect, the present invention is directed to intermediates used to prepare the subject compounds (of which the intermediates are examples), and synthetic methods used in their preparation.

In another aspect, the present invention provides a number of methods of making and using the subject compounds, ligands and coordination complexes.

In another aspect, the subject invention involves methods of using the subject compounds to detect, and, optionally, to quantify concentrations of, metal ions in a sample or a patient. Usually, the detection methods rely on the change observed in the fluorescence of a fluorophore contained in a subject compound upon complexation with a metal ion. Any change observed, both positive and negative, and including, for example, a change in the emission wavelength, the excitation wavelength, the brightness and the quantum yield, may be used to detect metal ion complexation. The methods may be used in vivo to detect changes in intracellular concentrations of metal ions with the appropriate subject compounds. In addition, the present inventive methods provide for positive and negative controls.

In another aspect, the subject compounds may be used to quantify the concentration of a metal ion. For example, in one embodiment as shown for the subject compound depicted in FIG. 17, it is possible to determine the concentration of a metal ion by comparing the emission spectra of the two fluorophores that are contained in such subject compound. FIG. 20 shows the results of such a measurement for that subject compound. Determining ratios of excitation amplitude or emission amplitude at two different wavelengths ("excitation amplitude ratioing" and "emission amplitude ratioing", respectively) may be advantageous because through the ratioing process it may be possible to provide an internal reference and cancel out variations in the absolute brightness of the excitation source, the sensitivity of the detector, and light scattering or quenching by the sample, among other things.

In another aspect, the present invention is directed to methods of using the subject compounds for diagnostic purposes. In certain instances, the subject compounds and methods may be used to detect, and, optionally, to quantify the concentration of, a metal ion of interest in a patient or sample.

In another aspect, the present invention is directed to methods of using the subject compounds for determining the presence of analytes in samples, including samples of environmental interest.

In other embodiments, this invention contemplates a kit including subject compounds, and optionally instructions for their use. Uses for such kits include, for example, diagnostic applications.

These embodiments of the present invention, other embodiments, and their features and characteristics, will be apparent from the description, drawings and claims that follow.

4. BRIEF DESCRIPTION OF THE DRAWINGS

FIGS. 1A and B depict various Lewis bases contained in V for certain embodiments of the subject compounds, which moieties are also referred to as D.

Figure 4:
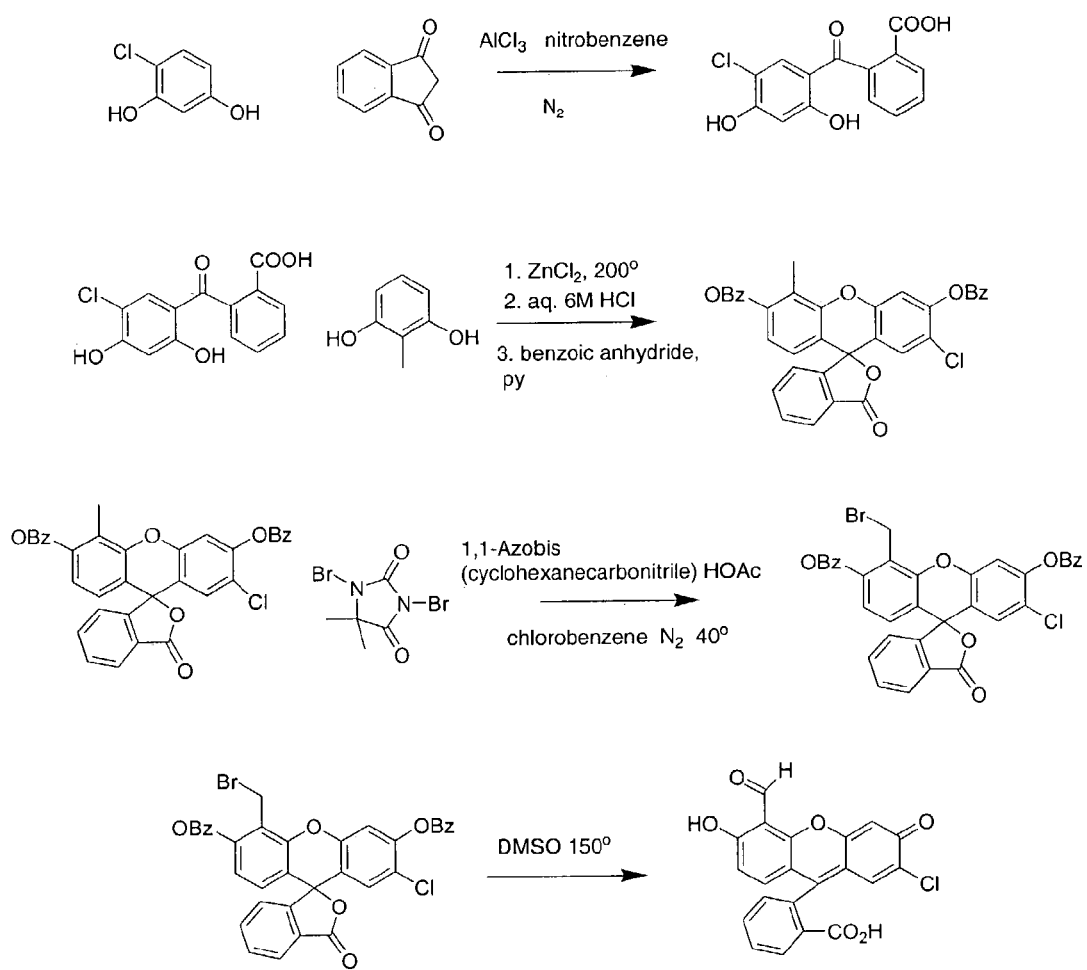

FIG. 4 presents a schematic for the synthesis of 7-chloro-4'-fluoresceincarboxaldehyde.

Figure 5:
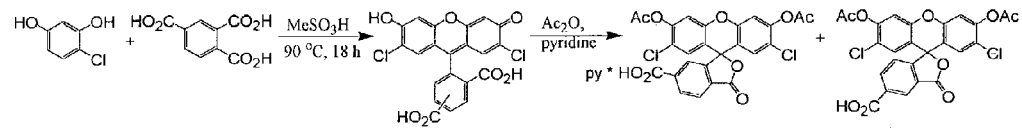
Figure 5:
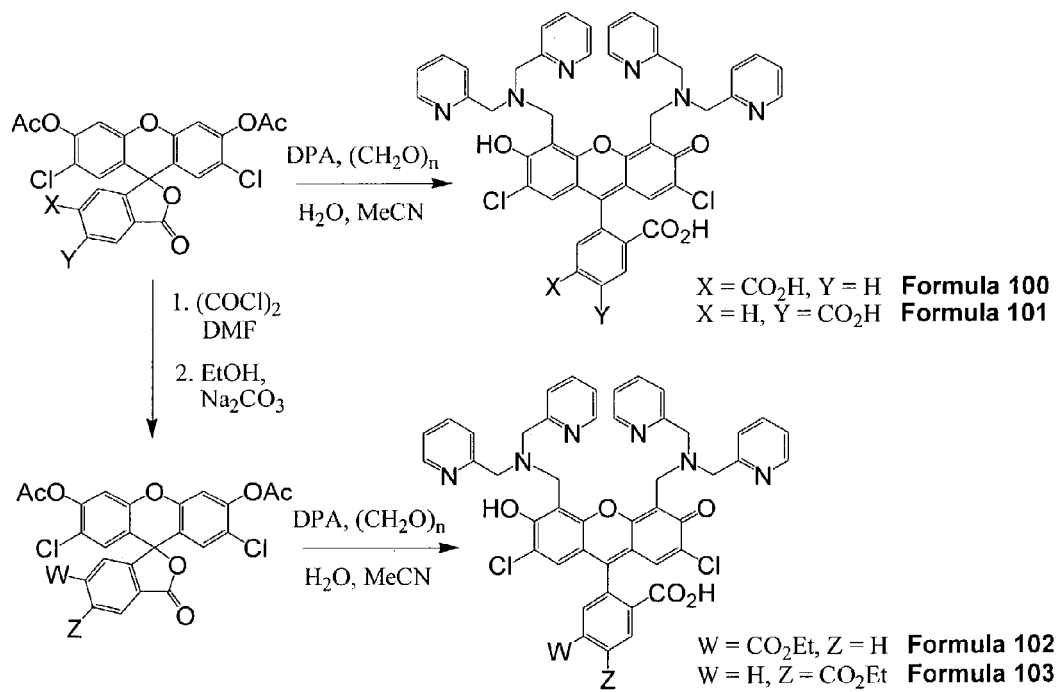

FIG. 5 depicts schematics for the synthesis of Formulas 100-103 via the Mannich reaction. The top schematic A depicts the synthesis of dichlorofluorescein 5- and 6-carboxylate isomers, which are separated as the diacetates. The bottom schematic B depicts the subsequent synthesis from the diacetates via the Mannich reaction.

Figure 6:
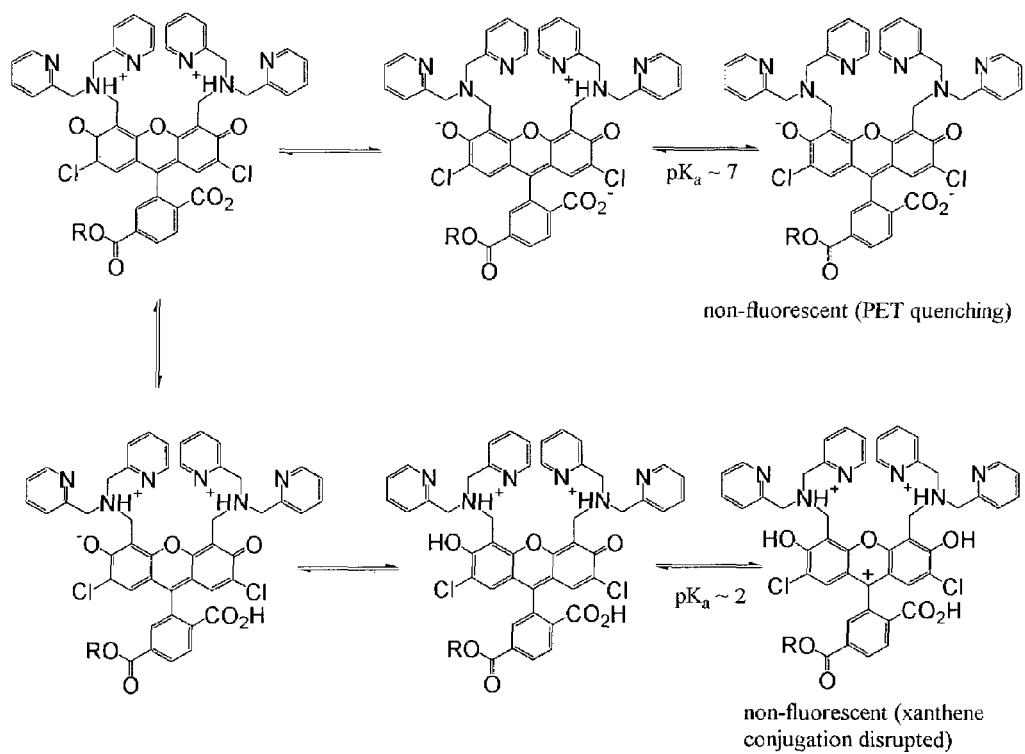

FIG. 6 depicts the stepwise protonation of the ligand of Formula 102 or Formula 100.

Figure 7:
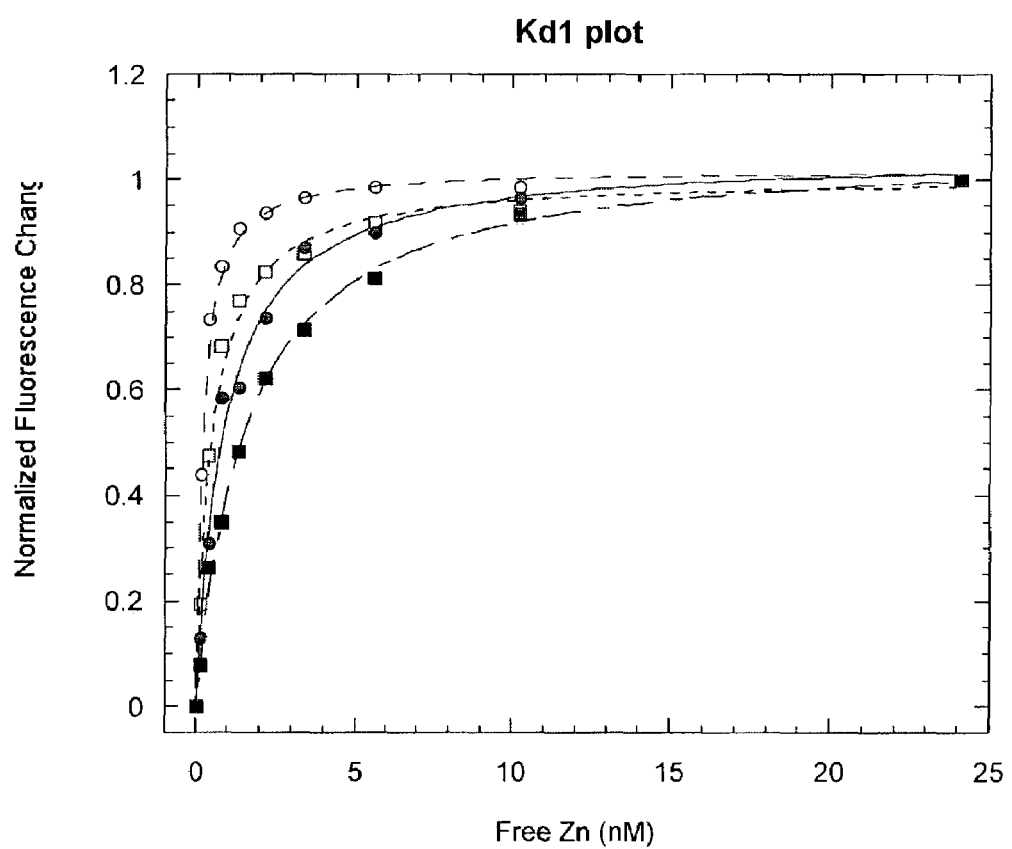

FIG. 7 depicts the determination of the first dissociation constant for the Formula 101 (filled circles), Formula 103 (filled squares), Formula 100 (open circles), and Formula 102 (open squares) ligands.

Figure 8:
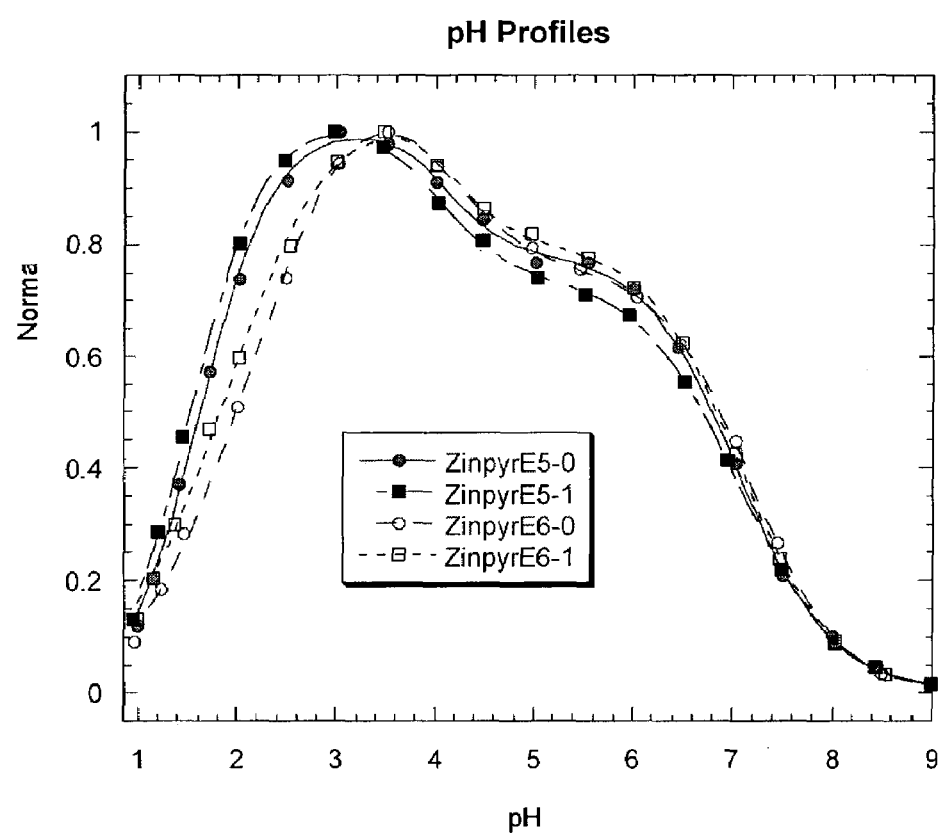

FIG. 8 depicts the pH profiles of the Formula 101 (filled circles), Formula 103 (filled squares), Formula 100 (open circles), and Formula 102 (open squares) ligands.

Figure 9:
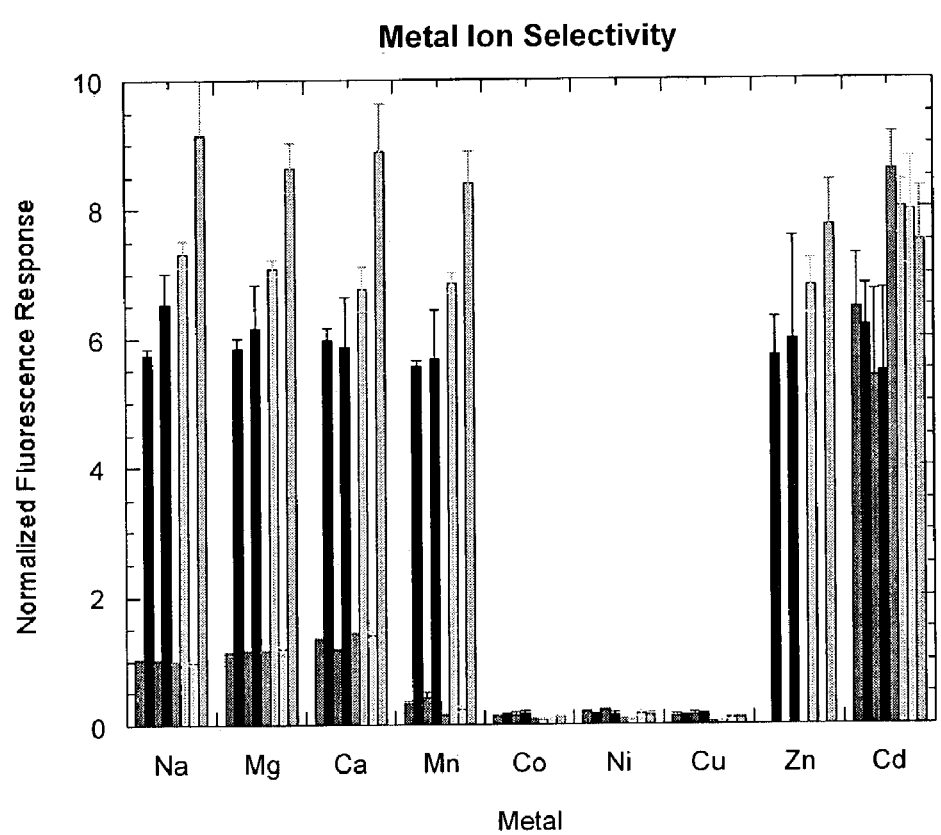

FIG. 9 depicts the fluorescence response of the Formula 101 (red, blue), Formula 103 (green, black), Formula 100 (pink, turquoise) and Formula 102 (yellow, orange) ligands after titration first with various metal ions (NaCl 10 mM, $MgCl_2$ and $CaCl_2$ 4 mM), followed by titration with $ZnCl_2$ (50 μM).

Figure 10:
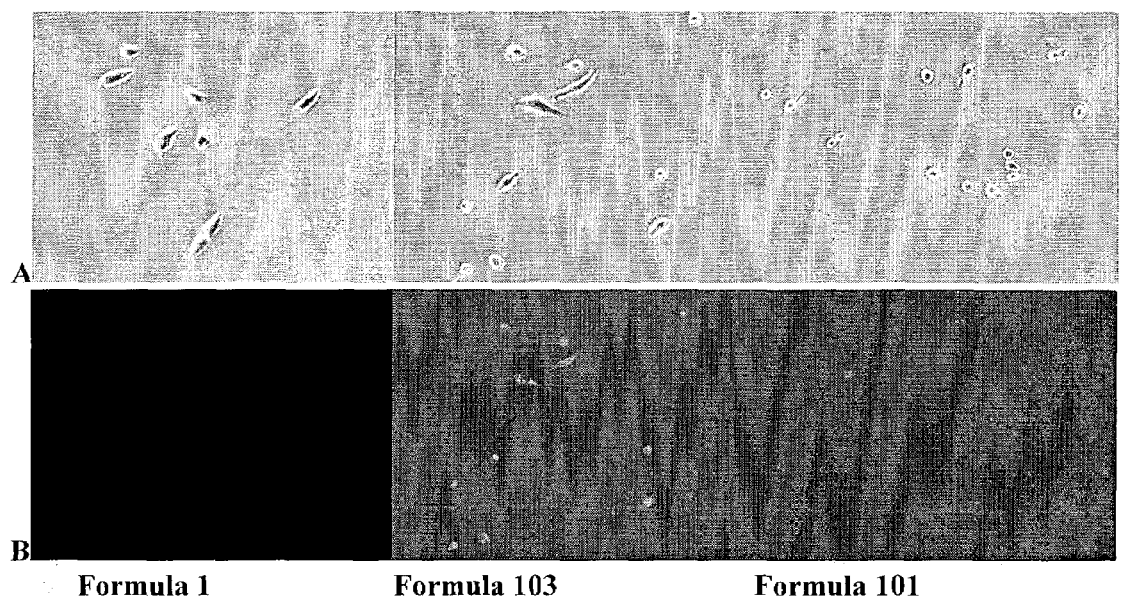

FIG. 10 depicts phase contrast (A) and fluorescence microscopy (B) visualization of HeLa cells treated with the ligands of Formula 101, 103, and 31 in the absence of zinc. Cells were bathed in 5 μM ligand for 30 min at RT, followed by untreated PBS for 10 min.

Figure 11:
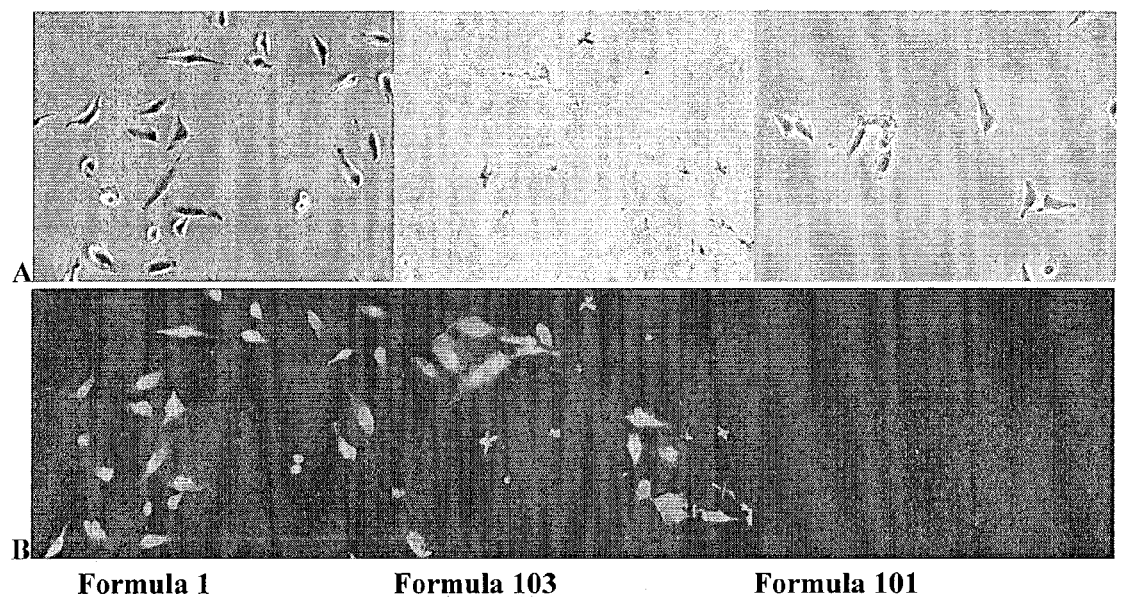

FIG. 11 depicts phase contrast (A) and fluorescence microscopy (B) visualization of HeLa cells treated with the ligands of Formula 101, 103, and 31 in the presence of zinc. Cells were bathed in 5 μM ligand for 30 min at RT, followed by 10 μM $Zn^{2+}$-pyrithione.

Figure 12:
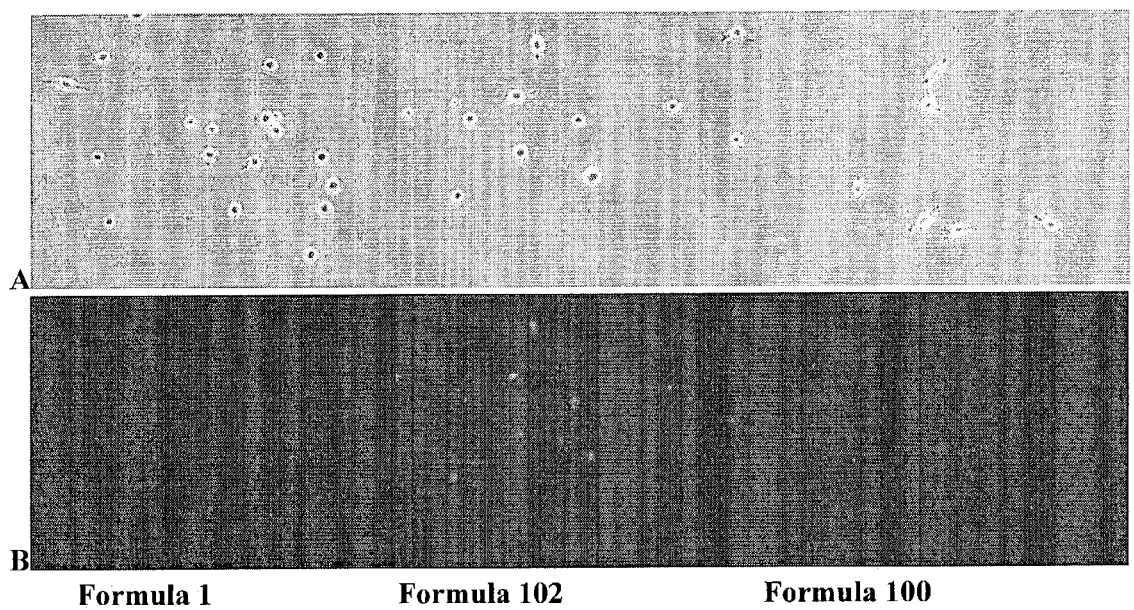

FIG. 12 depicts phase contrast (A) and fluorescence microscopy (B) visualization of HeLa cells treated with the ligands of Formula 100, 102, and 31 in the absence of zinc. Cells were bathed in 5 μM ligand for 30 min at RT, followed by untreated PBS for 10 min.

Figure 13:
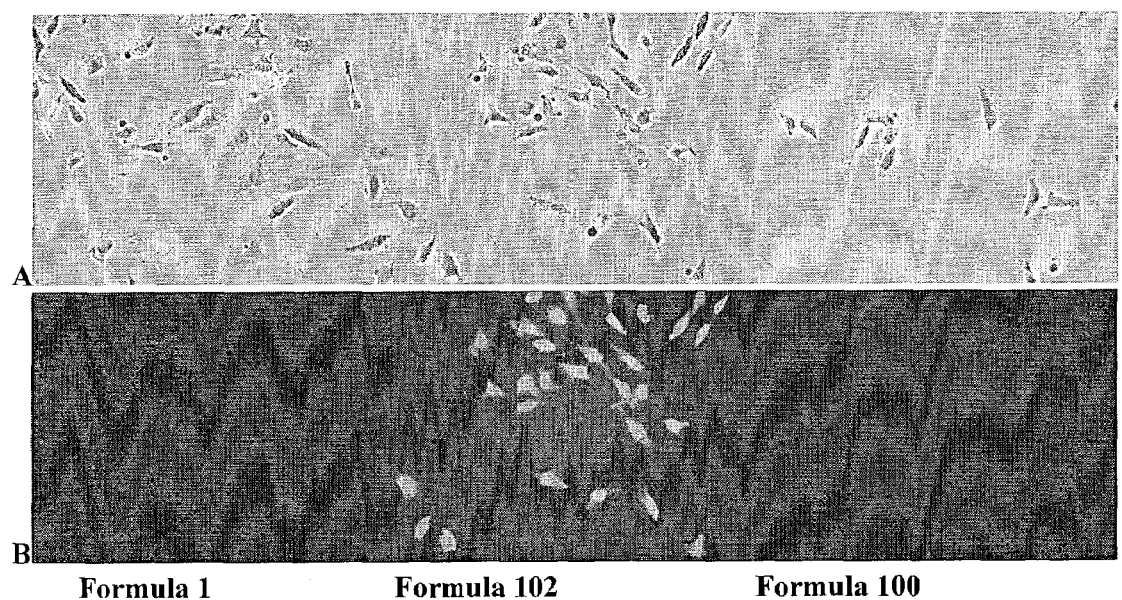

FIG. 13 depicts phase contrast (A) and fluorescence microscopy (B) visualization of HeLa cells treated with the ligands of Formula 100, 102, and 31 in the presence of zinc. Cells were bathed in 5 μM sensor for 30 min at RT, followed by 10 μM $Zn^{2+}$-pyrithione.

Figure 14:
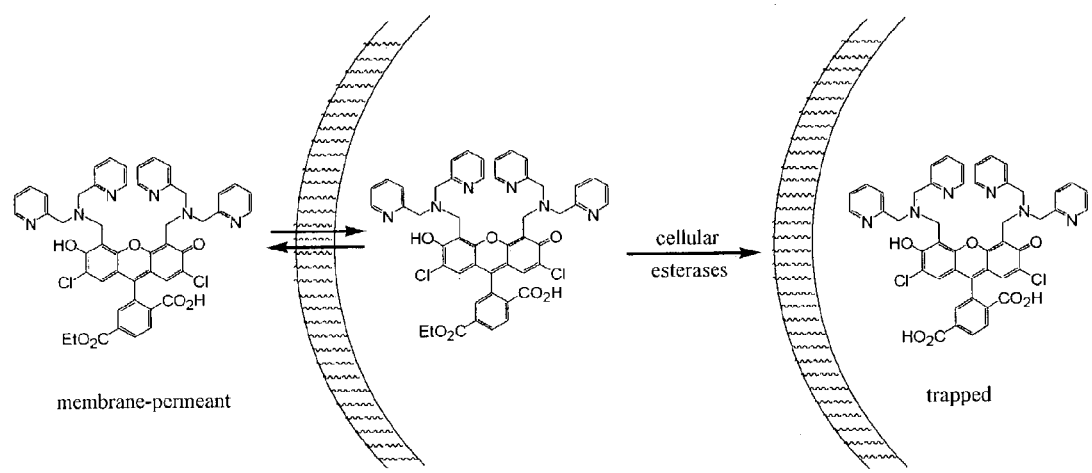

FIG. 14 depicts, without intending to limit the scope of the invention in any way, a proposed mechanism of esterase-mediated intracellular trapping of a subject compound.

Figure 15:
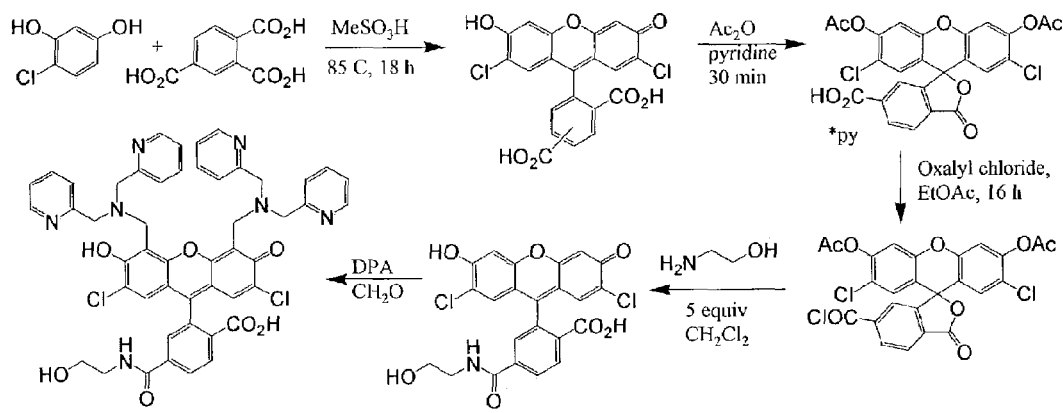

FIG. 15 depicts a schematic for the synthesis of Formula 104 {(ZinpyrA-1) via the Mannich reaction.

Figure 16:
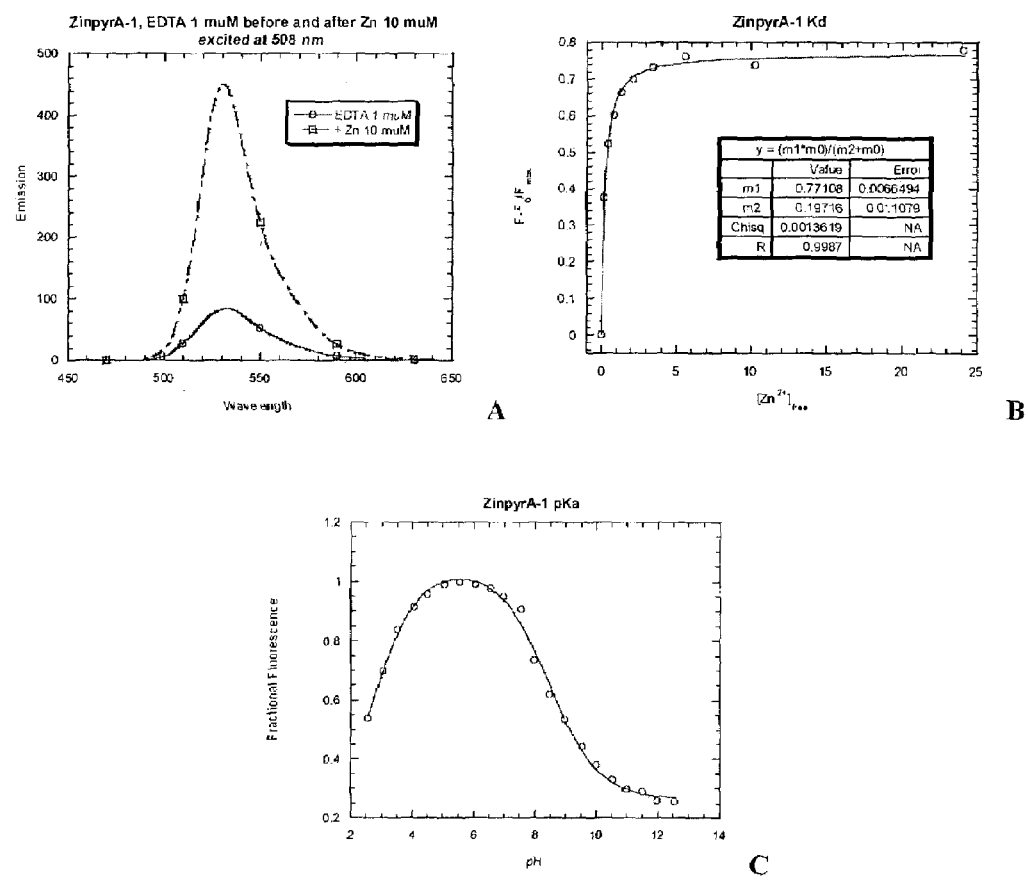

FIG. 16 depicts typical spectra and data analysis plots of Formula 104. A) depicts the $Zn^{2+}$ response of the ligand, B) depicts a $K_d$ plot, and C) depicts a fluorescence-dependent $pK_a$ fit.

Figure 17:
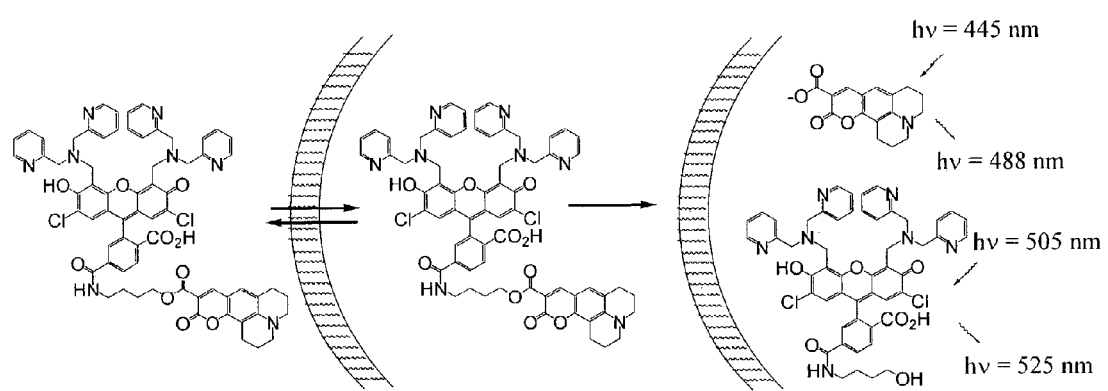

FIG. 17 depicts, without intending to limit the scope of the invention in any way, the proposed mechanism of esterase-mediated intracellular trapping of Formula 105.

Figure 18:
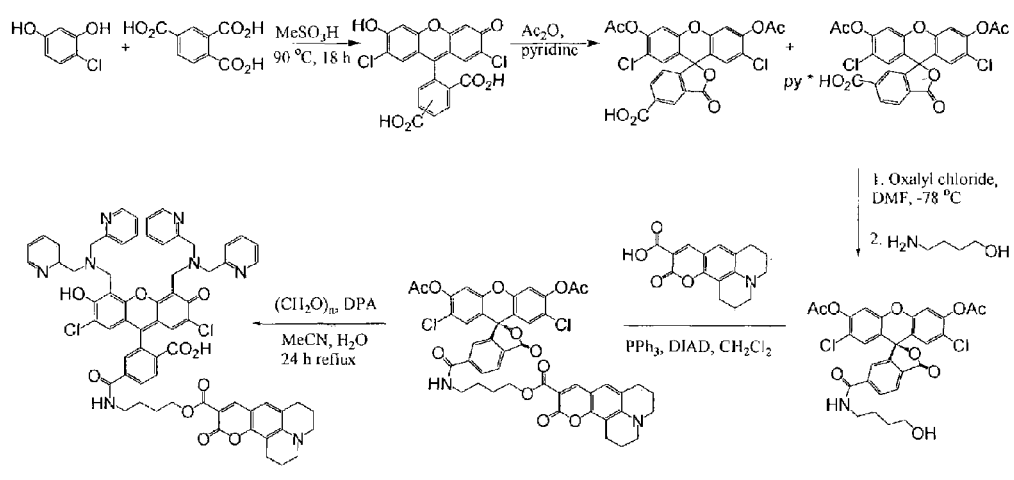

FIG. 18 depicts the synthesis of Coumazin-1 (Formula 105).

Figure 19:
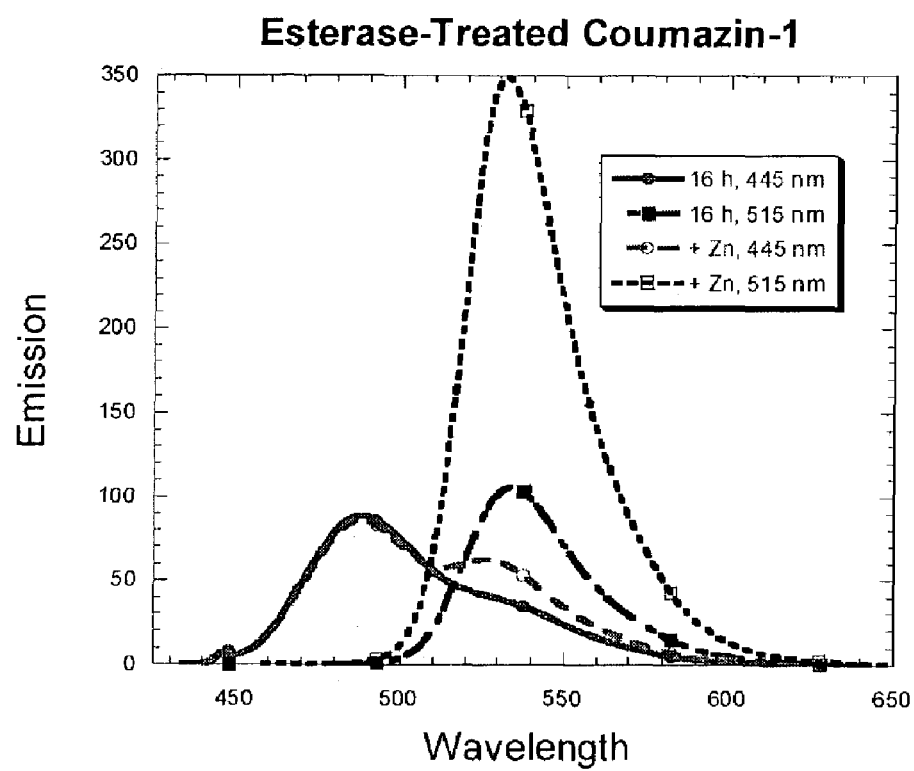

FIG. 19 depicts the results of exposing Coumazin-1 to zinc after esterase treatment. The fluorescence emission of each of Coumazin-1's constituent fluorophores was measured in the presence ("+Zn") and absence ("16 h") or zinc after treatment with esterase for 16 hours. Excitation of the coumarin fluorophore is at 445 nm, with measurement of emission at 488 nm while excitation of the fluorescein-based fluorophore is at 505 nm, with measurement of emission at 535 nm.

Figure 20:
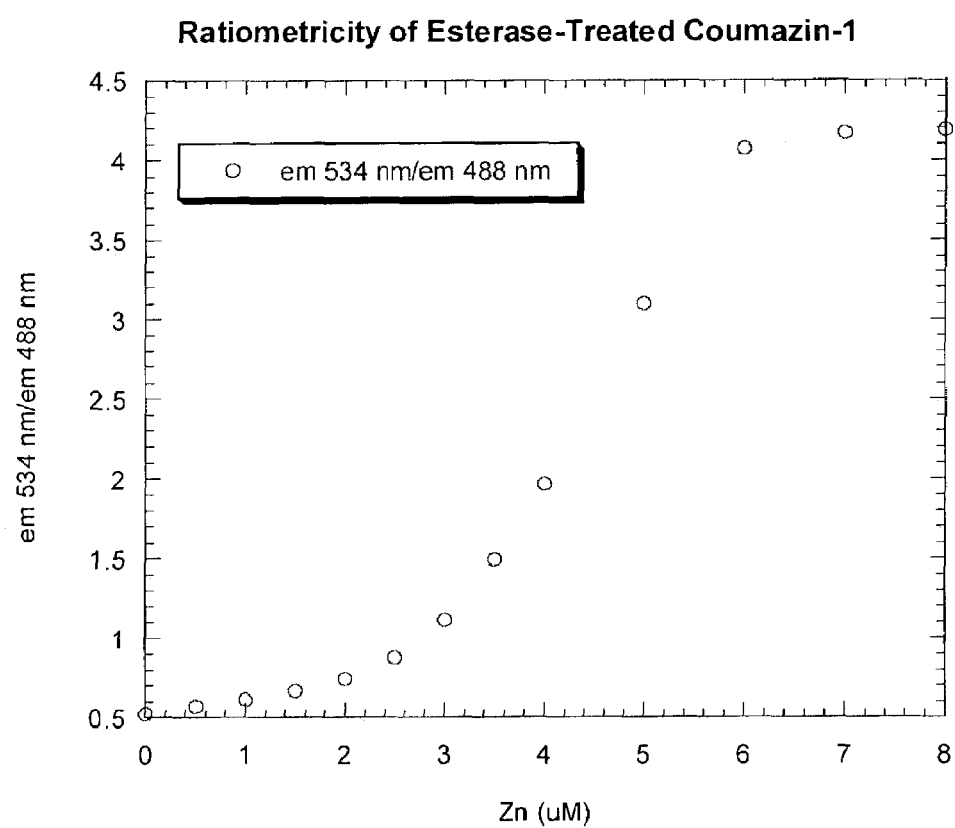

FIG. 20 depicts the ratiometricity of Coumazin-1.

Figure 21:
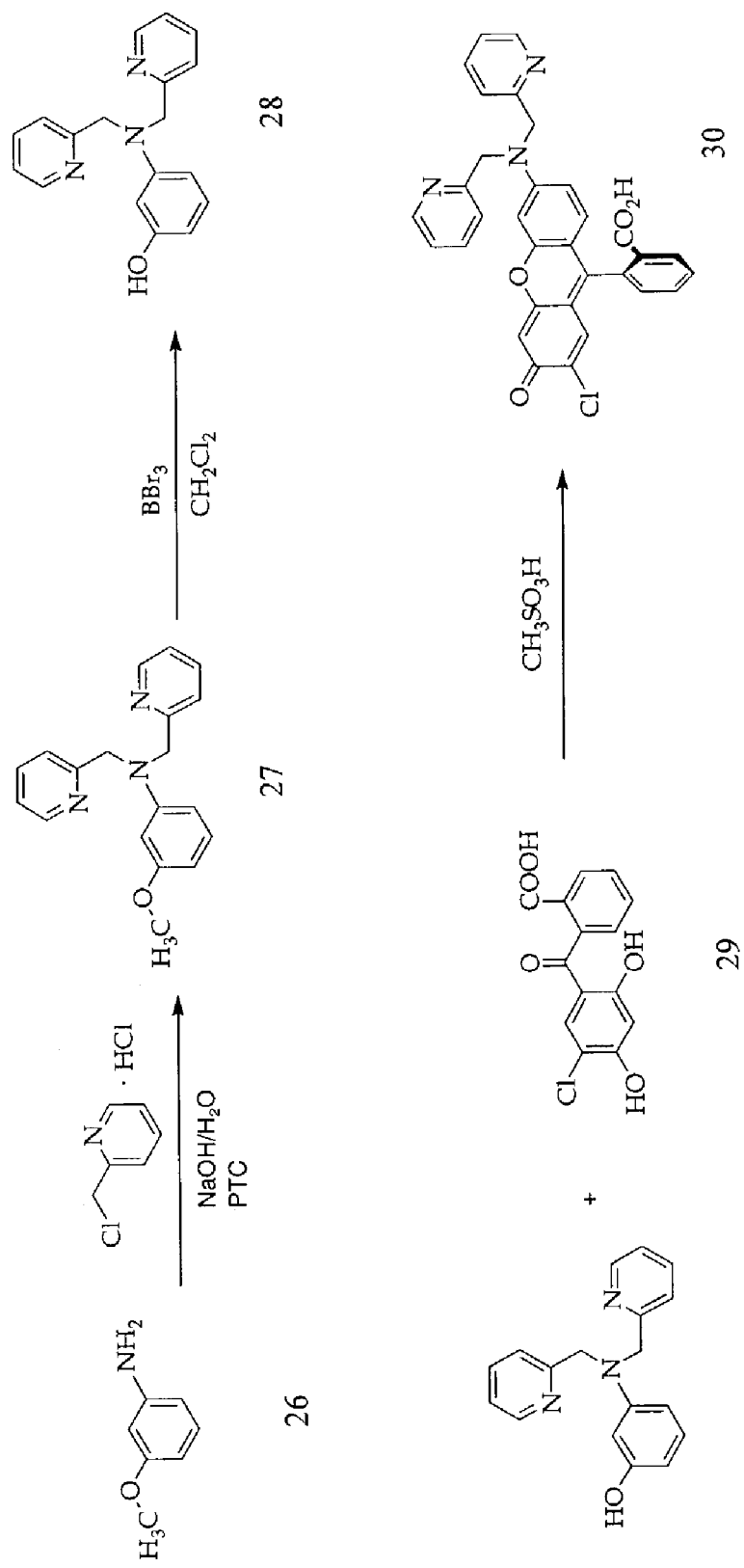

FIG. 21 shows the synthesis of a fluorescein based-ligand.

Figure 22:
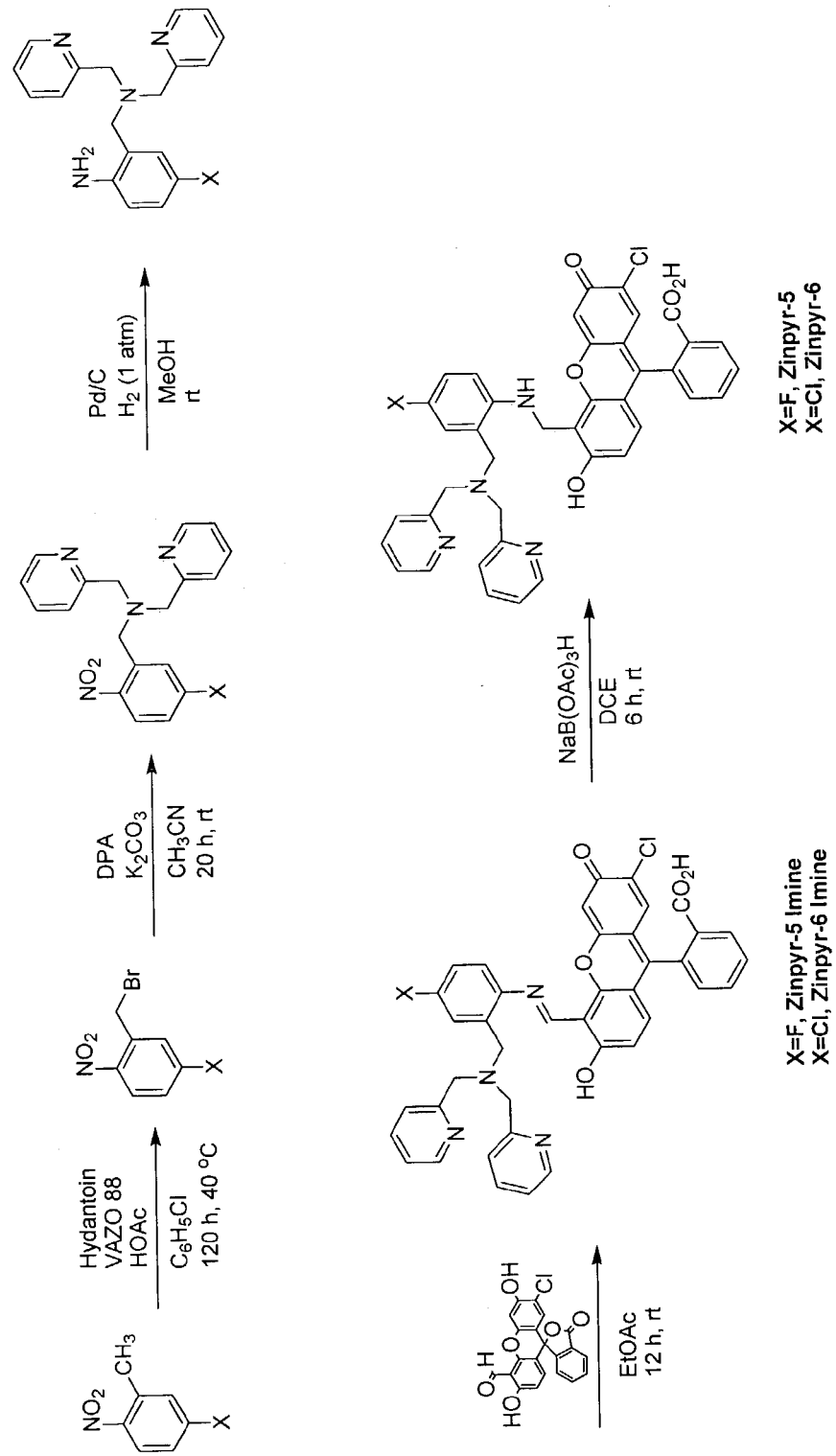

FIG. 22 shows the synthesis of Zinpyr-5 and Zinpyr-6.

Figure 23:
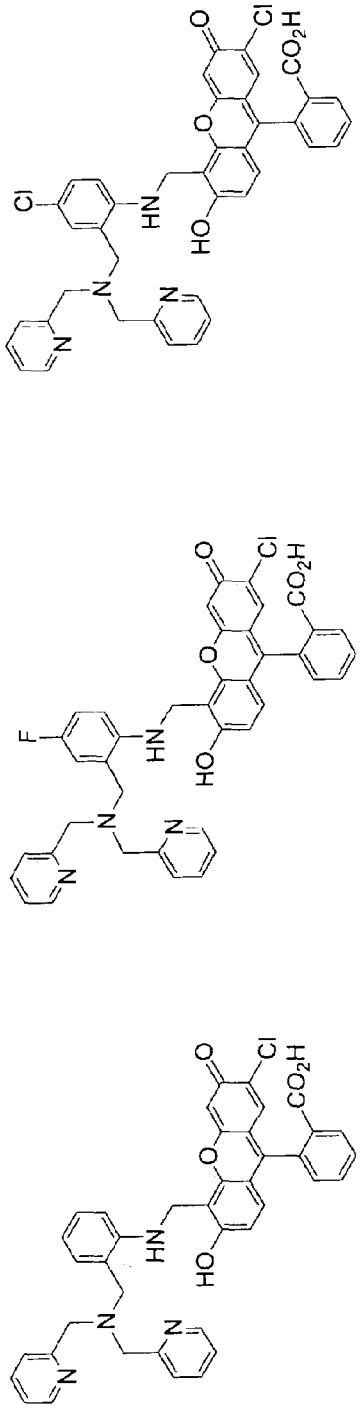

FIG. 23 shows various properties of Zinpyr-5 and Zinpyr-6 as compared to Zinpyr-4.

Figure 24:
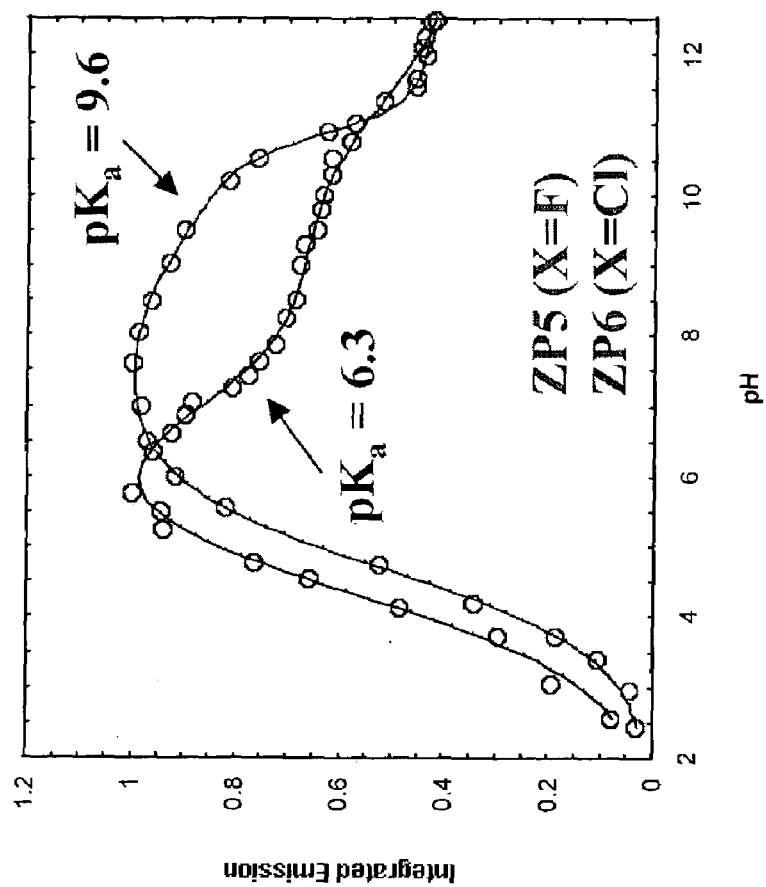
Figure 24:
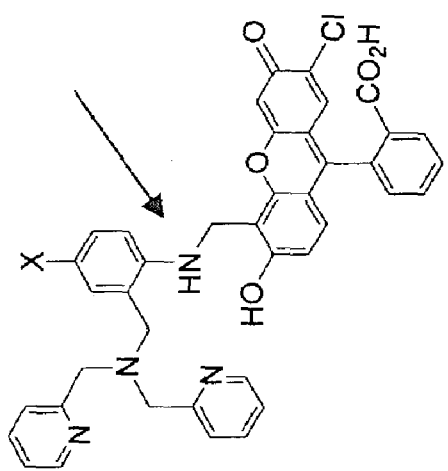

FIG. 24 shows the results of pKa experiments for Zinpyr-5 and Zinpyr-6.

Figure 25:
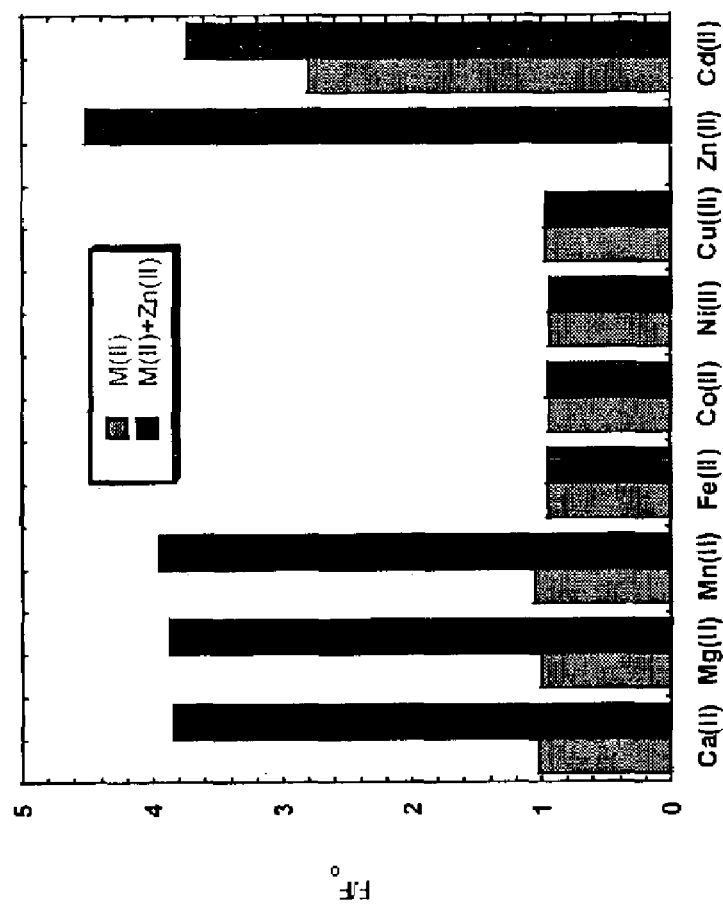

FIG. 25 shows metal selectivity for Zinpyr-5 and Zinpyr-6.

Figure 26:
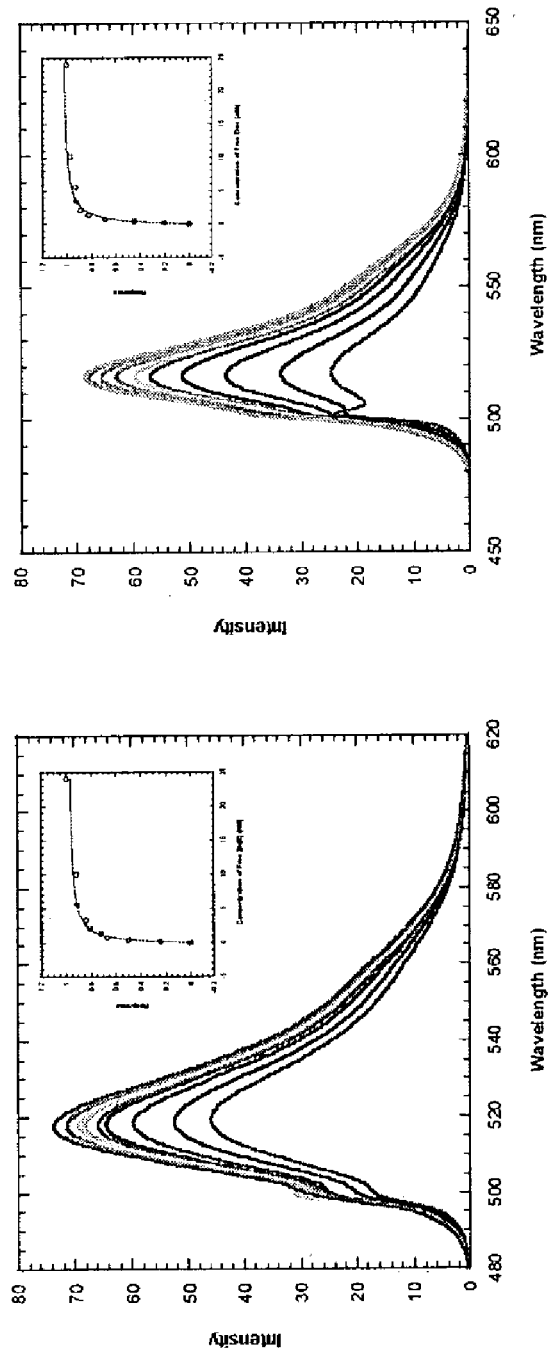

FIG. 26 shows the results of Kd experiments for Zinpyr-5 and Zinpyr-6.

5. DETAILED DESCRIPTION OF PREFERRED EMBODIMENTS

Definitions

For convenience, before further description of the present invention, certain terms employed in the specification, examples and appended claims are collected here. These definitions should be read in light of the remainder of the disclosure and understood as by a person of skill in the art.

The articles "a" and "an" are used herein to refer to one or to more than one (i.e., to at least one) of the grammatical object of the article. By way of example, "an element" means one element or more than one element.

The terms "comprise" and "comprising" are used in the inclusive, open sense, meaning that additional elements may be included.

The term "including" is used herein to mean "including but not limited to". "Including" and "including but not limited to" are used interchangeably.

The term "chromophore" is art-recognized and that refers to a molecule or part of a molecule that absorbs specific frequencies of light, including ultraviolet light.

The term "fluorophore" refers to a chromophore that fluoresces. Certain fluorophores generally absorb above 300 nm, certain fluorophores generally emit above 300 nm, and certain fluorophores both generally absorb and emit above 300 nm. Alternatively, the threshold may be 350 nm, 400 nm, 425 nm, 450 nm and 500 nm or greater for any particular fluorophore.

The terms "Lewis base" and "Lewis basic" are art-recognized and generally include a chemical moiety, a structural fragment or substituent capable of donating a pair of electrons under certain conditions. It may be possible to characterize a Lewis base as donating a single electron in certain complexes, depending on the identity of the Lewis base and the metal ion, but for most purposes, however, a Lewis base is best understood as a two electron donor. Examples of Lewis basic moieties include uncharged compounds such as alcohols, thiols, and amines, and charged moieties such as alkoxides, thiolates, carbanions, and a variety of other organic anions. A Lewis base, when coordinated to a metal ion, is often referred to as a ligand. Further description of ligands relevant to the present invention is presented below.

The term "label" refers to a composition detectable by spectroscopic, photochemical, biochemical, immunochemical chemical or other means. For example, useful labels include $^{32}P$, chromophores, fluorophores, fluorescent proteins, electron-dense reagents, enzymes (e.g., as commonly used in an ELISA), biotin, dioxigenin, or haptens and proteins for which antisera or monoclonal antibodies are available. A label often generates a measurable signal, such as radioactivity, fluorescent light or enzyme activity, which may in certain instances be used to quantitate the amount of label present.

The term "ligand" is art-recognized and refers to a species that interacts in some fashion with another species. In one example, a ligand may be a Lewis base that is capable of forming a coordinate bond with a Lewis acid. In other examples, a ligand is a species, often organic, that forms a coordinate bond with a metal ion. Ligands, when coordinated to a metal ion, may have a variety of binding modes know to those of skill in the art, which include, for example, terminal (i.e., bound to a single metal ion) and bridging (i.e., one atom of the Lewis base bound to more than one metal ion).

The term "fluorescent ratiometricity" refers to the ratio of excitation amplitudes at two different wavelengths, the ratio of emission amplitudes at two different wavelengths, or the ratio of excitation amplitude at one wavelength to the ratio of emission amplitude at another wavelength (and vice-verse).

The terms "labile" and "non-labile" are art-recognized and are usually used in this context in reference to a ligand bonded to a metal ion. Without intending to limit or modify the definition for the term as it is known in the art, a labile ligand may be understood to be a ligand whose bond to the metal ion is expected to break under certain circumstances.

The terms "Lewis acid" and "Lewis acidic" are art-recognized and refer to chemical moieties which can accept a pair of electrons from a Lewis base as defined above.

The term "fluorescent property" refers to, with respect to a fluorophore, the molar extinction coefficient at an appropriate excitation wavelength, the fluorescence quantum efficiency, the shape of the excitation spectrum or emission spectrum, the excitation wavelength maximum and emission wavelength maximum, the excited state lifetime, or the fluorescence anisotropy. A measurable difference can be determined by determining the amount of any quantitative fluorescent property, e.g., the amount of fluorescence at a particular wavelength, or the integral of fluorescence over the emission spectrum. Fluorescent properties will be affected by fluorescence resonance energy transfer ("FRET").

The term "chelating agent" is art-recognized and refers to a molecule, often an organic one, and often a Lewis base, having two or more unshared electron pairs available for donation to a metal ion. The metal ion is usually coordinated by two or more electron pairs to the chelating agent. The terms, "bidentate chelating agent", "tridentate chelating agent", and "tetradentate chelating agent" refer to chelating agents having, respectively, two, three, and four electron pairs readily available for simultaneous donation to a metal ion coordinated by the chelating agent. Usually, the electron pairs of a chelating agent form coordinate bonds with a single metal ion; however, in certain examples, a chelating agent may form coordinate bonds with more than one metal ion, with a variety of binding modes being possible.

The term "coordination" is art-recognized and refers to an interaction in which one multi-electron pair donor coordinatively bonds (is "coordinated") to one metal ion.

The terms "coordinate bond" or "coordination bond" are art-recognized and refer to an interaction between an electron pair donor and a coordination site on a metal ion leading to an attractive force between the electron pair donor and the metal ion. The use of these terms is not intended to be limiting, in so much as certain coordinate bonds may also be classified as having more or less covalent character (if not entirely covalent character) depending on the nature of the metal ion and the electron pair donor.

The term "covalent bond" is art-recognized and refers to a bond between two atoms where electrons are attracted electrostatically to both nuclei of the two atoms, and the net effect of increased electron density between the nuclei counterbalances the internuclear repulsion. The term covalent bond includes coordinate bonds when the bond is with a metal ion.

The term "covalently linked" and variations thereof when used in reference to a subject compound refers to the connection of two fluorophores by a cleavable linker, so that before the linker is cleaved, the two fluorophores and the cleavable linker would be understood to be part of the same molecule.

The term "coordination site" is art-recognized and refers to a point on a metal ion that can accept an electron pair donated, for example, by a liquid or chelating agent.

The term "free coordination site" is art-recognized and refers to a coordination site on a metal ion that is vacant or occupied by a species that is weakly donating. Such species is readily displaced by another species, such as a Lewis base.

The term "coordination number" is art-recognized and refers to the number of coordination sites on a metal ion that are available for accepting an electron pair.

The term "coordination geometry" is art-recognized and refers to the manner in which coordination sites and free coordination sites are spatially arranged around a metal ion. Some examples of coordination geometry include octahedral, square planar, trigonal, trigonal biplanar and others known to those of skill in the art.

The term "complex" is art-recognized and means a compound formed by the union of one or more electron-rich and electron-poor molecules or atoms capable of independent existence with one or more electronically poor molecules or atoms, each of which is also capable of independent existence. A "coordination complex" is one type of a complex, in which there is a coordinate bond between a metal ion and an electron pair donor. A metal ion complex is a coordination complex in which the metal ion is a metal ion. In general, the terms "compound," "composition," "agent" and the like discussed herein include complexes, coordination complexes and metal ion complexes. As a general matter, the teachings of *Advanced Inorganic Chemistry* by Cotton and Wilkinson are referenced as supplementing the definitions herein in regard to coordination complexes and related matters.

In certain circumstances, a coordination complex may be understood to be composed of its constitutive components. For example, a coordination complex may have the following components: (i) one or more metal ions, which may or may not be the same atom, have the same charge, coordination number or coordination geometry and the like; and (ii) one or more Lewis bases that form coordinate bonds with the metal ion(s). Examples of such Lewis bases include chelating agents and ligands.

If a coordination complex is charged, in that the metal ion and any Lewis bases in the aggregate are not neutral, then such a complex will usually have one or more counterions to form a neutral compound. Such counterions may or may not be considered part of the coordination complex depending on how the term coordination complex is used. Counterions generally do not form coordinate bonds to the metal ion, although they may be associated, often in the solid state, with the metal ion or Lewis bases that make up the coordination complex. Some examples of counterions include monoanions such as nitrate, chloride, tetraflurorborate, hexafluorophosphate, and monocarboxylates, and dianions such as sulfate. In some cases, coordination complexes themselves may serve as counterions to another coordination complex.

The same chemical moiety may be either a ligand or a counterion to a coordination complex. For example, the anionic ligand chloride may be either coordinately bound to a metal ion or may act as a counterion without any need for bond formation. The exact form observed for chloride in any coordination complex will depend on a variety of factors including theoretical considerations such as kinetic versus thermodynamic effects, as well as the actual synthetic procedures utilized to make the coordination complex, such as the extent of reaction, acidity, concentration of chloride. These considerations are applicable to other counterions as well.

Additionally, a coordination complex may be solvated. Solvation refers to molecules, usually of solvent and often water, that associate with the coordination complex in the solid state. Again, as for counterions, such salvation molecules may or may not be considered part of the coordination complex depending on how the term coordination complex is used.

The term "cleavable linker," when used in reference to a subject compound, refers to a moiety that connects a first fluorophore and a second fluorophore and that is cleavable by chemical, photochemical, enzymatic or other means when the subject compound is used to measure the presence and/or concentration of a metal ion under suitable conditions. Formula 105 contains one example of such a linker. The term "cleavable moiety", when used in reference to a subject compound, refers to a moiety that is cleavable by chemical, photochemical, enzymatic or other means to give a fluorophore and a non-fluorophore product when the subject compound is used to measure the presence and/or concentration of a metal ion under suitable conditions. Formula 104 contains one example of such a moiety. In certain instances, the cleavable linker or moiety is intended to be cleaved once the subject compound has reached the site at which a measurement of metal ion concentration is desired, e.g. a cell or type of tissue or location in a patient.

The term "naturally-occurring", as applied to an object, refers to the fact that an object can be found in nature. For example, an enzyme that is present in an organism that can be isolated from a source in nature and which has not been intentionally modified by man in the laboratory is naturally-occurring.

The terms "combinatorial library" or "library" are art-recognized and refer to a plurality of compounds, which may be termed "members," synthesized or otherwise prepared from one or more starting materials by employing either the same or different reactants or reaction conditions at each reaction in the library. There are a number of other terms of relevance to combinatorial libraries (as well as other technologies). The term "identifier tag" is art-recognized and refers to a means for recording a step in a series of reactions used in the synthesis of a chemical library. The term "immobilized" is art-recognized and, when used with respect to a species, refers to a condition in which the species is attached to a surface with an attractive force stronger than attractive forces that are present in the intended environment of use of the surface, and that act on the species. The term "solid support" is art-recognized and refers to a material which is an insoluble matrix, and may (optionally) have a rigid or semi-rigid surface. The term "linker" is art-recognized and refers to a molecule or group of molecules connecting a support, including a solid support or polymeric support, and a combinatorial library member. The term "polymeric support" is art-recognized and refers to a soluble or insoluble polymer to which a chemical moiety can be covalently bonded by reaction with a functional group of the polymeric support. The term "functional group of a polymeric support" is art-recognized and refers to a chemical moiety of a polymeric support that can react with an chemical moiety to form a polymer-supported amino ester.

The term "synthetic" is art-recognized and refers to production by in vitro chemical or enzymatic synthesis.

The term "meso compound" is art-recognized and means a chemical compound which has at least two chiral centers but is achiral due to a plane or point of symmetry.

The term "chiral" is art-recognized and refers to molecules which have the property of non-superimposability of the mirror image partner, while the term "achiral" refers to molecules which are superimposable on their mirror image partner. A "prochiral molecule" is a molecule which has the potential to be converted to a chiral molecule in a particular process.

The term "stereoisomers" is art-recognized and refers to compounds which have identical chemical constitution, but differ with regard to the arrangement of the atoms or groups in space. In particular, "enantiomers" refer to two stereoisomers of a compound which are non-superimposable mirror images of one another. "Diastereomers", on the other hand, refers to stereoi somers with two or more centers of dissymmetry and whose molecules are not mirror images of one another.

Furthermore, a "stereoselective process" is one which produces a particular stereoisomer of a reaction product in preference to other possible stereoisomers of that product. An "enantioselective process" is one which favors production of one of the two possible enantiomers of a reaction product.

The term "regioisomers" is art-recognized and refers to compounds which have the same molecular formula but differ in the connectivity of the atoms. Accordingly, a "regioselective process" is one which favors the production of a particular regioisomer over others, e.g., the reaction produces a statistically significant increase in the yield of a certain regioisomer.

The term "epimers" is art-recognized and refers to molecules with identical chemical constitution and containing more than one stereocenter, but which differ in configuration at only one of these stereocenters.

The term "aliphatic" is art-recognized and refers to a linear, branched, cyclic alkane, alkene, or alkyne. In certain embodiments, aliphatic groups in the present invention are linear or branched and have from 1 to about 20 carbon atoms.

The term "alkyl" is art-recognized, and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., $C_1$-$C_{30}$ for straight chain, $C_3$-$C_{30}$ for branched chain), and alternatively, about 20 or fewer. Likewise, cycloalkyls have from about 3 to about 10 carbon atoms in their ring structure, and alternatively about 5, 6 or 7 carbons in the ring structure. The term "alkyl" is also defined to include halosubstituted alkyls.

Moreover, the term "alkyl" (or "lower alkyl") includes "substituted alkyls", which refers to alkyl moieties having substituents replacing a hydrogen on one or more carbons of the hydrocarbon backbone. Such substituents may include, for example, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain may themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —CN and the like. Exemplary substituted alkyls are described below. Cycloalkyls may be further substituted with alkyls, alkenyls, alkoxys, alkylthios, aminoalkyls, carbonyl-substituted alkyls, —CN, and the like.

The term "aralkyl" is art-recognized and refers to an alkyl group substituted with an aryl group (e.g., an aromatic or heteroaromatic group).

The terms "alkenyl" and "alkynyl" are art-recognized and refer to unsaturated aliphatic groups analogous in length and possible substitution to the alkyls described above, but that contain at least one double or triple bond respectively.

Unless the number of carbons is otherwise specified, "lower alkyl" refers to an alkyl group, as defined above, but having from one to about ten carbons, alternatively from one to about six carbon atoms in its backbone structure. Likewise, "lower alkenyl" and "lower alkynyl" have similar chain lengths.

The term "heteroatom" is art-recognized and refers to an atom of any element other than carbon or hydrogen. Illustrative heteroatoms include boron, nitrogen, oxygen, phosphorus, sulfur and selenium.

The term "aryl" is art-recognized and refers to 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring may be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, aryls and/or heterocyclyls.

The terms ortho, meta and para are art-recognized and refer to 1,2-, 1,3- and 1,4-disubstituted benzenes, respectively. For example, the names 1,2-dimethylbenzene and ortho-dimethylbenzene are synonymous.

The terms "heterocyclyl" or "heterocyclic group" are art-recognized and refer to 3- to about 10-membered ring structures, alternatively 3- to about 7-membered rings, whose ring structures include one to four heteroatoms. Heterocycles may also be polycycles. Heterocyclyl groups include, for example, thiophene, thianthrene, furan, pyran, isobenzofuran, chromene, xanthene, phenoxanthene, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring may be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The terms "polycyclyl" or "polycyclic group" are art-recognized and refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle may be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The term "carbocycle" is art-recognized and refers to an aromatic or non-aromatic ring in which each atom of the ring is carbon.

The term "nitro" is art-recognized and refers to —$NO_2$; the term "halogen" is art-recognized and refers to —F, —Cl, —Br or —I; the term "sulfhydryl" is art-recognized and refers to —SH; the term "hydroxyl" means —OH; and the term "sulfonyl" is art-recognized and refers to —SO$_2^-$. "Halide" designates the corresponding anion of the halogens, and "pseudohalide" has the definition set forth on 560 of *Advanced Inorganic Chemistry* by Cotton and Wilkinson.

The terms "amine" and "amino" are art-recognized and refer to both unsubstituted and substituted amines, e.g., a moiety that may be represented by the general formulas:

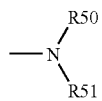 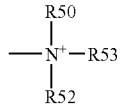

wherein R50, R51 and R52 each independently represent a hydrogen, an alkyl, an alkenyl, —(CH$_2$)$_m$—R61, or R50 and R51, taken together with the N atom to which they are attached complete a heterocycle having from 4 to 8 atoms in the ring structure; R61 represents an aryl, a cycloalkyl, a cycloalkenyl, a heterocycle or a polycycle; and m is zero or an integer in the range of 1 to 8. In certain embodiments, only one of R50 or R51 may be a carbonyl, e.g., R50, R51 and the nitrogen together do not form an imide. In other embodiments, R50 and R51 (and optionally R52) each independently represent a hydrogen, an alkyl, an alkenyl, or —(CH$_2$)$_m$—R61. Thus, the term "alkylamine" includes an amine group, as defined above, having a substituted or unsubstituted alkyl attached thereto, i.e., at least one of R50 and R51 is an alkyl group.

The term "ammine" is art-recognized are refers to a compound containing an ammonia moiety or moieties coordinated to a metal ion. The term "ammonia" is art-recognized an refers to an amine group substituted with hydrogens.

The term "acylamino" is art-recognized and refers to a moiety that may be represented by the general formula:

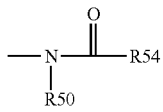

wherein R50 is as defined above, and R54 represents a hydrogen, an alkyl, an alkenyl or —(CH$_2$)$_m$—R61, where m and R61 are as defined above.

The term "amido" is art recognized as an amino-substituted carbonyl and includes a moiety that may be represented by the general formula:

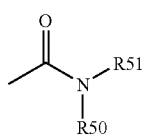

wherein R50 and R51 are as defined above. Certain embodiments of the amide in the present invention will not include imides which may be unstable.

The term "alkylthio" refers to an alkyl group, as defined above, having a sulfur radical attached thereto. In certain embodiments, the "alkylthio" moiety is represented by one of —S-alkyl, —S-alkenyl, —S-alkynyl, and —S—(CH$_2$)$_m$— R61, wherein m and R61 are defined above. Representative alkylthio groups include methylthio, ethyl thio, and the like.

The term "carbonyl" is art recognized and includes such moieties as may be represented by the general formulas:

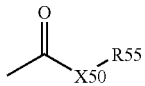 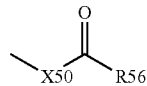

wherein X50 is a bond or represents an oxygen or a sulfur, and R55 and R56 represents a hydrogen, an alkyl, an alkenyl, —(CH$_2$)$_m$—R61 or a pharmaceutically acceptable salt, R56 represents a hydrogen, an alkyl, an alkenyl or —(CH$_2$)$_m$— R61, where m and R61 are defined above. Where X50 is an oxygen and R55 or R56 is not hydrogen, the formula represents an "ester". Where X50 is an oxygen, and R55 is as defined above, the moiety is referred to herein as a carboxyl group, and particularly when R55 is a hydrogen, the formula represents a "carboxylic acid". Where X50 is an oxygen, and R56 is hydrogen, the formula represents a "formate". In general, where the oxygen atom of the above formula is replaced by sulfur, the formula represents a "thiolcarbonyl" group. Where X50 is a sulfur and R55 or R56 is not hydrogen, the formula represents a "thiolester." Where X50 is a sulfur and R55 is hydrogen, the formula represents a "thiolcarboxylic acid." Where X50 is a sulfur and R56 is hydrogen, the formula represents a "thiolformate." On the other hand, where X50 is a bond, and R55 is not hydrogen, the above formula represents a "ketone" group. Where X50 is a bond, and R55 is hydrogen, the above formula represents an "aldehyde" group.

The terms "alkoxyl" or "alkoxy" are art-recognized and refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, —O——(CH$_2$)$_m$—R61, where m and R61 are described above.

The term "sulfonate" is art recognized and refers to a moiety that may be represented by the general formula:

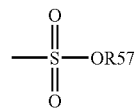

in which R57 is an electron pair, hydrogen, alkyl, cycloalkyl, or aryl.

The term "sulfate" is art recognized and includes a moiety that may be represented by the general formula:

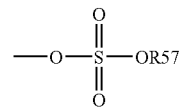

in which R57 is as defined above.

The term "sulfonamido" is art recognized and includes a moiety that may be represented by the general formula:

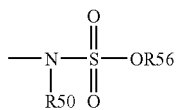

in which R50 and R56 are as defined above.

The term "sulfamoyl" is art-recognized and refers to a moiety that may be represented by the general formula:

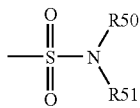

in which R50 and R51 are as defined above.

The term "sulfonyl" is art-recognized and refers to a moiety that may be represented by the general formula:

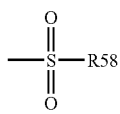

in which R58 is one of the following: hydrogen, alkyl, alkenyl, alkynyl, cycloalkyl, heterocyclyl, aryl or heteroaryl.

The term "sulfoxido" is art-recognized and refers to a moiety that may be represented by the general formula:

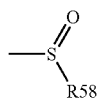

in which R58 is defined above.

The term "phosphoryl" is art-recognized and may in general be represented by the formula:

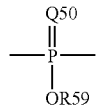

wherein Q50 represents S or O, and R59 represents hydrogen, a lower alkyl or an aryl. When used to substitute, e.g., an alkyl, the phosphoryl group of the phosphorylalkyl may be represented by the general formulas:

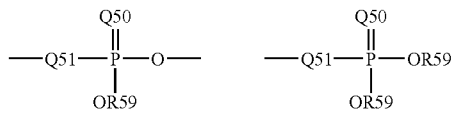

wherein Q50 and R59, each independently, are defined above, and Q51 represents O, S or N. When Q50 is S, the phosphoryl moiety is a "phosphorothioate".

The term "phosphoramidite" is art-recognized and may be represented in the general formulas:

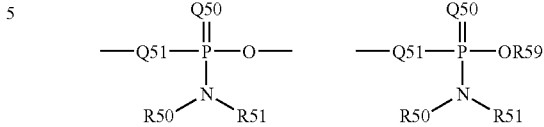

wherein Q51, R50, R51 and R59 are as defined above.

The term "phosphonamidite" is art-recognized and may be represented in the general formulas:

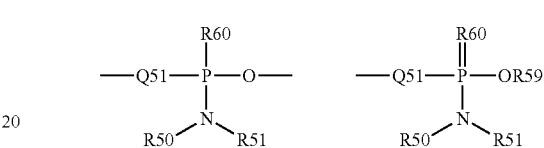

wherein Q51, R50, R51 and R59 are as defined above, and R60 represents a lower alkyl or an aryl.

Analogous substitutions may be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

The definition of each expression, e.g. alkyl, m, n, and the like, when it occurs more than once in any structure, is intended to be independent of its definition elsewhere in the same structure.

The term "selenoalkyl" is art-recognized and refers to an alkyl group having a substituted seleno group attached thereto. Exemplary "selenoethers" which may be substituted on the alkyl are selected from one of —Se-alkyl, —Se-alkenyl, —Se-alkynyl, and —Se—$(CH_2)_m$—R61, m and R61 being defined above.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, and Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*.

Certain compounds of the present invention may exist in particular geometric or stereoisomeric forms. In addition, polymers of the present invention may also be optically active. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

For purposes of this invention, the chemical elements are identified in accordance with the Periodic Table of the Elements, CAS version, *Handbook of Chemistry and Physics*, 67th Ed., 1986-87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and nonaromatic organic compounds that may be substituted or unsubstituted.

The term "protecting group" is art-recognized and refers to temporary substituents that protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed by Greene and Wuts in *Protective Groups in Organic Synthesis* (2$^{nd}$ ed., Wiley: New York, 1991).

The term "hydroxyl-protecting group" is art-recognized and refers to those groups intended to protect a hydrozyl group against undesirable reactions during synthetic procedures and includes, for example, benzyl or other suitable esters or ethers groups known in the art.

The term "carboxyl-protecting group" is art-recognized and refers to those groups intended to protect a carboxylic acid group, such as the C-terminus of an amino acid or peptide or an acidic or hydroxyl azepine ring substituent, against undesirable reactions during synthetic procedures and includes. Examples for protecting groups for carboxyl groups involve, for example, benzyl ester, cyclohexyl ester, 4-nitrobenzyl ester, t-butyl ester, 4-pyridylmethyl ester, and the like.

The term "amino-blocking group" is art-recognized and refers to a group which will prevent an amino group from participating in a reaction carried out on some other functional group, but which can be removed from the amine when desired. Such groups are discussed by in Ch. 7 of Greene and Wuts, cited above, and by Barton, *Protective Groups in Organic Chemistry* ch. 2 (McOmie, ed., Plenum Press, New York, 1973). Examples of suitable groups include acyl protecting groups such as, to illustrate, formyl, dansyl, acetyl, benzoyl, trifluoroacetyl, succinyl, methoxysuccinyl, benzyl and substituted benzyl such as 3,4-dimethoxybenzyl, o-nitrobenzyl, and triphenylmethyl; those of the formula —COOR where R includes such groups as methyl, ethyl, propyl, isopropyl, 2,2,2-trichloroethyl, 1-methyl-1-phenylethyl, isobutyl, t-butyl, t-amyl, vinyl, allyl, phenyl, benzyl, p-nitrobenzyl, o-nitrobenzyl, and 2,4-dichlorobenzyl; acyl groups and substituted acyl such as formyl, acetyl, chloroacetyl, dichloroacetyl, trichloroacetyl, trifluoroacetyl, benzoyl, and p-methoxybenzoyl; and other groups such as methanesulfonyl, p-toluenesulfonyl, p-bromobenzenesulfonyl, p-nitrophenylethyl, and p-toluenesulfonyl-aminocarbonyl. Preferred amino-blocking groups are benzyl (—CH$_2$C$_6$H$_5$), acyl [C(O)R1] or SiR1$_3$ where R1 is C$_1$-C$_4$ alkyl, halomethyl, or 2-halo-substituted-(C$_2$-C$_4$ alkoxy), aromatic urethane protecting groups as, for example, carbonylbenzyloxy (Cbz); and aliphatic urethane protecting groups such as t-butyloxycarbonyl (Boc) or 9-fluorenylmethoxycarbonyl (FMOC).

The definition of each expression, e.g. lower alkyl, m, n, p and the like, when it occurs more than once in any structure, is intended to be independent of its definition elsewhere in the same structure.

The term "electron-withdrawing group" is art-recognized, and refers to the tendency of a substituent to attract valence electrons from neighboring atoms, i.e., the substituent is electronegative with respect to neighboring atoms. A quantification of the level of electron-withdrawing capability is given by the Hammett sigma (σ) constant. This well known constant is described in many references, for instance, March, *Advanced Organic Chemistry* 251-59 (McGraw Hill Book Company: New York, 1977). The Hammett constant values are generally negative for electron donating groups σ(P)=−0.66 for NH$_2$) and positive for electron withdrawing groups σ(P)=0.78 for a nitro group), σ(P) indicating para substitution. Exemplary electron-withdrawing groups include nitro, acyl, formyl, sulfonyl, trifluoromethyl, cyano, chloride, and the like. Exemplary electron-donating groups include amino, methoxy, and the like.

The term "amino acid" is art-recognized and refers to all compounds, whether natural or synthetic, which include both an amino functionality and an acid functionality, including amino acid analogs and derivatives.

The terms "amino acid residue" and "peptide residue" are art-recognized and refer to an amino acid or peptide molecule without the —OH of its carboxyl group.

The term "amino acid residue" further includes analogs, derivatives and congeners of any specific amino acid referred to herein, as well as C-terminal or N-terminal protected amino acid derivatives (e.g. modified with an N-terminal or C-terminal protecting group).

The names of the natural amino acids are abbreviated herein in accordance with the recommendations of IUPAC-IUB.

A "reversed" or "retro" peptide sequence as disclosed herein refers to that part of an overall sequence of covalently-bonded amino acid residues (or analogs or mimetics thereof) wherein the normal carboxyl-to amino direction of peptide bond formation in the amino acid backbone has been reversed such that, reading in the conventional left-to-right direction, the amino portion of the peptide bond precedes (rather than follows) the carbonyl portion. See, generally, Goodman et al. *Accounts of Chem. Res.* 12:423 (1979).

The reversed orientation peptides described herein include (a) those wherein one or more amino-terminal residues are converted to a reversed ("rev") orientation (thus yielding a second "carboxyl terminus" at the left-most portion of the molecule), and (b) those wherein one or more carboxyl-terminal residues are converted to a reversed ("rev") orientation (yielding a second "amino terminus" at the right-most portion of the molecule). A peptide (amide) bond cannot be formed at the interface between a normal orientation residue and a reverse orientation residue.

Therefore, certain reversed peptide compounds of the invention may be formed by utilizing an appropriate amino acid mimetic moiety to link the two adjacent portions of the sequences depicted above utilizing a reversed peptide (reversed amide) bond.

The reversed direction of bonding in such compounds will generally, in addition, require inversion of the enantiomeric configuration of the reversed amino acid residues in order to maintain a spatial orientation of side chains that is similar to that of the non-reversed peptide. The configuration of amino acids in the reversed portion of the peptides is usually (D), and the configuration of the non-reversed portion is usually (L). Opposite or mixed configurations are acceptable when appropriate to optimize a binding activity.

The term "antibody" is art-recognized and intended to include whole antibodies, e.g., of any isotype (IgG, IgA, IgM, IgE, etc.), and includes fragments thereof which are also specifically reactive with a vertebrate, e.g., mammalian protein. Antibodies may be fragmented using conventional techniques and the fragments screened for utility in the same manner as described above for whole antibodies. Thus, the term includes segments of proteolytically-cleaved or recombinantly-prepared portions of an antibody molecule that are capable of selectively reacting with a certain protein. Non-limiting examples of such proteolytic and/or recombinant fragments include Fab, F(ab')2, Fab', Fv, and single chain antibodies (scFv) containing a V[L] and/or V[H] domain joined by a peptide linker. The scFv's may be covalently or non-covalently linked to form antibodies having two or more binding sites. The subject invention includes polyclonal, monoclonal or other purified preparations of antibodies and recombinant antibodies.

The terms "human monoclonal antibodies" and "humanized" murine antibodies, are art-recognized and refer to monoclonal antibodies "humanized" by genetically recombining the nucleotide sequence encoding the a non-human Fv region (i.e., containing the antigen binding site) or the complementarity-determining regions thereof with the nucleotide sequence encoding at least a human constant domain region and an Fc region, e.g., in a manner similar to that fro mouse disclosed in European Patent Application Publication No. 0,411,893 A3. Some additional murine residues may also be retained within the human variable region framework domains to ensure proper target site binding characteristics. In certain embodiments, humanized antibodies may decrease the immunoreactivity of the antibody or polypeptide in the host recipient, permitting an increase in the half-life and a reduction in the possibility of adverse immune reactions.

"Target" is art-recognized and means a site to which a targeted molecule binds. A target may be either in vivo or in vitro. In certain embodiments, a target may be a tumor (e.g., tumors of the brain, lung (small cell and non-small cell), ovary, prostate, breast and colon as well as other carcinomas and sarcomas). In other embodiments, a target may be a site of infection (e.g., by bacteria, viruses (e.g., HIV, herpes, hepatitis) and pathogenic fungi (*Candida* sp.). Certain target infectious organisms include those that are drug resistant (e.g., *Enterobacteriaceae, Enterococcus, Haemophilus influenza, Mycobacterium tuberculosis, Neisseria gonorrhoeae, Plasmodium falciparum, Pseudomonas aeruginosa, Shigella dysenteriae, Staphylococcus aureus, Streptococcus pneumoniae*). In still other embodiments, a target may refer to a molecular structure to which a targeting moiety binds, such as a hapten, epitope, receptor, dsDNA fragment, carbohydrate or enzyme. Additionally, a target may be a type of tissue, e.g., neuronal tissue, intestinal tissue, brain tissue, pancreatic tissue etc.

"Targeting moiety" refers to any molecular structure which assists a molecule in localizing to a particular target area, entering a target cell(s), and/or binding to a target receptor. For example, lipids (including cationic, neutral, and steroidal lipids, virosomes, and liposomes), antibodies, lectins, ligands, sugars, steroids, hormones, nutrients, and proteins may serve as targeting moieties.

The term "bioavailable" is art-recognized and means that a compound the subject invention is in a form that allows for it, or a portion of the amount administered, to be absorbed by, incorporated to, or otherwise physiologically available to a subject or patient to whom it is administered.

The phrase "therapeutically effective amount" is an art-recognized term. In certain embodiments, the term refers to an amount of the therapeutic agent that produces some desired effect at a reasonable benefit/risk ratio applicable to any medical treatment. In certain embodiments, the term refers to that amount necessary or sufficient for diagnostic use of the subject compositions. One of ordinary skill in the art may empirically determine the effective amount of a particular compound without necessitating undue experimentation.

"Small molecule" is art-recognized and refers to a composition which has a molecular weight of less than about 2000 amu, or less than about 1000 amu, and even less than about 500 amu. Small molecules may be, for example, nucleic acids, peptides, polypeptides, peptide nucleic acids, peptidomimetics, carbohydrates, lipids or other organic (carbon containing) or inorganic molecules. Many pharmaceutical companies have extensive libraries of chemical and/or biological mixtures, often fungal, bacterial, or algal extracts, which can be screened with any of the assays of the invention. The term "small organic molecule" refers to a small molecule that is often identified as being an organic or medicinal compound, and does not include molecules that are exclusively nucleic acids, peptides or polypeptides.

The term "modulation" is art-recognized and refers to up regulation (i.e., activation or stimulation), down regulation (i.e., inhibition or suppression) of a response, or the two in combination or apart.

The term "treating" is an art-recognized term which includes curing as well as ameliorating at least one symptom of any condition or disease. Diagnostic applications are also examples of "treating".

A "patient," "subject", or "host" to be treated by the subject method is art-recognized, and means either a human or non-human animal.

The term "mammal" is known in the art, and exemplary mammals include humans, primates, bovines, porcines, canines, felines, and rodents (e.g., mice and rats).

The term "bioavailable" is art-recognized and refers to a form of the subject invention that allows for it, or a portion of the amount administered, to be absorbed by, incorporated to, or otherwise physiologically available to a subject or patient to whom it is administered.

The phrase "pharmaceutically acceptable" is art-recognized. In certain embodiments, the term includes subject compounds, pharmaceutical compositions, fluorescein-based ligands and fluorophores and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" is art-recognized, and includes, for example, pharmaceutically acceptable materials, compositions or vehicles, such as a liquid or solid filler, diluent, excipient, solvent or encapsulating material, involved in carrying or transporting any supplement or composition, or component thereof, from one organ, or portion of the body, to another organ, or portion of the body. Each carrier must be "acceptable" in the sense of being compatible with the other ingredients of the supplement and not injurious to the patient. In certain embodiments, a pharmaceutically acceptable carrier is non-pyrogenic. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "pharmaceutically acceptable salts" is art-recognized, and includes relatively non-toxic, inorganic and organic acid addition salts of compositions of the present invention, including without limitation, therapeutic agents, excipients, other materials and the like. Examples of pharmaceutically acceptable salts include those derived from mineral acids, such as hydrochloric acid and sulfuric acid, and those derived from organic acids, such as ethanesulfonic acid, benzenesulfonic acid, p-toluenesulfonic acid, and the like. Examples of suitable inorganic bases for the formation of salts include the hydroxides, carbonates, and bicarbonates of ammonia, sodium, lithium, potassium, calcium, magnesium, aluminum, zinc and the like. Salts may also be formed with suitable organic bases, including those that are non-toxic and strong enough to form such salts. For purposes of illustration, the class of such organic bases may include mono-, di-, and trialkylamines, such as methylamine, dimethylamine, and triethylamine; mono-, di- or trihydroxyalkylamines such as mono-, di-, and triethanolamine; amino acids, such as arginine and lysine; guanidine; N-methylglucosamine; N-methylglucamine; L-glutamine; N-methylpiperazine; morpholine; ethylenediamine; N-benzylphenethylamine; (trihydroxymethyl)aminoethane; and the like. See, for example, *J. Pharm. Sci.*, 66:1-19 (1977).

The phrases "systemic administration," "administered systemically," "peripheral administration" and "administered peripherally" are art-recognized, and include the administration of a subject composition or other material other than directly into the central nervous system, e.g., by subcutaneous administration, such that it enters the patient's system and, thus, is subject to metabolism and other like processes.

The terms "parenteral administration" and "administered parenterally" are art-recognized and refer to modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intra-articulare, subcapsular, subarachnoid, intraspinal, and intrastemal injection and infusion.

Contemplated equivalents of the compounds described herein include compounds which otherwise correspond thereto, and which have the same general properties thereof (such as other fluorophores, with or without Lewis base(s) for coordinating metal ions, or other cleavable linkers or moieties), wherein one or more simple variations of substituents are made which do not adversely affect the characteristics of the compounds of interest. In general, the compounds of the present invention may be prepared by the methods illustrated in the general reaction schema as, for example, described below, or by modifications thereof, using readily available starting materials, reagents and conventional synthesis procedures. In these reactions, it is also possible to make use of variants which are in themselves known, but are not mentioned here.

General Description of Subject Compounds

A variety of fluorophores, and methods of using and making the same, are contemplated by the present invention and are intended to be included in the subject compounds. Likewise, a number of cleavable linkers and moieties are contemplated by the present invention.

In certain instances, a subject compound contains a fluorophore that is based on fluorescein. The carbon positions of fluorescein are numbered according to the system shown in the figure below. This system is known to those of skill in the art, and will be used to refer to various atoms of the fluorescein molecules in the description, exemplification, and claims below.

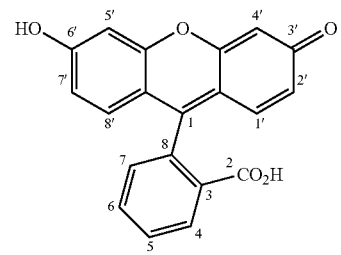

By way of a general, non-limiting description, fluorescein exists in three isomeric forms that are favored under different conditions and may be referred to as different tautomers of fluorescein.

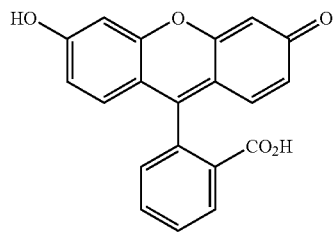

Free acid (red)

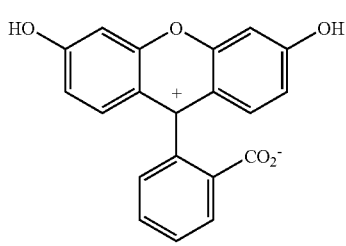

Zwitterion (yellow)

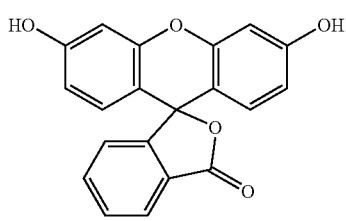

Lactone (colorless)

Fluorophores

A number of fluorophores may be used in the present invention. Some may be used with minimal modification, whereas others may require more substantial modifications, which are usually synthetic in nature. In certain instances, those modifications may involve adding Lewis bases that may serve to coordinate to a metal ion or alternatively adding a cleavable linker or moiety.

Exemplary fluorophores that may be used in the present invention (both as a metal ion ligand and not as a metal ion ligand) include coumarins and related dyes, xanthene dyes such as fluoresceins, rhodols, rhodamines, resorufins, cyanine dyes, bimanes, acridines, isoindoles, dansyl dyes, aminophthalic hydrazides such as luminol and isoluminol derivatives, aminophthalimides, aminonaphthalimides, aminobenzofurans, aminoquinolines, dicyanohydroquinones, and europium and terbium complexes and related compounds. Other potential fluorophores that may be used directly or modified for use in the present invention are known to those of skill in the art.

In one aspect, the present invention is directed to a compound comprising a first fluorophore, a second fluorophore and a cleavable linker covalently linking the first fluorophore and the second fluorophore, wherein the first fluorophore is represented by the following generalized structure:

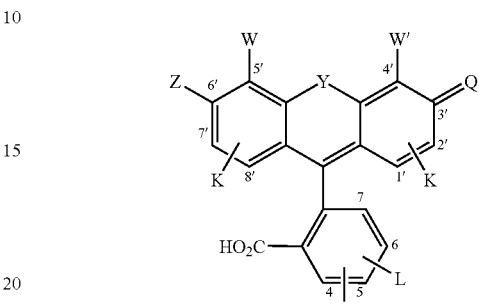

or a tautomer of the generalized structure, wherein, independently for each occurrence:

Y is O, S, Se, NR, or $C(CH_3)_3$, wherein R is an alkyl and R and the methyl groups of $C(CH_3)_2$ are optionally substituted with one or more K's;

Q is O, S or Se;

Z is QH, QU' wherein U' is a hydroxyl-protecting group, or V;

W and W' are each independently hydrogen, K or V;

K is optionally one or more substituents of the indicated moiety other than hydrogen that do not preclude the first fluorophore from fluorescing;

L is the cleavable linker covalently bonded to either the 5 or 6 position of the indicated aromatic ring; and V is a chemical moiety comprising a first Lewis base capable of coordinating to a metal ion, provided that when V occurs in Z and there is an oxygen atom directly bonded to the 6' carbon of the indicated aromatic ring, the Lewis base in V is not that oxygen atom, and wherein one or more fluorescence properties of the first fluorophore change measurably upon coordination of the first Lewis base to a metal ion.

In certain embodiments, the ability of the first fluorophore to bind a type of metal ion of interest will be substantially greater than the binding ability of the second fluorophore to such type of metal ion. It may be the case that the second fluorophore exhibits a change in fluorescent properties upon exposure to the metal ion to which the first fluorophore is capable of binding, which change may be attributable to some association between the metal ion and the second fluorophore (even a binding arrangement). Such a change in the fluoroescent properties of the second fluorophore is contemplated by the present invention, provided it is still possible to deconvulate the emissions spectra of the two fluorophores so that the occurrence of the binding event for the first fluorophore is still measurable. It is even possible that two fluorophores each having different metal ion binding selectivity are included in a subject compound.

In certain embodiments, the binding affinity of the first fluorophore to a type of metal ion will be twice, three times, five, ten, twenty, fifty, hundred or one thousand or more times than the binding affinity of the second fluorophore to the same type of metal ion. In certain embodiments, the change in a fluoroescent property for the first fluorophore upon exposure to a type of metal ion to which it is capable of coordinating will be 25%, 50%, 75%, twice, three times, five, ten, twenty, fifty, hundred or one thousand or more times the change observed in the same fluoroescent property for the second fluorophore upon exposure to the same type of metal ion. These differences between the behavior of the first fluorophore as compared to the second fluorophore may or not be present before the linker is cleaved, and likewise may or may not be present after the linker is cleaved.

In general, V contains a Lewis base fragment that is contemplated to encompass numerous chemical moieties having a variety of structural, chemical and other characteristics capable of forming one or more coordination bonds with a metal ion. The types of functional groups capable of forming coordinate complexes with metal ions are too numerous to categorize here, and are known to those of skill in the art. For example, such moieties will generally include functional groups capable of interaction with a metal center, e.g., heteroatoms such as nitrogen, oxygen, sulfur, and phosphorus.

Figure 1A:
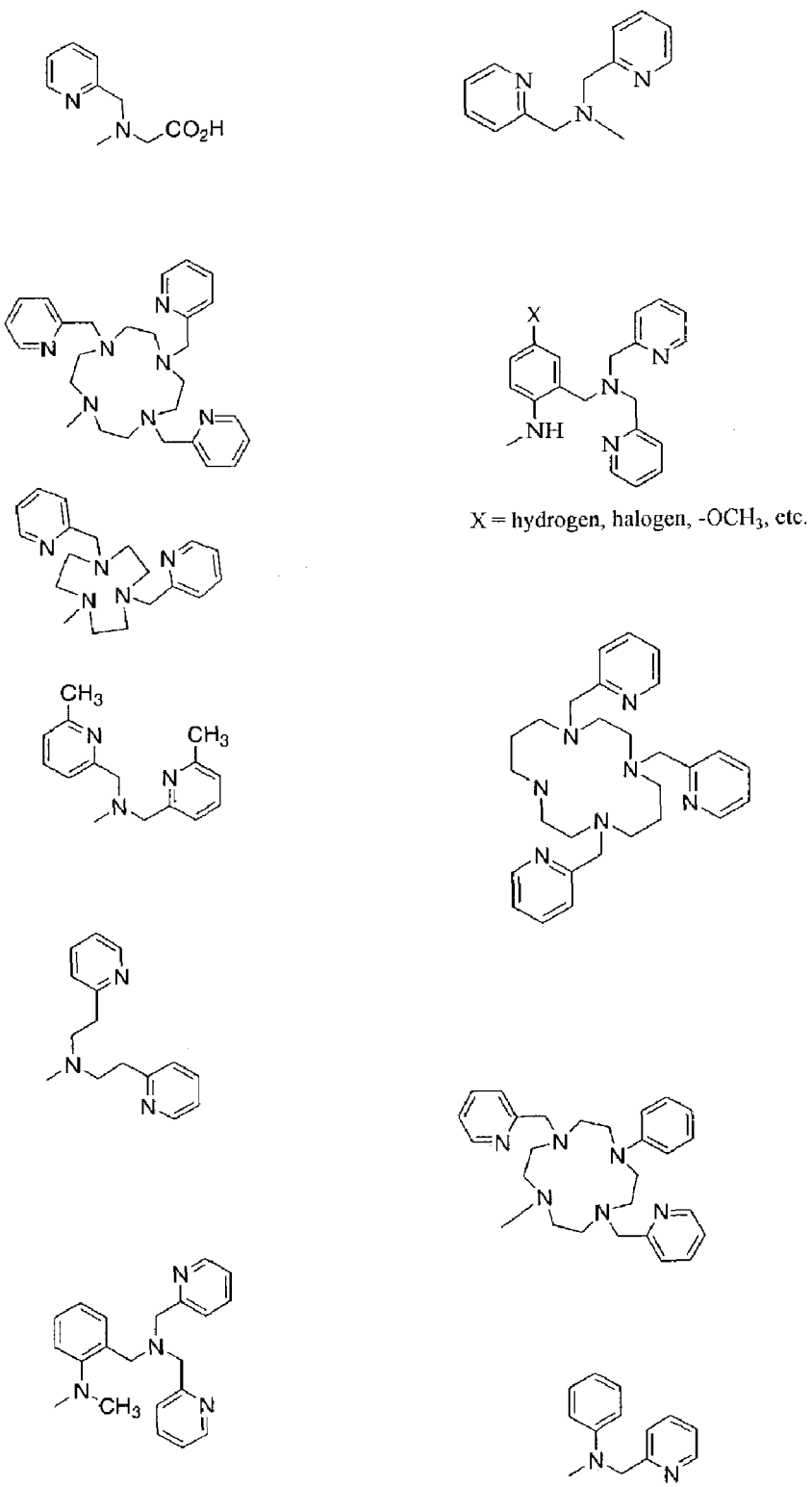
Figure 1B:
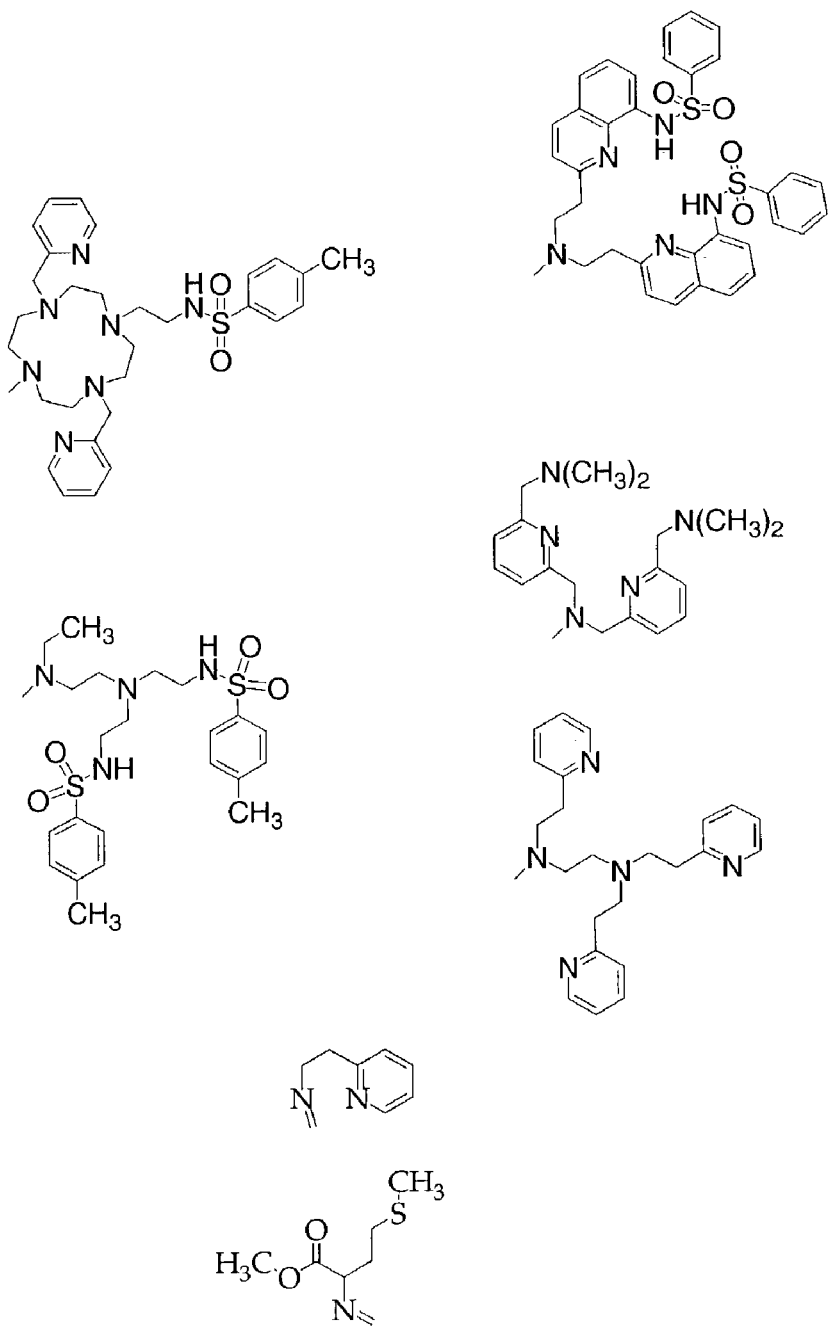
Figure 2:
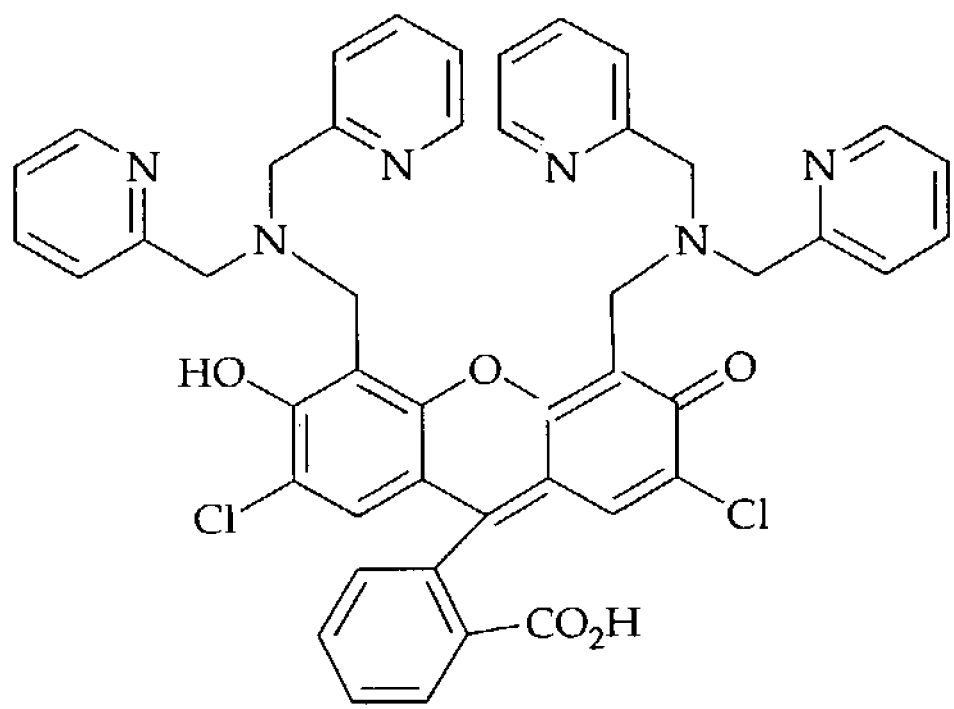
FIG. 2 shows the fluorescein-based ligand of Formula 1.

In certain embodiments, the Lewis base contained in V may involve one of the structures depicted in FIGS. 1A and 1B.

In certain embodiments, V is capable of forming a bidentate chelating agent consisting of an atom of V donating an electron pair and the oxygen atom of the adjacent hydroxyl group(s) of the fluorescein ring structure. Alternatively, V itself includes two or more atoms that serve as Lewis bases and are capable of forming bidentate, tridentate, tetradentate or greater chelating agents by themselves or in conjunction with the oxygen atoms of the hydroxyl substituents of the fluorescein structure. In certain embodiments, the atoms that serve to donate electrons for V are nitrogen, oxygen, sulfur or phosphorus.

Metal cations are almost always Lewis acidic and are therefore able to bind various moieties that may serve as Lewis bases. In general, a moiety serving as a Lewis base will be a strongly acidic group, e.g., with a pKa less than about 7, and more preferably less than 5, which may produce a conjugate base that, under the appropriate conditions, is a strong enough Lewis base to donate an electron pair to a metal ion to form a coordinate bond. The degree of this Lewis acid-to-Lewis base interaction is a function not only of the particular metal ion, but also of the coordinating moiety itself, because the latter may vary in the degree of basicity as well as in size and steric accessibility.

Exemplary Lewis basic moieties which may be included in V include (assuming appropriate modification of them to allow for their incorporation into V and the applicable fluorophore): amines (primary, secondary, and tertiary) and aromatic amines, amino groups, amido groups, nitro groups, nitroso groups, amino alcohols, nitriles, imino groups, isonitriles, cyanates, isocyanates, phosphates, phosphonates, phosphites, phosphines, phosphine oxides, phosphorothioates, phosphoramidates, phosphonamidites, hydroxyls, carbonyls (e.g., carboxyl, ester and formyl groups), aldehydes, ketones, ethers, carbamoyl groups, thiols, sulfides, thiocarbonyls (e.g., thiolcarboxyl, thiolester and thiolformyl groups), thioethers, mercaptans, sulfonic acids, sulfoxides, sulfates, sulfonates, sulfones, sulfonamides, sulfamoyls and sulfinyls.

Illustrative of suitable V include those chemical moieties containing at least one Lewis basic nitrogen, sulfur, phosphorous or oxygen atom or a combination of such nitrogen, sulfur, phosphorous and oxygen atoms. The carbon atoms of such moiety may be part of an aliphatic, cycloaliphatic or aromatic moiety. In addition to the organic Lewis base functionality, such moieties may also contain other atoms and/or groups as substituents, such as alkyl, aryl and halogen substituents.

Further examples of Lewis base functionalities suitable for use in V include the following chemical moieties (assuming appropriate modification of them to allow for their incorporation into V and the subject fluorophore): amines, particularly alkylamines and arylamines, including methylamine, diphenylamine, trimethylamine, triethylamine, N,N-dimethylaniline, methyldiphenylaniline, pyridine, aniline, morpholine, N-methylmorpholine, pyrrolidine, N-methylpyrrolidine, piperidine, N-methylpiperidine, cyclohexylamine, n-butylamine, dimethyloxazoline, imidazole, N-methylimidazole, N,N-dimethylethanolamine, N,N-diethylethanolimine, N,N-dipropylethanolamine, N,N-dibutylethanolamine, N,N-dimethylisopropanolamine, N,N-diethylisopropanolamine, N,N-dipropylisopropanolamine, N,N-dibutylisopropanolamine, N-methyldiethanolamine, N-ethyldiethanolamine, N-propyldiethanolamine, N-butyldiethanolamine, N-methyldiisopropanolamine, N-ethyldiisopropanolamine, N-propyldiisopropanolamine, N-butyldiisopropanolamine, triethylamine, triisopropanolamine, tri-s-butanolamine and the like; amides, such as N,N-dimethylformamide, N,N-dimethylacetamide, N-methylpyrrolidone, hexamethylphosphoric acid triamide and the like; sulfoxide compounds, such as dimethylsulfoxide and the like; ethers such as dimethyl ether, diethyl ether, tetrahydrofuran, dioxane and the like; thioethers such as dimethylsulfide, diethyl thioether, tetrahydrothiophene and the like; esters of phosphoric acid, such as trimethyl phosphate, triethylphosphate, tributyl phosphate and the like; esters of boric acid, such as trimethyl borate and the like; esters of carboxylic acids, such as ethyl acetate, butyl acetate, ethyl benzoate and the like; esters of carbonic acid, such as ethylene carbonate and the like; phosphines including di- and trialkylphosphines, such as tributylphosphine, triethylphosphine, triphenylphosphine, diphenylphosphine and the like; and monohydroxylic and polyhydroxylicalcohols of from 1 to 30 carbon atoms such as methyl alcohol, ethyl alcohol, n-propyl alcohol, isopropyl alcohol, n-butyl alcohol, isobutyl alcohol, tert-butyl alcohol, n-pentyl alcohol, isopentyl alcohol, 2-methyl-1-butyl alcohol, 2-methyl-2-butyl alcohol, n-hexyl alcohol, n-heptyl alcohol, n-octyl alcohol, isooctyl alcohol, 2-ethylhexyl alcohol, n-nonyl alcohol, n-decyl alcohol, 1,5-pentanediol, 1,6-hexanediol, allyl alcohol, crotyl alcohol, 3-hexene-1-ol, citronellol, cyclopentanol, cyclohexanol, salicyl alcohol, benzyl alcohol, phenethyl alcohol, cinnamyl alcohol, and the like; and heterocyclic compounds, including pyridine and the like.

Other suitable structural moieties that may be included in V include the following Lewis base functionalities: arsine, stilbines, thioethers, selenoethers, teluroethers, thioketones, imines, phosphinimine, pyridines, pyrazoles, imidazoles, furans, oxazoles, oxazolines, thiophenes, thiazoles, isoxazoles, isothrazoles, amides, alkoxy, aryoxy, selenol, tellurol, siloxy, pyrazoylborates, carboxylate, acyl, amidates, triflates, thiocarboxylate and the like.

Other suitable ligand fragments for use in V include structural moieties that are bidentate ligands, including diimines, pyridylimines, diamines, imineamines, iminethioether, iminephosphines, bisoxazoline, bisphosphineimines, diphosphines, phosphineamine, salen and other alkoxy imine ligands, amidoamines, imidothioether fragments and alkoxyamide fragments, and combinations of the above ligands.

Still other suitable fragments for use in V include ligand fragments that are tridentate ligands, including 2,5-diiminopyridyl ligands, tripyridyl moieties, triimidazoyl moieties, tris pyrazoyl moieties, and combinations of the above ligands.

Other suitable ligand fragments may consist of amino acids or be formed of oligopeptides and the like.

Because the Lewis basic groups function as the coordination site or sites for the metal cation, in certain embodiments, it may be preferable that the deformability of the electron shells of the Lewis basic groups and the metal cations be approximately similar. Such a relationship often results in a more stable coordination bond. For instance, sulfur groups may be desirable as the Lewis basic groups when the metal cation is a heavy metal. Some examples include the oligopeptides such as glutathione and cysteine, mercapto ethanol amine, dithiothreitol, amines and peptides containing sulfur and the like. Nitrogen containing groups may be employed as the Lewis basic groups when smaller metal ions are the metal. Alternatively, for those applications in which a less stable coordination bond is desired, it may be desirable that the deformability be dissimilar.

In general, K is a chemical moiety that does not preclude using the resulting fluorophore for detection of an analyte of interest, such as a metal ion. K may be any one or more substituents at any of the aromatic ring carbon positions. In general, the 2' and 7' positions of the fluorescein core is more likely to be substituted, whereas the 1' and 8' positions are less likely to be substituted.

In certain embodiments each K, independently, may be a linear or branched alkyl, alkenyl, linear or branched aminoalkyl, linear or branched acylamino, linear or branched acyloxy, linear or branched alkoxycarbonyl, linear or branched alkoxy, linear or branched alkylaryl, linear or branched hyrdoxyalkyl, linear or branched thioalkyl, acyl, amino, hydroxy, thio, aryloxy, arylalkoxy, hydrogen, alkynyl, halogen (e.g., fluro, chloro, bromo), cyano, sulfhydryl, carbamoyl, nitro, trifluoromethyl, amino, thio, lower alkoxy, lower alkylthio, lower alkylamino, nitro, phenoxy, benzyloxy, hydrogen, amine, hydroxyl, alkoxyl, carbonyl, acyl, formyl, sulfonyl and the like.

The identity of K will affect the fluorescence properties of the resulting compound, as known to one of skill in the art. A variety of mechanisms may explain the affect of K on fluorescence, often by quenching, including, for example, double bond torsion, low energy $n\pi^*$ levels, "heavy" atoms, weak bonds, photoinduced electron transfer (PET) and electronic energy transfer (EET). For example, any K substituents having unpaired electrons at the atom directly attached to the aromatic ring, such as an amine or phenol derivative, may in certain instances result in quenching of the fluorescence of the uncomplexed ligand. If, however, upon complexation with a metal ion that atom forms a coordinate bond, then quenching through that mechanism should cease, which would give a greater signal for that particular compound upon binding to the analyte of interest.

Other exemplary subject compounds are set forth in the Figures.

All of these compounds may be prepared by the methods taught herein in conjunction with methods known to those of skill in the art.

Cleavable Linkers and Moieties

In certain embodiments, subject compounds of the present invention contain cleavable linkers or moieties. Generally, a cleavable linker or moiety is a chemical moiety that contains a functionality that may be cleaved when using the subject compound under certain conditions. For example, the cleavable linker of Formula 105 is cleavable when expose to suitable esterases (but not in the absence of any agent that is capable of hydrolyzing the ester functionality in the linker). It is understood that the cleavable linker/moiety should be cleavable under at least some of the conditions during which the subject compound will be used to detect and possible measure the concentration of a metal ion.

In certain instances, the cleavable linker or moiety contains from 1 to 10, 20 30 or 40 carbon atoms. In other instances, the linker may consist mainly of a hydrocarbon chain with functionality at either end to attach to the two fluorophores. Exemplary functional groups that may be used in a linker or moiety include ester, amide, amine, and anhydride moieties.

In many instances, the cleavable linker or moiety is chosen so that it may be cleaved during use of the subject compound. In certain embodiments, cleavage of the linker/moiety will "trap" the cleavage products of the subject compound in a location in vivo, such as within a cell or tissue type or one side or the other of the blood-brain barrier. In certain embodiments of the present invention, the choice of the cleavable linker or moiety may be used to affect how quickly a subject compound localizes in one location, for the cleavage rate may be adjusted by modifying the nature, e.g., the type of functional group or length or steric bulk or hindrance or accessibility, of the linker/moiety.

In certain instances, the cleavable linker or moiety may consist of a chemical moiety that is cleaved by an enzyme, such as a naturally occurring enzyme. For example, the linker/moiety may consist of a peptidyl sequence that is cleaved by a peptidase. In certain embodiments, it may be possible to activate a subject compound in a cell or tissue type of interest during in vivo use by using a cleavable linker/moiety that will be cleaved more readily by activity, often enzymatic, that is specific to, or enhanced in, the target cell or tissue type.

The present invention also contemplates the use of photochemical means to cleave a cleavable linker or moiety. To use light to cleave the linker, it will be necessary to include in the linker/moiety a chemical moiety that is sensitive to light (often at a particular wavelength, e.g., UV). By using light to cleave, it may be possible in certain embodiments to activate the subject compound for metal ion detection at a specific time, by controlling when cleavage occurs, and in a specific location, by only exposing the area of a patient of interest to the cleaving light.

Other cleavable linkers and moieties that may be used in the present invention are readily identified by those of skill in the art.

Exemplary Metal Ions

The metal atom that may form a coordination complex with a subject compound or part thereof or used in the subject methods may be selected from those that have usually at least three, four, five, six, seven coordination sites or more. In certain embodiments, the subject ligands and methods may be used to coordinate a wide range of metal ions, including light metals (Groups IA and IIA of the Periodic Table), transition metals (Groups IB-VIIIB of the Periodic Table), posttransition metals, metals of the lanthanide series and metals of the actinide series. A non-limiting list of metal ions for which the present invention may be employed (including exemplary oxidation states for them) includes: $Li^+$, $Na^+$, $K^+$, $Mg^+$, $Ca^+$, $Zn^{2+}$, $Cd^{2+}$, $Hg^{2+}$, $Cu^{2+}$, $Pd^{2+}$, $Pt^{2+}$.

The design of a subject compound for detecting a particular metal ion will be possible by one of skill in the art, wherein issues such as selectivity, quantum yield, ease of synthesis and the like will be important criteria, Fluorescence Assays Examples of fluorescence assays are set out in the Examples below.

Instrumentation

Fluorescence of a ligand provided by the present invention may be detected by essentially any suitable fluorescence detection device. Such devices are typically comprised of a light source for excitation of the fluorophore and a sensor for detecting emitted light. In addition, fluorescence detection devices typically contain a means for controlling the wavelength of the excitation light and a means for controlling the wavelength of light detected by the sensor. Such means for controlling wavelengths are referred to generically as filters and can include diffraction gratings, dichroic mirrors, or filters. Examples of suitable devices include fluorimeters, spectrofluorimeters and fluorescence microscopes. Many such devices are commercially available from companies such as Hitachi, Nikon or Molecular Dynamics. In certain embodiments, the device is coupled to a signal amplifier and a computer for data processing.

General Aspects

In general, assays using compounds provided by the present invention involve contacting a sample with such a ligand and measuring fluorescence. The presence of a metal ion that interacts with the ligand may alter fluorescence of the ligand in many different ways. Essentially any change in fluorescence caused by the metal may be used to determine the presence of the metal and, optionally the concentration of the metal, in the sample.

The change may take one or more of several forms, including a change in excitation or emission spectra, or a change in the intensity of the fluorescence and/or quantum yield. These changes may be either in the positive or negative direction and may be of a range of magnitudes, which preferably will be detectable as described below.

The excitation spectrum is the wavelengths of light capable of causing the ligand to fluoresce. To determine the excitation spectrum for a ligand in a sample, different wavelengths of light are tested sequentially for their abilities to excite the sample. For each excitation wavelength tested, emitted light is measured. Emitted light may be measured across an interval of wavelengths (for example, from 450 to 700 nm) or emitted light may be measured as a total of all light with wavelengths above a certain threshold (for example, wavelengths greater than 500 nm). A profile is produced of the emitted light produced in response to each tested excitation wavelength, and the point of maximum emitted light can be referred to as the maximum excitation wavelength. A change in this maximum excitation wavelength, or a change in the shape of the profile caused by metal in a sample may be used as the basis for determining the presence, and optionally, the concentration of metal in the sample. Alternatively, the emission spectrum may be determined by examining the spectra of emitted light in response to excitation with a particular wavelength (or interval of wavelengths). A profile of emissions at different wavelengths is created and the wavelength at which emission is maximal is called the maximum emission wavelength. Changes in the maximum emission wavelength or the shape of the profile that are caused by the presence of a metal in a sample may be used to determine the presence or concentration of the metal ion in the sample. Changes in excitation or emission spectra may be measured as ratios of two wavelengths. A range of changes are possible, from about a few nms to 5, 10, 15, 25, 50, 75 100 or more nms.

Quantum yield, $\Phi$, may be obtained by comparison of the integrated area of the corrected emission spectrum of the sample with that of a reference solution. A preferred reference solution is a solution of fluorescein in 0.1 N NaOH, quantum efficiency 0.95. The concentration of the reference is adjusted to match the absorbance, Abs, of the test sample. The quantum yields may be calculated using the following equation:

$$\Phi_{sample} = \Phi_{standard} \times \frac{\int emission_{sample}}{\int emission_{standard}} \times \frac{Abs_{standard}}{Abs_{sample}}$$

A change in quantum yield caused by a metal ion may be used as the basis for detecting the presence of the metal in a sample and may optionally be used to determine the concentration of the metal ion. A range of changes are possible in the subject invention. For example, the difference in the quantum yield for a subject compound in the presence of a metal ion may be about 10%, 25%, 50%, 75% of the quantum yield of the subject compound in the absence of the metal, or it may be 2, 3, 5, 10, 100, 200, 1000, 10000 times greater or more. The same values may be used to describe changes observed in intensity in such the subject assays. Such changes may in certain embodiments depend, for those subject compounds that contain one, cleavage of the cleavable linker.

It is expected that some samples will contain compounds that compete for metal-binding with the fluorescent ligand. In such cases, the fluorescence measurement will reflect this competition. In one variation, the fluorescence may be used to determine the presence or concentration of one or more such metal binding compounds in a sample.

In vitro Assays

In one variation, the presence of a metal ion in a sample is detected by contacting the sample with a subject compound that is sensitive to the presence of the metal, optionally after cleavage of the cleavable linker or moiety. The fluorescence of the solution is then determined using one of the above-described devices, preferably a spectrofluorimeter. Optionally, the fluorescence of the solution may be compared against a set of standard solutions containing known quantities of the metal. Comparison to standards may be used to calculate the concentration of the analyte, i.e. the metal ion.

The metal may be essentially any substance described above. The concentration of the metal may change over time and the fluorescent signal may serve to monitor those changes. For example, the particular form of the metal that interacts with the ligand may be produced or consumed by a reaction occurring in the solution, in which case the fluorescence signal may be used to monitor reaction kinetics.

In certain embodiments, the sample is a biological fluid, lysate, homogenate or extract. The sample may also be an environmental sample such as a water sample, soil sample, soil leachate or sediment sample. The sample may be a biochemical reaction mixture containing at least one protein capable of binding to or altering a metal. Samples may have a pH of about 5, 6, 7, 8, 9, 10, 11, 12 or higher.

In vivo Assays

In another variation, the presence of a metal ion in a biological sample may be determined using a fluorescence microscope and a subject compound. The biological sample is contacted with the fluorescent sensor and fluorescence is visualized using appropriate magnification, excitation wavelengths and emission wavelengths. In order to observe co-localization of multiple analytes, the sample may be contacted with multiple fluorescent molecules simultaneously. In certain embodiments the multiple fluorescent molecules differ in their emission and/or excitation wavelengths.

Biological samples may include bacterial or eukaryotic cells, tissue samples, lysates, or fluids from a living organism. In certain embodiments, the eukaryotic cells are nerve cells, particularly glutamate neurons. In other embodiments, the eukaryotic cells are neurons with mossy fiber terminals isolated from the hippocampus. Tissue samples are preferably sections of the peripheral or central nervous systems, and in particular, sections of the hippocampus containing mossy fiber terminals. It is also anticipated that the detection of a metal in a cell may include detection of the metal in subcellular or extracellular compartments or organelles. Such subcellular organelles and compartments include: Golgi networks and vesicles, pre-synaptic vesicles, lysosomes, vacuoles, nuclei, chromatin, mitochondria, chloroplasts, endoplasmic reticulum, coated vesicles (including clathrin coated vesicles), caveolae, periplasmic space and extracellular matrices.

Assays Using Subject Compounds

In an exemplary assay, the solution or biological sample is contacted with a subject ligand, and fluorescence of the ligand is excited by light with wavelengths ranging from 340 nm to 600 nm. Light emitted by the ligand is detected by detecting light of wavelengths greater than 450 nm.

6. EXEMPLIFICATIONS

The present invention now being generally described, it may be more readily understood from the following examples, which are presented herein for illustration only and should not be construed as limiting the invention.

EXAMPLE ONE

Figure 3:
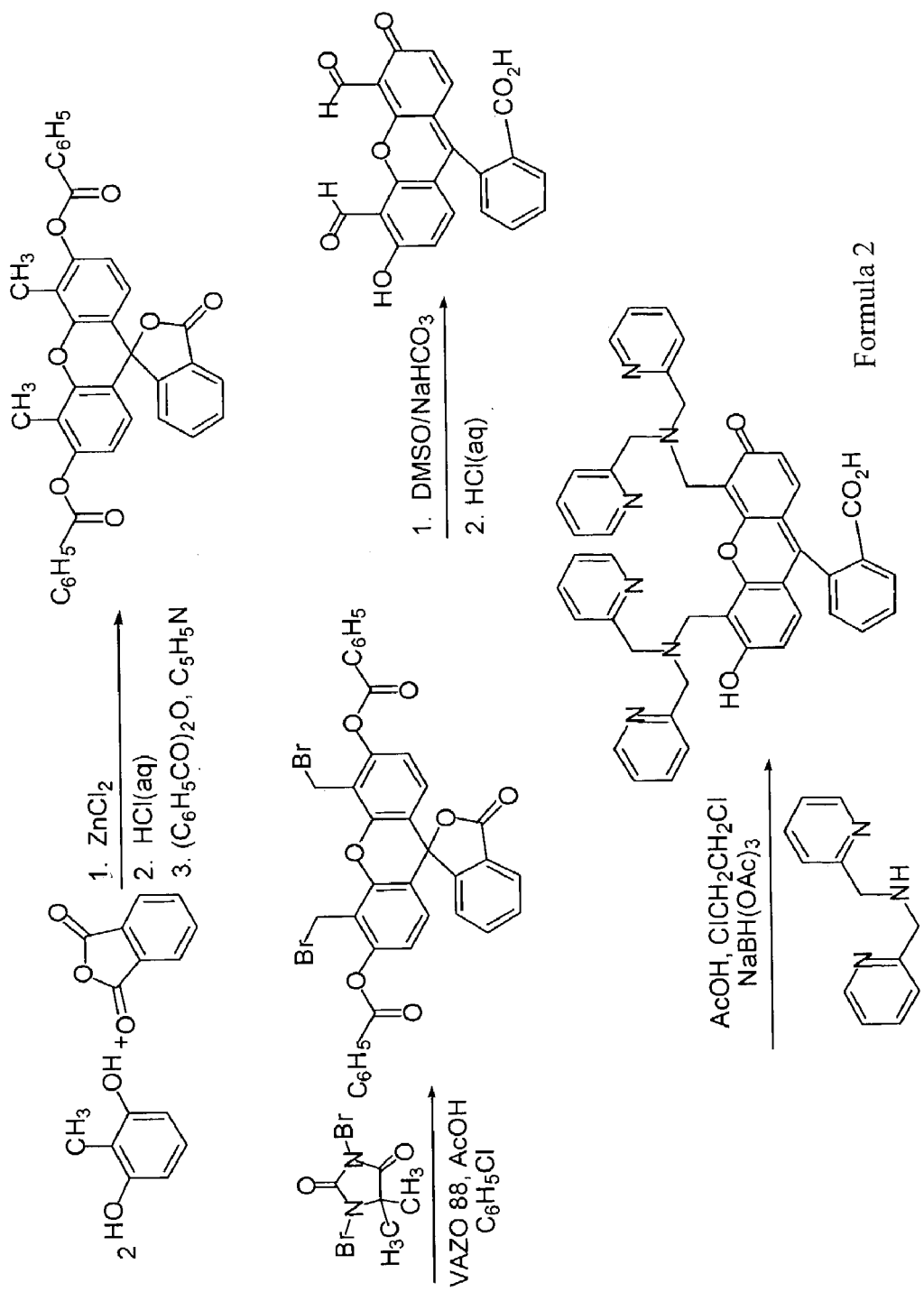
FIG. 3 shows a schematic for the synthesis of a fluorescein-based ligand by derivatization of 4',5'-fluoresceindicarboxaldehyde.

The preparation of a variety of materials is described in this Example One. In certain instances, a person of skill in the art would be able to modify the synthetic protocols described herein to include a cleavable linker or moiety if and when appropriate. Various features of these synthetic pathways are presented in FIGS. 3 and 4.

Unless otherwise indicated, and for this Example One, chlorobenzene ($C_6H_5Cl$) and 1,2-dichloroethane (DCE) are distilled from calcium hydride ($CaH_2$) under nitrogen. Dirmethyl sulfoxide (DMSO) is vacuum distilled from $CaH_2$ and then dried over 3 Å molecular sieves. Deuterated chloroform ($CDCl_3$) is dried over 3 Å molecular sieves. Di(2-picolyl) amine (DPA) is prepared as previously described. All other reagents were purchased and used as received. Flash column chromatography is performed with silica gel-60 (230-400 mesh) or Brockman I activated neutral aluminum oxide (150 mesh). Thin layer chromatography (TLC) analysis is performed with Merck F254 silica gel-60 plates or Merck F254 aluminum oxide-60 and is viewed by UV light, or is developed with ceric ammonium molybdate stain, 2,4-dinitrophenyl hydrazine stain or iodine stain. Infrared spectra are recorded on a BTS 135 FTIR instrument as KBr pellets. NMR spectra are recorded on a Varian 500 MHz spectrometer at ambient probe temperature, 283 K and referenced to the internal $^1H$ and $^{13}C$ solvent peaks. Melting points are recorded on a Thomas Hoover capillary melting point apparatus.

4',5'-Dimethylfluorescein Dibenzoate

The synthesis of 4',5'-dimethylfluorescein dibenzoate was achieved by modification of the published procedure that involves installation of benzoate protecting groups on the phenolic oxygen of 4',5'-dimethylfluorescein. In the initial report, 4',5'-dimethylfluorescein was prepared using benzoyl chloride and characterized only by melting point. Unprotected fluoresceins are highly polar compounds that are only slightly soluble in most common organic solvents. The benzoate protecting groups provide a convenient method for purifying fluorescein compounds by chromatography or crystallization and facilitating subsequent chemical manipulation by enhancing the their solubility in organic media. In addition, protecting the phenolic oxygens forces the fluorescein to adopt the lactoid form preventing isomerization between the quinoid and lactoid forms.

Phthalic anhydride (16.7 g, 113 mmol) and 2-methylresorcinol (24.9 g, 201 mmol) were crushed and melted into a brown liquid at 150° C. Fused $ZnCl_2$ (15 g, 110 mmol) was added slowly over 35 min, and the temperature was slowly increased to 230° C. over 30 min until the material solidified. The brick red solid was crushed into a fine powder and boiled in 250 mL of 6 M HCl for 30 min. The red solid was collected on a frit, washed thoroughly with distilled water and vacuum dried at 50° C. for 2 h. The crude product was combined with benzoic anhydride (115 g, 509 mmol) in 400 mL of pyridine and refluxed at 140° C. for 2.5 h. The reaction mixture was diluted with 700 mL of distilled water, and a dark brown solid formed upon cooling. The solids were collected, washed thoroughly with water, and dried. The dark brown solids were dissolved in 550 mL of boiling toluene and decolorizing carbon was added. The hot mixture was filtered through Celite, and the Celite/carbon was washed with 250 mL of boiling toluene. The product was crystallized from toluene and recrystallized (4:1 toluene/EtOH) to yield a white crystalline solid (32.3 g, 56.7%). TLC $R_f$=0.41 (3:1 hexanes/EtOAc). mp=240-42° C. $^1H$ NMR ($CDCl_3$, 500 MHz) δ 2.42 (6 H, s), 6.76 (2 H, d, J=9.0 Hz), 6.93 (2 H, d, J=8.5 Hz), 7.28 (1 H, d, J=7.5 Hz), 7.55 (4 H, t, J=7.5), 7.65-7.74 (4 H, m), 8.06 (1 H, d, J=8.0 Hz), 8.25 (4 H, d, J=7.5 Hz). $^{13}C$ NMR ($CDCl_3$, 125 MHz) δ 9.85, 82.97, 116.60, 118.09, 119.63, 124.47, 125.39, 125.79, 126.60, 128.91, 129.14, 130.16, 130.48, 134.11, 135.35, 150.44, 150.80, 153.03, 164.74, 169.42. FTIR (KBr, $cm^{-1}$) 1771, 1763, 1738, 1599, 1592, 1452, 1421, 1267, 1222, 1173, 1099, 1024, 899, 870, 712. HRMS (+FAB): Calcd for $M^+$, 569.1600; Found 569.1588.

4',5'-Di(bromomethyl)fluorescein Dibenzoate

4',5'-di(bromomethyl)fluorescein dibenzoate can be formed in multigram quantities by bromination of 4',5'-dimethylfluorescein dibenzoate under free radical conditions. The reaction proceeds under facile conditions to give 4',5'-di(bromomethyl)fluorescein dibenzoate in ~95% purity before crystallization. No dibromination is observed. 4',5'-di(bromomethyl)fluorescein dibenzoate can be carried on without purification to the next step, or recrystallized to give highly pure material (+99%).

4',5'-Dimethyl-fluorescein dibenzoate (5.00 g, 8.79 mmol) and dibromodimethylhydantoin (3.87 g, 13.6 mmol) were combined in 550 mL of $C_6H_5Cl$, and acetic acid (133 µL, 2.32 µmol) and 1,1'-azobis(cyclohexanecarbonitrile (0.181 g, 0.740 mmol) were added to the stirring solution. The solution was stirred at 40° C. for 72 h, and then washed four times with hot water (100 mL, 80° C.). Recrystallization (9:1 toluene/EtOH) and washing with n-pentane yielded the product as a white crystalline solid (6.27 g, 98.2%). TLC $R_f$=0.34 (7:3 hexanes/EtOAc). mp=300° C. dec. $^1H$ NMR ($CDCl_3$, 500 MHz) δ 4.88 (4 H, s), 6.92 (2 H, d, J=8.5 Hz), 7.08 (2 H, d, J=9.0 Hz), 7.32 (1 H, d, J=8.0 Hz), 7.58 (4 H, t, J=7.5 Hz), 7.68-7.78 (4 H, m), 8.08 (1 H, d, J=8.5), 8.28 (4 H, d, J=7.0 Hz). $^{13}C$ NMR ($CDCl_3$, 125 MHz) □ 20.69, 81.60, 117.09, 119.21, 119.38, 124.47, 125.63, 126.36, 128.68, 128.99, 129.10, 130.58, 130.65, 134.50, 135.71, 149.63, 150.79, 152.48, 164.39, 169.04. FTIR(KBr, cm$^{-1}$) 1774, 1743, 1627, 1601, 1589, 1486, 1466, 1451, 1427, 1264, 1234, 1212, 1176, 1143, 1081, 1066, 1023, 913, 763, 707. HRMS (+FAB): Calcd for M$^+$, 724.9811; Found 724.9824.

4',5'-Fluoresceindicarboxaldehyde

Oxidation of 4',5'-di(bromomethyl)fluorescein dibenzoate with DMSO in the presence of NaHCO$_3$ yields the 4',5'-fluoresceindicarboxaldehyde in fairly good yield. Rigorous drying of the DMSO by distillation from CaH$_2$ followed by storage over molecular sieves is required to obtain the product in ~40% yield. Reactions using undistilled DMSO reduce the yields by ~50%. The synthesis of the dialdehyde results in cleavage of the benzoate protecting groups, but H-bonding between the phenolic hydrogens and the aldehyde carbonyl oxygens enforces the lactoid isomer, shown by NMR shift of the phenolic hydrogens ($\delta$=12.2), compensating for the loss of the protecting groups. 4',5'-fluoresceindicarboxaldehyde can be condensed with primary amines to give imines, or aminated under reducing conditions to give amines.

4',5'-Dibromomethylfluorescein dibenzoate (2.00 g, 2.75 mmol) and NaHCO$_3$ (2.00 g, 23.8 mmol) were combined in 200 mL of DMSO and heated to 150° C. for 4 h. The dark red solution was cooled and then diluted into 700 mL of 2 M HCl and stirred for 2 h. The aqueous material was extracted thoroughly with CH$_2$Cl$_2$ (8×100 mL) and the solvents were removed to isolate an orange liquid. The orange solid that precipitated with the addition of 300 mL of water was collected on a frit and washed thoroughly with water. The orange solid was redissolved in CH$_2$Cl$_2$ and dried over Na$_2$SO$_4$. An orange solid was isolated after filtration and solvent removal. Flash chromatography on silica gel (33:1 CHCl$_3$/MeOH) yielded the product as a yellow powder (391 mg, 36.7%). TLC R$_f$=0.46 (19:1 CHCl$_3$/CH$_3$OH). mp=301-303° C. dec. $^1$H NMR (CDCl$_3$, 500 MHz) $\delta$ 6.74 (2 H, d, J=8.5 Hz), 6.94 (2 H, d, J=9.5 Hz), 7.18 (1 H, d, J=7.5 Hz), 7.69 (1 H, td, J=1.0, 7.5 Hz), 7.74 (1 H, td, J=1.0, 7.5, Hz), 8.07 (1 H, d, J=7.5 Hz), 10.67 (2 H, s), 12.13 (2 H, s). $^{13}$C NMR (CDCl$_3$, 125 MHz) $\delta$ 80.80, 109.23, 109.71 115.42, 123.90, 125.76, 126.73, 130.72, 135.86, 137.16, 151.87, 152.11, 164.87, 168.87, 192.00. FTIR (KBr, cm$^{-1}$) 1769, 1656, 1600, 1477, 1433, 1391, 1317, 1288, 1255, 1228, 1172, 1092, 906, 767, 729, 704, 585, 495, 470. HRMS (+FAB): Calcd for M$^+$, 389.0661; Found 389.0674.

Synthesis of a Fluorescein-Based Ligand of Formula 2 from 4'-5'-fluoresceindicarboxyaldehyde A fluorescein-based ligand of the type depicted in Formula 2 (FIG. 3) is prepared with fairly good yield by reaction of 4',5'-fluorescein-dicarboxaldehyde with DPA using NaBH(OAc)$_3$ as the reducing agent.

4',5'-fluorescein-dicarboxaldehyde (200 mg, 0.515 mmol) and acetic acid (120 µL, 2.1 mmol) were combined in 1,2-dichloroethane (DCE, 30 mL) and stirred. To the resulting solution DPA (215 mg, 1.08 mmol) in DCE (20 mL) was added dropwise and stirred for 30 min. Sodium triacetoxyborohydride (230 mg, 1.08 mmol) was added and the reaction mixture was stirred 12 h at room temperature. The reaction was chilled to 0°, and water was added to the stirring solution. The aqueous layer was extracted with CH$_2$Cl$_2$ and the combined organic layers were washed twice with saturated NaCl to give an orange solid after solvent removal. The compound was dried by azeotroping with benzene. Flash chromatography on activated neutral alumina (24:1 CHCl$_3$/MeOH) yielded the product as an orange solid (108 mg, 27.8%). TLC R$_f$=0.10 (alumina, 19:1 CHCl$_3$/CH$_3$OH). mp=195-197° C. dec. $^1$H NMR (CDCl$_3$, 500 MHz) $\delta$ 3.98 (4 H, d, J=15.0 Hz), 4.03 (4 H, d, J=15.0 Hz), 4.18 (4 H, s), 6.57 (2 H, d, J=8.5 Hz), 6.64 (2 H, d, J=8.5 Hz), 7.17-7.21 (5 H, m), 7.37 (4 H, d, J=7.5 Hz), 7.58-7.67 (6 H, m), 8.00 (1 H, d, J=7.5 Hz), 8.59 (4 H, d, J=6.5 Hz). $^{13}$C NMR (CDCl$_3$, 125 MHz) $\delta$ 49.24, 59.45, 109.84, 110.24, 113.38, 122.57, 123.52, 124.38, 125.10, 127.69, 128.30, 129.70, 134.92, 137.16, 149.02, 150.59, 152.86, 158.19, 160.21, 169.64. FTIR (KBr, cm$^{-1}$) 3448, 1755, 1633, 1591, 1489, 1435, 1376, 1253, 1215, 1112, 1081, 760. HRMS (+FAB): Calcd for M$^+$, 755.2982; Found 755.2959.

N,N'-(2-Pyridylethyl)-4',5'-fluoresceincarboxaldimine

To a slurry of 4',5'-fluoresceindicarboxaldehyde (100 mg, 0.258 mmol) in 40 mL of EtOH was added a MeOH solution (0.0827M) of 2-aminoethylpyridine (6.25 mL, 0.517 mmol) over 30 min. The solution immediately changes from yellow to orange, and after stirring for 12 h at 25° C. the product precipitates out of solution. The yellow precipitate was collected on a frit, washed with n-pentane and dried in vacuo to yield the product as a yellow powder (84.1 mg, 54.6%). $^1$H NMR (CDCl$_3$) $\delta$ 3.28 (4 H, t, J=6.5 Hz), 4.20 (4 H, d, J=5.2 Hz), 6.61 (4 H, d, J=9.1 Hz), 7.12-7.27 (5 H, m), 7.65 (4 H, t, J=8.3 Hz), 8.02 (1 H, d, J=6.9 Hz), 8.60 (2 H, d, J=4.5 Hz), 8.87 (2 H, s), 14.78 (2 H, s). FTIR (KBr, cm$^{-1}$) 3423, 3066, 3011, 2935, 2859, 1745, 1645, 1591, 1569, 1534, 1475, 1467, 1437, 1372, 1286, 1260, 1226, 1163, 1114, 1102, 1094, 1052, 1014, 994, 879, 827, 806, 769, 748, 702, 670.

N,N'-(L-Methionine methyl ester)-4',5'-fluoresceincarboxaldimine

L-Methionine methyl ester hydrochloride (76.9 mg, 0.385 mmol) and triethylamine (53.55 µL, 0.385 mmol) were combined in 50 mL of MeOH and stirred overnight. The resulting mixture was added slowly over 1 h to a slurry of 4',5'-fluoresceindicarboxaldehyde (75 mg, 0.193 mmol) in 100 mL of EtOH. Flash chromatography on silica gel (33:1 CHCl$_3$/MeOH) yielded the product as an impure yellow solid. $^1$H NMR (CDCl$_3$) $\delta$ 2.14 (6H, s), 2.2-2.4 (4 H, m), 2.4-2.6 (2 H, m), 2.6-2.8 (2 H, m), 3.82 (6 H, s), 4.4-4.6 (2 H, m), 6.67-6.76 (4 H, m), 7.17 (1 H, d, J=6.8 Hz), 7.63-7.73 (2 H, m), 8.04 (1H, d, J=6.8 Hz), 9.19 (2H, s), 13.9 (2 H, d).

2'-Carboxy-5-chloro-2,4-dihydroxybenzophenone

AlCl$_3$ (40.0 g, 300 mmol) was added to a solution of phthalic anhydride (20.0 g, 135 mmol) and 4-chlororesorcinol (18.8 g, 130 mmol) in 225 ml nitrobenzene and purged with N$_2$. After stirring overnight, the solution was poured into a vigorously stirred biphasic solution of 750 ml hexanes and 1.0 L 0.5 M aqueous HCl. The solution was allowed to stir for 2 h and the light tan precipitate that formed was filtered and washed with 200 ml aqueous 0.1 M HCl and 300 ml hexanes. The crude product was crystallized from hot MeOH/H$_2$O (12.1 g, 32%). $^1$H NMR (CD$_3$OD) $\delta$ 6.48 (1 H, s), 6.95 (1 H, s), 7.39 (1 H, dd, J=7.2 1.5), 7.62-7.52 (2 H, m), 8.12 (1 H, dd, J=1.2, 7.8).

7'-Chloro-4'-methylfluorescein dibenzoate

2'-Carboxy-5-chloro-2,4-dihydroxybenzophenone (10.00 g, 34.1 mmol), 2-methylresorcinol (4.25 g, 34.1 mmol), and ZnCl$_2$ (0.90 g, 6.6 mmol) were ground and melted at 200° C. As the liquid was heated for 50 minutes, it turned into a brick red solid. The solid was cooled to room temperature, ground into a powder and boiled in 200 ml 6 M aqueous HCl for 30 min. The dark red solid was filtered, washed with deionized water, and dried. The crude 7'-chloro-4'-methylfluorescein was dissolved in 125 ml pyridine and benzoic anhydride (30.5 g, 135 mmol) was added. After refluxing for 2.5 h, the orange solution was poured into 250 ml deionized water. Upon cooling a light brown solid formed. The solid was filtered, dissolved in boiling toluene, filtered through activated charcoal, washed with 200 ml hot toluene, and dried. The solid was crystallized from hot toluene/EtOH (10.50 g, 52%). $^1$H NMR (CD$_2$Cl$_2$) δ 2.37 (3 H, s), 6.74 (1 H, d, J=8.7 Hz), 6.94 (1 H, d, J=8.7 Hz), 7.00 (1H, s), 7.30 (1 H, d, J=7.5), 7.53-7.59 (4 H, m), 7.67-7.80 (4 H, m), 8.06 (1H, d, J=7.5 Hz), 8.20-8.24 (4 H, m).

7'-Chloro-4'-bromomethylfluorescein dibenzoate 1,1-Azobis(cyclohexanecarbonitrile) (415 mg, 1.7 mmol) was added to a solution of 7'-chloro-4'-methylfluorescein dibenzoate (10.00 g, 17.0 mmol), 1,3-dibromo-5,5-dimethylhydantoin (4.86 g, 17.0 mmol), and HOAc (300 µl, 5.3 mmol) in 400 ml chlorobenzene. The light yellow solution was heated at 40° C. under N$_2$ for 50 hours and the solvent was removed by rotary evaporation. Light orange crystals of 7'-chloro-4'-bromomethylfluorescein dibenzoate were obtained by crystallization from hot toluene/EtOH (10.72 g, 94%). $^1$H NMR (C$_3$OD) δ 4.80 (2 H, s), 6.90 (1 H, d, J=8.7 Hz), 7.02 (1 H, s), 7.08 (1 H, d, J=8.7 Hz), 7.33 (1 H, d, J=7.5 Hz), 7.51 (1 H, s), 7.54-7.61 (4 H, m), 7.69-7.80 (4 H, m), 8.07 (1 H, d, J=7.2 Hz), 8.22-8.27 (4 H, m).

7'-Chloro-4'-fluoresceincarboxaldehyde

7'-Chloro-4'-bromomethylfluorescein dibenzoate (2.00 g, 3.0 mmol) and NaHCO$_3$ (2.52 g, 30 mmol) in 75 ml DMSO (freshly vacuum distilled from CaH$_2$) was heated to 150° C. for 3 h. The deep red solution was stirred for an additional 1 hr while cooling to 70° C. An orange precipitate formed as the solution was poured into 500 ml 4 M HCl. After stirring overnight, the mixture was extracted with CHCl$_3$ (4×150 ml) and the solvent was removed to leave a dark orange-brown liquid. A light yellow solid precipitated upon addition of 75 ml deionized water. Flash chromatography of the filtered and dried solid on silica gel (33:1 CHCl$_3$/MeOH) yielded a light yellow solid. The light yellow solid was dissolved in hot chlorobenzene on cooling 7'-chloro-4'-fluoresceincarboxaldehyde crystallized (207 mg, 18%). TLC silica (9:1 CHCl$_3$/MeOH) $R_f$=0.57. $^1$H NMR (CD$_2$Cl$_2$) δ 6.06 (1 H, s), 6.65 (1 H, d, J=8.7 Hz), 6.81 (1 H, s), 6.90 (1 H, d, J=8.7), 7.05 (1 H, s), 7.19 (1 H, d, J=7.2 Hz), 7.67-7.70 (2 H, m), 8.03 (1 H, d, J=6.9 Hz), 10.65 (1 H, s), 12.16 (1 H, s).

4',5'-dimethylfluorescein

4',5'-dimethylfluorescein was prepared according to published methods (Burton, H., et al., *J. Soc. Chem. Ind. London* 1948, 67, 345)

2'-7'-Dichlorofluorescein-based Compound (Formula 1)

The synthesis of Formula 1 is accomplished by a Mannich reaction of bis(2-pyridylmethyl)amine (di-picolylamine or DPA), prepared from 2-pyridinecarboxaldehyde and 2-aminomethylpyridine according to published procedures, and 2',7'-dichlorofluorescein (DCF). Formation of the iminum ion from the condensation of paraformaldehyde and DPA and subsequent reaction with DCF yields the desired compound in ~60% yield after trituration with boiling ethanol and washing with cold water. The crude material, which is >90% pure after trituration ($^1$H NMR), can be purified further by chromatography on neutral alumina or reverse phase silica to give analytically pure material (HPLC). This synthesis provides easy access to gram quantities of the desired Zn$^{2+}$ probe.

Although fluorescein undergoes electrophilic substitution preferentially at the 4' and 5' positions, a mixture of structural isomers with substitution at the 4',5',2' and 7' positions is obtained when fluorescein is subjected to the Mannich conditions used to prepare Formula 1. These isomers have proved inseparable by conventional flash chromatography to date.

DPA (1.59 g, 7.99 mmol) and paraformaldehyde (0.224 g, 7.47 mmol) were combined in 20 mL of CH$_3$CN and refluxed for 30 min. 2',7'-Dichlorofluorescein (1.00 g, 2.49 mmol) in 30 mL of CH$_3$CN/H$_2$O (1:1) was added to the solution and the reaction mixture was refluxed for 24 h. The CH$_3$CN was removed and the product and residual water were triturated with 30 mL of boiling ethanol. The product was precipitated at −25° C., filtered on a frit, washed thoroughly with ice cold water and dried. Flash chromatography on activated neutral alumina (45:1 CHCl$_3$/MeOH) yielded the product as a salmon pink solid (960 mg, 46.8%). TLC $R_f$=0.10 (alumina, 19:1 CHCl$_3$/CH$_3$OH). mp=185-187° C. dec. $^1$H NMR (CDCl$_3$, 500 MHz) δ 3.98 (4 H, d, J=15.0 Hz), 4.02 (4 H, d, J=15.0 Hz), 4.20 (4H, s), 6.64 (2 H, s), 7.19 (5 H, t, J=7.5 Hz), 7.36 (4 H, d, J=8.0 Hz), 7.64-7.73 (6H, m), 8.04 (1H, d, J=7.0 Hz), 8.60 (4 H, dq, J=1.0, 5.0 Hz). $^{13}$C NMR (CDCl$_3$, 125 MHz) δ 49.38, 59.31, 89.44, 110.26, 111.93, 117.72, 122.67, 123.43, 124.27, 125.54, 127.28, 127.86, 130.31, 135.41, 137.32, 148.99, 151.83, 156.09, 157.81, 169.13. FTIR (KBr, cm$^{-1}$) 3447, 1761, 1750, 1626, 1592, 1571, 1475, 1435, 1284, 1251, 1214, 1098, 889, 874, 761, 701. HRMS (+FAB): Calcd for M$^+$, 823.2202; Found 823.2229.

2'-Carboxy-5-chloro-2,4-dihydroxybenzophenone

AlCl$_3$ (40.0 g, 300 mmol) was added to a solution of phthalic anhydride (20.0 g, 135 mmol) and 4-chlororesorcinol (18.8 g, 130 mmol) in 225 ml nitrobenzene and purged with N$_2$. After stirring overnight, the solution was poured into a vigorously stirred biphasic solution of 750 ml hexanes and 1.0 L 0.5 M aqueous HCl. The solution was allowed to stir for 2 h and the light tan precipitate that formed was filtered and washed with 200 ml aqueous 0.1 M HCl and 300 ml hexanes. The crude product was crystallized from hot MeOH/H$_2$O (12.1 g, 32%). $^1$H NMR (CD$_3$OD) δ 6.48 (1 H, s), 6.95 (1 H, s), 7.39 (1 H, dd, J=7.2 1.5), 7.62-7.52 (2 H, m), 8.12 (1 H, dd, J=1.2, 7.8).

7'-Chloro-4'-methylfluorescein dibenzoate.

2'-Carboxy-5-chloro-2,4-dihydroxybenzophenone (10.00 g, 34.1 mmol), 2-methylresorcinol (4.25 g, 34.1 mmol), and ZnCl$_2$ (0.90 g, 6.6 mmol) were ground and melted at 200° C. As the liquid was heated for 50 minutes, it turned into a brick red solid. The solid was cooled to room temperature, ground into a powder and boiled in 200 ml 6 M aqueous HCl for 30 min. The dark red solid was filtered, washed with deionized water, and dried. The crude 7'-chloro-4'-methylfluorescein was dissolved in 125 ml pyridine and benzoic anhydride (30.5 g, 135 mmol) was added. After refluxing for 2.5 h, the orange solution was poured into 250 ml deionized water. Upon cooling a light brown solid formed. The solid was filtered, dissolved in boiling toluene, filtered through activated charcoal, washed with 200 ml hot toluene, and dried. The solid was crystallized from hot toluene/EtOH (10.50 g, 52%). $^1$H NMR (CD$_2$Cl$_2$) δ 2.37 (3 H, s), 6.74 (1 H, d, J=8.7 Hz), 6.94 (1 H, d, J=8.7 Hz), 7.00 (1 H, s), 7.30 (1 H, d, J=7.5), 7.53-7.59 (4 H, m), 7.67-7.80 (4 H, m), 8.06 (1H, d, J=7.5 Hz), 8.20-8.24 (4 H, m).

7'-Chloro-4'-bromomethylfluorescein dibenzoate.

1,1-Azobis(cyclohexanecarbonitrile) (415 mg, 1.7 mmol) was added to a solution of 7'-chloro-4'-methylfluorescein dibenzoate (10.00 g, 17.0 mmol), 1,3-dibromo-5,5-dimethylhydantoin (4.86 g, 17.0 mmol), and HOAc (300 µl, 5.3 mmol) in 400 ml chlorobenzene. The light yellow solution was heated at 40° C. under N$_2$ for 50 hours and the solvent was removed by rotary evaporation. Light orange crystals of 7'-chloro-4'-bromomethylfluorescein dibenzoate were obtained by crystallization from hot toluene/EtOH (10.72 g, 94%). $^1$H NMR (CD$_3$OD) δ 4.80 (2 H, s), 6.90 (1 H, d, J=8.7 Hz), 7.02 (1 H, s), 7.08 (1 H, d, J=8.7 Hz), 7.33 (1 H, d, J=7.5 Hz), 7.51 (1 H, s), 7.54-7.61 (4 H, m), 7.69-7.80 (4 H, m), 8.07 (1 H, d, J=7.2 Hz), 8.22-8.27 (4 H, m).

7'-Chloro-4'-fluoresceincarboxaldehyde

7'-Chloro-4'-bromomethylfluorescein dibenzoate (2.00 g, 3.0 mmol) and NaHCO$_3$ (2.52 g, 30 mmol) in 75 ml DMSO (freshly vacuum distilled from $CaH_2$) was heated to 150° C. for 3 h. The deep red solution was stirred for an additional 1 hr while cooling to 70° C. An orange precipitate formed as the solution was poured into 500 ml 4 M HCl. After stirring overnight, the mixture was extracted with $CHCl_3$ (4×150 ml) and the solvent was removed to leave a dark orange-brown liquid. A light yellow solid precipitated upon addition of 75 ml deionized water. Flash chromatography of the filtered and dried solid on silica gel (33:1 $CHCl_3$/MeOH) yielded a light yellow solid. The light yellow solid was dissolved in hot chlorobenzene on cooling 7'-chloro-4'-fluoresceincarboxaldehyde crystallized (207 mg, 18%). TLC silica (9:1 $CHCl_3$/MeOH) $R_f$=0.57. $^1$H NMR ($CD_2Cl_2$) δ 6.06 (1 H, s), 6.65 (1 H, d, J=8.7 Hz), 6.81 (1 H, s), 6.90 (1 H, d, J=8.7), 7.05 (1 H, s), 7.19 (1 H, d, J=7.2 Hz), 7.67-7.70 (2 H, m), 8.03 (1 H, d, J=6.9 Hz), 10.65 (1 H, s), 12.16 (1 H, s).

4-Nitro-3-bromomethylanisole

3-Methyl-4-nitroanisole (41, 2.50 g, 15.0 mmol) and 1,3-dibromo-5,5-dimethylhydantoin (5.00 g, 17.5 mmol) were combined in 250 mL of $C_6H_5Cl$, and acetic acid (75 µL, 1.31 mmol) and 1,1'-azobis(cyclohexanecarbonitrile) (VAZO 88, 150 mg, mmol) were added to the stirring solution. The solution was stirred at 40° C. for 72 h. The crude reaction mixture was washed three times with hot $NaHCO_3$ solution (75 mL, 80° C.), and once with water (75 mL). The organic portion was dried over $MgSO_4$ to give an orange solid after filtration and solvent removal. The solid was filtered through a plug of silica gel to yield a mixture of the brominated product and unbrominated starting material that was carried on to the next step without further purification. Pure material could be obtained from flash chromatography on silica (15:3:2 hexanes/EtOAc/$C_6H_5CH_3$) to give a brown oil (117 mg, 3.19%). TLC $R_f$=0.34 (4:1 hexanes/EtOAc). $^1$H NMR ($CDCl_3$, 500 MHz) δ 3.91 (3 H, s), 4.85 (2 H, s), 6.92 (1 H, dd, J=4.5, 15.0 Hz), 7.02 (1 H, d, J=5.0 Hz), 8.13 (1 H, d, , J=15.5 Hz). ). $^{13}$C NMR ($CDCl_3$, 125 MHz) δ 630.19, 56.25, 114.11, 117.69, 127.61, 128.48, 135.72, 163.45. HRMS (ESI): Calcd for $MH^+$, 245.9766; Found 245.9760.

4-Nitro-3-[bis(2-pyridylmethyl)aminomethyl]-anisole

DPA (950 mg, 4.77 mmol), $K_2CO_3$ (6.50 g, 47.0 mmol), 4-nitro-3-bromomethyl anisole (1.12 g, 4.55 mmol; from a 3.56 g of a mixture containing 3-methyl-4-nitro anisole and 4-nitro-3-bromomethyl anisole, with ~32% 4-nitro-3-bromomethyl anisole), and powdered 3 Å molecular sieves (750 mg) were combined in 20 mL of $CH_3CN$ and stirred for 12 h under Ar. The crude reaction mixture was filtered through celite to give a brown oil after solvent removal. Flash chromatography on basic alumina with a solvent gradient (9:1 $CH_2Cl_2$/EtOAc→4:1 $CH_2Cl_2$/EtOAc→7:3 $CH_2Cl_2$/EtOAc) yielded the product as an orange oil (954 mg, 57.4%). TLC $R_f$=0.32 (3:1 $CH_2Cl_2$/EtOAc). $^1$H NMR ($CDCl_3$, 500 MHz) δ 3.84 (4 H, s), 3.88 (3 H, s), 4.14 (2H, s), 6.77 (1H, dd, J=2.5, 8.5 Hz), 7.13 (2H, td, J=1.5, 5.0 Hz), 7.43 (2 H, d, J=7.5 Hz), 7.50 (1 H, d, J=3.0 Hz), 7.62 (2 H, td, J=2.0, 7.5 Hz), 7.92 (1H, d, J=8.5 Hz), 8.51 (2 H, dq, J=1.0, 5.0 Hz). $^{13}$C NMR ($CDCl_3$, 125 MHz) δ 56.06, 56.40, 112.84, 115.65, 122.32, 123.18, 127.49, 136.68, 138.46, 142.50, 149.20, 158.90, 163.27. HRMS (ESI): Calcd for $MH^+$, 365.1614; Found 365.1608.

3-[Bis(2-pyridylmethyl)aminomethyl]-p-anisidine

Pd/C (1.0 g, 10% activated) and 4-nitro-3-[bis(2-pyridylmethyl)aminomethyl]anisole (914 mg, 2.51 mmol) were combined in 200 mL of MeOH and stirred under a hydrogen atmosphere (1 atm) for 12 h. The reaction mixture was filtered through celite to give a dark yellow oil after solvent removal. Flash chromatography on basic alumina with a solvent gradient (9:1 $CH_2Cl_2$/EtOAc→4:1 $CH_2Cl_2$/EtOAc→7:2:1 $CH_2Cl_2$/EtOAc/MeOH) yielded an impure orange oil. Additional flash chromatography on basic alumina (99:1 $CHCl_3$/MeOH) yielded the product as an orange oil (466 mg, 55.5%). TLC $R_f$=0.82 (4:1 $CH_2Cl_2$/EtOAc). $^1$H NMR ($CDCl_3$, 500 MHz) δ 3.63 (2 H, s), 3.73 (3 H, s), 3.80 (4 H, s), 4.56 (2 H, bs), 6.57 (1 H, d, J=8.5 Hz), 6.64-6.69 (2 H, m), 7.15 (2 H, t, J=5.0 Hz), 7.39 (2 H, d, J=8.0 Hz), 7.62 (2 H, td, J=2.0, 7.5 Hz), 8.55 (2 H, dt, J=1.0, 5.0 Hz). $^{13}$C NMR ($CDCl_3$, 125 MHz) δ 55.96, 58.02, 60.38, 113.94, 116.65, 117.26, 122.23, 123.61, 123.99, 136.54, 140.76, 149.32, 151.97, 159.34. HRMS (ESI): Calcd for $MH^+$, 335.1872; Found 335.1794.

N-(2-[Bis(2-pyridylmethyl)aminomethyl]-4-methoxyphenyl)-2'-chloro-5'-fluoresceincarboxaldimine 2'-Chloro-5'-fluoresceincarboxaldehyde (also known as 7'-Chloro-4'-fluoresceincarboxaldehyde, 38.1 mg, 88 µmol), and 3-[bis(2-pyridylmethyl)aminomethyl]-p-anisidine (32.3 mg, 96 µmol) were combined in 3 mL of EtOAc and stirred for 12 h under Ar. The reaction mixture containing a yellow solid was removed to a −20° C. freezer to further precipitate the product. The yellow precipitate was collected on a frit and washed with cold EtOAc (−25° C.). The product was dissolved in $CHCl_3$/MeOH and washed from the frit to obtain a yellow solid upon solvent removal (41.4 mg, 60.4%). $^1$H NMR ($CDCl_3$, 500 MHz) δ 3.73 (3 H, s), 3.87-3.96 (6 H, m), 6.53-6.61 (3 H, m), 6.76 (1 H, s), 6.87 (1 H, d, J=7.5 Hz), 6.90 (1 H, s), 7.16 (2 H, t, 6.0 Hz), 7.20 (1 H, d, J=7.0 Hz), 7.23 (1H, s), 7.60-7.73 (6 H, m), 8.06 (1 H, d, J=8.0 Hz), 8.49 (2 H, d, J=4.0 Hz), 8.95 (1 H, s). HRMS (ESI): Calcd for $MH^+$, 711.2010; Found 711.2005.

EXAMPLE TWO

Synthesis of Formulas 100-103 (FIG. 5)

In the metal-free form, we have observed that the fluorescence of Formula 1 is largely quenched by the lone pairs of the benzylic amines. Coordination of these amines to $Zn^{2+}$ or to a lesser extent H+affords roughly a 6-fold increase in fluorescence. The dipicolylamine $Zn^{2+}$-binding groups are installed via a Mannich reaction of the parent fluorescein, as described above. Chlorine or other halogen substitution at the 2' and 7' positions is necessary to prevent Mannich reaction at these positions. Mannich reaction of dichlorofluorescein 5- or 6-carboxylate compounds was thus undertaken as a likely route to Formulas 100-103 ligands.

In general, the dichlorofluorescein 5- and 6-carboxylates were synthesized as a mixture by methanesulfonic acid-catalyzed fluorescein condensation of 4-chlororesorcinol with benzene tricarboxylic acid (FIG. 5, top schematic). This reaction affords two isomers, which were protected and separated as the diacetates (FIG. 5, top schematic). Activation of the diacetate with oxalyl chloride and subsequent reaction with ethanol gave the fluorescein ethyl ester diacetates in 65-70% yield (FIG. 5, bottom schematic). The desired dichlorofluorescein 5- or 6-carboxylate products were isolated from Mannich reaction with of dipicolylamine with the corresponding fluorescein diacetates as shown in FIG. 5 (bottom schematic). Successful Mannich reaction of diacyl-protected dichlorofluorescein obviates the intermediate deprotection step.

The yields of the ethyl esters were reproducibly much lower (40%, 44%) than those of the free carboxylates (64%, 73%). The yields of the 6-substituted species were also slightly higher than those of the 5-substituted species. This is consistent with the general trend in the literature that diacylfluorescein 6-carboxylates crystallize more readily than the corresponding 5-carboxylates.

A detailed description of the synthesis for each of the above-described compounds are as follows. For this Example Two and Example Five and Six, reagents are purchased from Aldrich and used without further purification except where otherwise noted. $^1$H and $^{13}$C NMR spectra are acquired on a Varian 300 MHz or a Bruker 400 MHz spectrometer. HRMS spectra are acquired on an FTMS electrospray apparatus by the MIT DCIF facility. Elemental analyses are performed by Complete Analysis Laboratories, Inc. Acetonitrile and dichloromethane are obtained from a dry-still solvent dispensation system.

2',7'-Dichloro-5(6)-carboxyfluorescein

4-Chlororesorcinol (28.8 g, 200 mmol) and 1, 2, 4-benzenetricarboxylic acid (21.0 g, 100 mmol) were combined in 100 mL of methanesulfonic acid and stirred in a 90° C. oil bath for 18 h. The reaction mixture was then poured into 1500 mL of stirred ice water, and the resulting suspension was filtered and washed with $H_2O$. The filtered solid was resuspended in 1 L of $H_2O$, filtered again, and dried under vacuum at 90° C. overnight to give 40.0 g of an orange solid (90% yield). $^1$H NMR (methanol-d$_4$): δ 6.82 (s, 2 H), δ 6.85 (s, 2 H), δ 6.95 (s, 2 H), 6.99 (s, 2 H), δ 7.40 (d, 1 H), δ 7.85 (s, 1 H), δ 8.22 (d, 1 H), δ 8.39 (d, 1 H), δ 8.45 (d, 1 H), δ 8.70 (s, 1 H). The product was carried forward without further purification or characterization.

3',6'-Diacetyl-2',7'-dichloro-6-carboxyfluorescein pyridinium salt

Dichloro-fluorescein 5(6) carboxylic acid (40.0 g, 90 mmol) was stirred in 150 mL of acetic anhydride and 9 mL of pyridine and heated to reflux for 30 min. The reaction was allowed to cool to RT for 4 h, and then filtered. The obtained solid was dried under vacuum to give 16.0 g (30%) of the desired product. $^1$H NMR (CDCl$_3$): δ 11.13 (br s, 2 H); 8.70 (m, 2 H); 8.42 (d, 1 H); 8.14 (d, 1 H); 7.90 (m, 2 H); 7.46 (m, 2 H); 7.17 (s, 2 H); 6.87 (s, 2 H); 2.36 (s, 6 H). $^3$C NMR (CDCl$_3$): 6168.4, 168.3, 152.4, 150.1, 149.0, 147.5, 139.2, 139.1, 132.6, 129.3, 129.1, 126.1, 125.8, 125.2, 123.2, 117.5, 113.3, 21.1, m.p.>300° C. (dec).

3',6'-Diacetyl-2',7'-dichloro-5-carboxyfluorescein

The mother liquor from the 3',6'-Diacetyl-2',7'-dichloro-6-carboxyfluorescein pyridinium salt was diluted with 300 mL of $H_2O$, stirred, and extracted with 3×150 mL of ethyl acetate. The combined organics were washed with 1×100 mL of 3% HCl and 1×100 mL brine, dried over MgSO$_4$, and evaporated to give a light brown solid residue, which was recrystallized twice from $CH_2Cl_2$/EtOAc to give 13.5 g of the desired product (27% yield). $^1$H NMR (CDCl$_3$): δ 8.84 (s, 1 H); 8.49 (d, 1 H); 7.35 (d, 1 H); 7.19 (s, 2 H); 6.89 (s, 2 H); 2.38 (s, 6 H). $^{13}$C NMR (CDCl$_3$): δ 169.7, 169.0, 167.4, 156.3, 149.6, 148.7, 137.3, 132.3, 128.9, 128.1, 126.3, 124.6, 123.0, 116.8, 113.0, 80.8, 66.3, 20.9. m.p. 178-180° C.

3',6'-Diacetyl-2',7'-dichlorofluorescein-6-carboxylate Ethyl Ester

3',6'-Diacetyl-2',7'-dichloro-6-carboxyfluorescein pyridinium salt (1.05 g, 1.7 mmol) was dissolved in 30 mL of dichloromethane and the solution was stirred at 0° C. Dimethylformamide (400 μL) and oxalyl chloride (1.7 mL of a 2 M solution in dichloromethane) were added and the reaction was stirred overnight. Sodium carbonate (180 mg, 1 mmol) and ethanol (10 mL) were added, and stirring was continued for 4 h. The solvents were removed by rotary evaporation and the resulting residue was taken up in $CH_2Cl_2$, filtered through a short plug (2 cm) of silica gel, and crystallized from dichloromethane/ethyl acetate to give 631 mg (67%) off-white crystals. $^1$H NMR (CDCl$_3$): δ 8.38 (d, 1 H); 8.13 (d, 1 H); 7.82 (s, 1 H); 7.17 (s, 2 H); 6.83 (s, 2 H); 4.40 (q, 2 H); 2.38 (s, 6 H); 1.41 (t, 3 H). $^{13}$C NMR (CDCl$_3$): δ 167.92; 167.55; 164.61; 151.91; 149.69; 148.68; 137.55; 132.03; 129.00; 125.83; 125.21; 122.91; 117.00; 113.00; 80.87; 62.41; 20.94; 14.56, m.p. 212-214° C. HRMS(M+H): Calcd 557.0406; found 557.0393.

3',6'-Diacetyl-2',7'-dichlorofluorescein-5-carboxylate Ethyl Ester

3',6'-Diacetyl-2',7'-dichloro-6-carboxyfluorescein (527 mg, 1 mmol) was dissolved in $CH_2Cl_2$ and stirred under nitrogen in a dry ice-acetone bath. DMF (200 μL) was added, and oxalyl chloride (1 mL of a 2 M solution in $CH_2Cl_2$) was added over 20 min. The solution was stirred 12 h, at which time ethanol (10 mL) and NaHCO$_3$ (84 mg, 1 mmol) were added. The reaction was stirred an additional 4 h, then evaporated under reduced pressure, taken up in $CH_2Cl_2$, and filtered through a 2 cm plug of silica gel. Evaporation gave 390 mg of white crystalline residue (70% yield). $^1$H NMR (CDCl$_3$): δ 8.75 (s, 1 H); 8.43 (d, 1 H); 7.32 (d, 1 H); 7.19 (s, 2 H); 6.85 (s, 2 H); 4.44 (q, 2 H); 2.33 (s, 6 H); 1.44 (t, 3 H). $^{13}$C NMR (CDCl$_3$): δ 168.01, 167.82, 164.73, 155.40, 149.75, 148.80, 136.96, 133.68, 129.00, 127.38, 126.31, 124.45, 123.08, 117.08, 113.12, 80.84, 62.32, 21.05, 14.74. HRMS (M+H): Calcd 557.0406, found 557.0401.

(6-CO$_2$H) Ligand (Formula 100)

Dipicolylamine (640 mg, 3.2 mmol) was combined with paraformaldehyde (192 mg, 6.4 mmol) in 20 mL of acetonitrile and heated to reflux for 45 min. 3',6'-Diacetyl-2',7'-dichloro-6-carboxyfluorescein pyridinium salt (304 mg, 0.5 mmol) was dissolved in 10 mL of MeCN was added, followed by 10 mL of $H_2O$, and reflux was continued for 24 h. The resulting suspension was cooled and filtered to yield 360 mg of a light pink powder which was recrystallized from ethanol to give 282 mg (64% overall) after drying overnight at 60° C. under vacuum. The filtrate was acidified with several drops of glacial acetic acid, allowed to stand overnight, and filtered to yield an additional 65 mg (98% crude yield). $^1$H NMR (DMSO-d$_6$): δ 8.55 (d, 4 H); 8.22 (d, 1 H); 8.10 (d, 1 H); 7.77 (m, 5 H); 7.39 (d, 4 H); 7.28 (m, 4 H); 6.63 (s, 2 H); 4.16 (s, 4 H); 4.01 (s, 8 H).; $^{13}$C NMR(DMSO-d$_6$): 167.60, 166.11, 157.41, 155.49, 151.7, 148.69, 148.16, 137.45, 131.27, 129.52, 126.78, 125.65, 124.85, 123.23, 122.64, 116.25, 111.97, 109.36, 82.82, 58.65, 48.86. m.p. 215-218° C. HRMS (M+H): Calcd 867.2095; found 867.2080. Anal: Calcd for $C_{47}H_{36}Cl_2N_6O_7$: C, 65.06; H, 4.18; N, 9.69; Cl, 8.17. Found: C, 64.74; H, 3.96; N, 9.61; Cl, 8.29.

(5-CO$_2$H) Ligand (Formula 101)

3',6'-Diacetyl-2',7'-dichloro-6-carboxyfluorescein (264 mg, 0.5 mmol) was subjected to reaction conditions as for Formula 100. The resulting red solution was acidified with several drops of glacial acetic acid, allowed to stand overnight at 4° C., and filtered to yield 361 mg (83% crude yield) of a dark pink crystalline solid, which gave 318 mg on recrystallization from ethanol (73% overall yield). $^1$H NMR (DMSO-d$_6$): δ 8.53 (d, 4 H); 8.37 (s, 1 H); 8.30 (d, 1 H); 7.77 (td, 4 H); 7.45 (d, 1 H); 7.37 (d, 4 H); 7.28 (m, 4 H); 6.67 (s, 2 H); 4.16 (s, 4 H); 4.00 (s, 8 H); $^{13}$C NMR(DMSO-d$_6$): 167.58, 166.16, 158.37, 155.77, 154.97, 148.69, 149.17, 137.20, 136.49, 133.25, 126.94, 126.15, 124.73, 123.23, 122.68, 116.47, 112.00, 109.25, 82.65, 58.49, 48.81. m.p. 195-195° C. HRMS (M+H): Calcd 867.2095; found 867.2108. Anal: Calcd for $C_{47}H_{36}Cl_2N_6O_7$: C, 65.06; H, 4.18; N, 9.69; Cl, 8.17. Found: C, 64.83; H, 4.02; N, 9.85; Cl, 8.33.

(6-CO$_2$Et) Ligand (Formula 102)

3',6'-Diacetyl-2',7'-dichlorofluorescein-6-carboxylate ethyl ester (264 mg, 0.47 mmol) was subjected to reaction conditions as for Formula 100. The reaction solution was acidified with 5 drops of glacial acetic acid and cooled to −10° C. for 30 h. The resulting salmon-pink precipitate was filtered to give 233 mg (55%) after washing with water and acetonitrile. Recrystallization from ethanol gave 44% yield (185 mg). $^1$H NMR (DMSO-d$_6$): δ 8.63 (d, 4 H); 8.35 (d, 1 H); 8.21 (d, 1 H); 7.90 (s, 1 H); 7.86 (t, 4 H); 7.47 (d, 4 H); 7.37 (m, 4 H); 6.71 (s, 2 H); 4.35 (q, 2 H); 4.25 (s, 4 H); 4.09 (s, 8 H); 1.32 (t, 3 H); m.p. 203-205° C. HRMS(M+H): Calcd 895.2408; found 895.2391. Anal: Calcd for $C_{49}H_{40}Cl_2N_6O_7$: C, 65.70; H, 4.50; N, 9.38; Cl, 7.92. Found: C, 65.63; H, 4.37; N, 9.61; Cl, 8.07.

(5-CO$_2$Et) Ligand (Formula 103)

3',6'-Diacetyl-2',7'-dichlorofluorescein-5-carboxylate ethyl ester (141 mg, 0.25 mmol) was subjected to reaction conditions as for Formula 100. The reaction solution was acidified with 5 drops of glacial acetic acid, concentrated on the rotary evaporator, and the resulting pink residue was taken up in MeCN and filtered to give 113 mg of a pink powder (50%) after washing with water and acetonitrile. Recrystallization of 100 mg from EtOH gave 80 mg of a salmon-pink solid. $^1$H NMR (DMSO-d$_6$): δ 8.54 (d, 4 H); 8.41 (s, 1 H); 8.33 (dd, 1 H); 7.77 (td, 4 H); 7.49 (d, 1 H); 7.38 (d, 4 H); 7.29 (m, 4 H); 6.67 (s, 2 H); 4.39 (q, 2 H); 4.16 (s, 4 H); 4.00 (s, 8 H); 1.37 (t, 3 H). m.p. 178-180° C. HRMS(M+H): Calcd 895.2408; found 895.2406.

EXAMPLE THREE

Physical Properties of Formulas 100-103

The physical properties of the subject compounds prepared as described above were examined. Addition of Zn$^{2+}$ to a 1 μM aqueous solution of each ligand afforded an increase in integrated emission up to 8-fold. Absorption Job plots of the ligand with Zn$^{2+}$ showed break points at both $\chi_L$=0.5 and $\chi_L$=0.67 (where $\chi_L$ is the mole fraction of the ligand), indicating formation of both 1:1 and 1:2 ligand:metal complexes. The dissociation constant for the first binding event was determined using a dual-metal EDTA buffered system as previously described. FIG. 7 depicts the determination of the first dissociation constant for Formulas 100-103. The presence of an electron-withdrawing carboxyl substituent at the 6-position enhanced slightly the $K_d$ relative to Formula 1, but the same substituents at the 5-position decreased the binding affinity significantly (Table 1).

TABLE 1

Physical Constants of Ligands of Formula 1 and Formulas 100-103

| Ligand | $K_{d1}$ Zn$^{2+}$(nM) | pK$_{a1}$ | pK$_{a2}$ | pK$_{a3}$ |
|---|---|---|---|---|
| Formula 103 | ~0.3 | 1.53(2) | 4.02(3) | 6.98(7) |
| Formula 100 | ~0.3 | 1.57(4) | 3.7(4) | 7.05(8) |
| Formula 102 | 0.37 ± 0.04 | 2.1(1) | 4.0(1) | 7.00(4) |
| Formula 100 | 0.16 ± 0.02 | 2.12(1) | 4.07(4) | 7.12(7) |
| Formula 1 | 0.7 ± 0.1 | 2.75 | — | 8.37 |

The presence of a negatively charged carboxylate roughly doubles the binding affinity relative to the ethyl ester. Previous results have indicated that the first binding event is responsible for the large fluorescence increase, and that the dissociation constant for the second binding event of Formula 1 is several orders of magnitude higher than the first.

Quantum yields of the ligands in the bound and free states were examined using a fluorescein standard. All four ligands possess much lower background fluorescence (Φ=0.13-0.21) in the free state compared with the parent B sensor (Φ=0.38). This likely is related to a slight decreased protonation of the benzylic amines, as borne out by pK$_a$ determination discussed below. The brightness of the metal-bound ligands Formulas 100-103 is comparable to that of Formula 1 (Table 2).

TABLE 2

Photochemical Constants of Ligands and Their Zn$^{2+}$ Complexes

| Ligand | λ$_{max}$ (Abs, nm) | λ$_{max}$ (Em, nm) | ε$_{max}$ (M$^{-1}$cm$^{-1}$) | Φ | Brightness |
|---|---|---|---|---|---|
| Formula 103 | 517 | 533 | 66000 | 0.14 | 9.2 × 10$^3$ |
| +Zn$^{2+}$ | 506 | 528 | 71000 | 0.58 | 4.1 × 10$^4$ |
| Formula 101 | 520 | 536 | 81000 | 0.17 | 1.4 × 10$^4$ |
| +Zn$^{2+}$ | 509 | 532 | 88000 | 0.62 | 5.5 × 10$^4$ |
| Formula 102 | 519 | 530 | 61000 | 0.13 | 7.9 × 10$^3$ |
| +Zn$^{2+}$ | 509 | 535 | 72000 | 0.67 | 4.8 × 10$^4$ |
| Formula 100 | 516 | 528 | 76000 | 0.21 | 1.6 × 10$^4$ |
| +Zn$^{2+}$ | 506 | 531 | 81000 | 0.63 | 5.1 × 10$^4$ |
| Formula 1 | 515 | | 79500 | 0.38 | 3.0 × 10$^4$ |
| +Zn$^{2+}$ | 507 | | 84000 | 0.87 | 7.3 × 10$^4$ |

Each ligand undergoes a blueshift in absorbance of ~10 nm on binding Zn$^{2+}$. Extinction coefficients of the Zn$^{2+}$ complex are increased over those of the free fluorophores in all cases, generally by 10-15%. The extinction coefficient for the Zn$^{2+}$ complex of ZinpyrE$_6$-0 was determined at lower concentration, as the Beer's law plot is nonlinear above ~5 μM. This may be due partly or wholly to termolecular complex formation as we have previously observed. The brightness values of the free sensors are significantly reduced in comparison with the Formula 1 ligand, while the brightness values of the Zn$^{2+}$-bound ligands are comparable. Measured values are listed in Table 2.

Protonation constants for the three protonation events (see, e.g. FIG. 6) with an effect on fluorescence were determined by fluorescence titration. The pK$_a$ value at ~7 corresponds to protonation of the benzylic amine responsible for PET quenching of the fluorescence. This pK$_a$ does not vary considerably among the carboxyl-substituted ligands here reported, but is significantly decreased from that of the Formula 1 molecule (pK$_a$=8.4). The decrease in protonation of the benzylic amine at physiological pH results in greatly decreased background fluorescence, offering a plausible explanation for the enhanced fluorescence response discussed above. The pK$_a$ value at 1.5-2.1 represents protonation of the xanthene system, which interrupts conjugation and quenches fluorescence. In this protonation state, the positive charge is delocalized over the xanthene system, but a significant portion resides on the carbon at the 1 position. Thus, an electron-withdrawing substituent para to this carbon (at the 5-position) destabilizes the cation, as is reflected in the significantly lowered pK$_a$ of ZP1 (5-CO$_2$R). pH profiles for Formulas 100-103 are shown in FIG. 8.

The selectivity of metal response was shown to mirror that of the Formula 1 ligand, with alkali and alkali earth metals producing no significant effect on Zn$^{2+}$ response in background levels up to 5 mM. Ca$^{2+}$ produced approximately a 40% increase in fluorescence at 2 mM. Most first-row transition metals quenched fluorescence irreversibly, with the exception of Mn$^{2+}$, which quenched fluorescence reversibly. Cd$^{2+}$ also produced a large fluorescence enhancement, in some cases larger than that of the Zn$^{2+}$ response. Formula 102 afforded the largest fluorescence enhancement in all cases. These data are shown in FIG. 9.

The above results were obtained using the following experimental methods. For all fluorescence experiments, the glassware was washed sequentially with 20% HNO$_3$, deionized water, and ethanol before use. Purified water (resistivity 18.2 Ohms) was obtained from a Millipore Milli-Q water purification system. Fluorophore stock solutions in DMSO were made up to concentrations of 1 mM and kept at 4° C. in 100-500 μL aliquots. Portions were thawed and diluted to the required concentrations immediately prior to each experiment. Fluorescence and absorption data were acquired in HEPES buffer (50 mM, pH 7.5, KCl 100 mM) except where otherwise noted. Solutions were transferred to clean, dry propylene containers for storage, and filtered through 0.25 μm syringe filters before data acquisition. Fluorescence spectra were measured from 475 nm to 650 nm. All measurements were performed in triplicate.

Extinction Coefficients. A 2 mL portion of HEPES buffer was titrated with 2 μL aliquots of 1 mM fluorophore stock solution and the absorption measured at each concentration. The absorbance at the maximum was plotted as a function of concentration, and the slope was taken as the extinction coefficient. The procedure was repeated using 1.9 mL portions of HEPES buffer containing 100 μL aliquots of 10 mM $ZnCl_2$ solution.

Quantum Yields. Quantum yields were calculated by recording UV-vis spectra of the fluorophore under study and a 1 μM fluorescein standard in 0.1 N NaOH to determine the wavelength where sample and fluorescein absorption were equal. The fluorescence spectrum of each was then recorded, exciting at the wavelength determined by uv-vis spectra comparison. The integrated emission of the sample was normalized to the fluorescein standard and multiplied by the standard quantum yield of 0.95. Brannon, J. H.; Magde, D. *J. Phys. Chem.* 1978, 82, 705-709.

Dissociation Constants. Dissociation constants were determined using a dual-metal buffering system as previously described. Solutions containing 1 μM fluorophore, 2 mM $CaCl_2$, 1 mM EDTA, and 0 or 1 mM $ZnCl_2$ were prepared as previously described. Walkup, G. K. et al. *J. Am. Chem. Soc.* 2000, 122, 5644-5645. These solutions were combined so as to give 3 mL aliquots containing 0-0.9 mM $ZnCl_2$, which were allowed to equilibrate at RT for 20 min. Fluorescence spectra were acquired on a Hitachi F-3010 fluorimeter and uv-vis spectra were acquired on a Cary 1E uv-visible spectrophotometer. The fluorescence spectrum of each aliquot was measured and the integrated emission was normalized and plotted as a function of effective free $Zn^{2+}$. The plots were then fit to standard equations using Kaleidagraph for Windows 3.0.

Fluorescence-dependent $pK_a$ determination. $pK_a$ Titrations were performed in 100 mM KCl, 1 mM EDTA. A 1 mM stock solution of fluorophore was diluted with 20 mL of this solution to a final concentration of 1 μM. The pH was brought to 12.5 with 45% w/v KOH, then gradually lowered to pH 2, and the fluorescence spectrum was recorded at each half-unit step in pH. The integrated emission area F was normalized, plotted as a function of pH and fitted to standard equations. Where necessary, individual portions of the plot were fitted as a function of a single $pK_a$ in order to determine suitable initial values.

Metal, ion selectivity. The fluorescence spectrum of a 2 mL aliquot of 1 μM fluorophore excited at 512 nm was acquired by itself, after addition of a 4 μL ($CaCl_2$, $MgCl_2$, 1.00 M) or 10 μL (NaCl 2.00 M, $MnSO_4$, $CoCl_2$, $NiCl_2$, $CuCl_2$, $CdCl_2$ 10 mM) aliquot of metal stock solution, and after addition of a 10 μL aliquot of $ZnCl_2$ (10 mM). The integrated emission of each spectrum was normalized to that of the metal-free control spectrum.

EXAMPLE FOUR

Cell permeability studies using Zn-pyrithione as a membrane-permeant $Zn^{2+}$ complex indicated that Formulas 100 and 101 (the acid-functionalized ligand) are not taken up by the cell. Formulas 102 and 103 (the ester-functionalized ligand), in contrast, were more concentrated in the cell relative to the Formula 1 control (FIGS. 10-13). This result is consistent with intracellular cleavage of the esters to give the substantially membrane-impermeant species Formulas 100 and 101, thereby appearing to trapping effectively the ligand in the cell (FIG. 14). Time-course experiments showed that Formulas 102 and 103 are observed to be retained in the cell, in contrast to Formula 1, which appears to leak out.

EXAMPLE FIVE

Synthesis and Characterization of Formula 104

FIG. 15 depicts the synthesis of a Formula 104 using the above-described general synthetic strategy, with details as follows:

2',7'-Dichloro-5 (6)-Carboxyfluorescein was prepared as described above, as were the 3',6'-Diacetyl-2',7'-dichloro-6-carboxyfluorescein pyridinium salts.

2',7'-Dichloro-6-(2-Hydroxyethyl)fluoresceinamide

3',6'-Diacetyl-2',7'-dichloro-6-carboxyfluorescein pyridinium salt (4.75 g, 9 mmol) was suspended in ethyl acetate (dried over $MgSO_4$) and stirred in an ice bath. Oxalyl chloride (2 M in $CH_2Cl_2$, 5 mL) and DMF (1 mL) were added, and the solution was stirred 16 h. The solvents were removed on the rotary evaporator and the yellow residue was taken up in 25 mL of $CH_2Cl_2$. The resulting solution was stirred in an ice bath and ethanolamine (2.9 mL, 2.87 g, 47 mmol) was added. A red suspension was formed immediately on addition of ethanolamine. The reaction was stirred 2 h at RT, then 30 mL of $H_2O$ were added, the layers separated, and the organic layer extracted with 2×30 mL $H_2O$. The combined aqueous layers were washed with 1×30 mL of $CH_2Cl_2$, acidified with 2 N HCl, and filtered to give an orange solid which was dried in air overnight. Yield 2.04 g, 47%. $^1$H NMR(DMSO-$d_6$): δ 11.08 (br s, 2 H); 8.66 (t, 1 H); 8.18 (d, 1 H); 8.10 (d, 1 H); 7.72 (s, 1 H); 6.95 (s, 2 H); 6.78 (s, 2 H); 3.49 (t, 2 H); 3.17 (m, 2 H). HRMS (M+H): Calcd 488.0298; found 488.0285.

(6-CONH($CH_2$)$_2$OH) Ligand (Formula 104, ZnpyrA-1)

Dipicolylamine (5.12 g, 25.6 mmol) and paraformaldehyde (680 mg, 22.6 mmol) were refluxed together in dry MeCN for 45 min. 2',7'-Dichloro-6-(2-hydroxy-ethyl)fluoresceinamide (1.92 g, 4 mmol) was dissolved in 1:1$H_2O$:MeCN and added, and the reaction was refluxed for 24 h. The reaction was then removed from the heat source, the MeCN was removed on the rotovap, and the resulting solution was left at −25° C. overnight. The resulting precipitate was filtered, washed with $H_2O$, and dried to give 1.35 g (38%) of an orange-pink solid. $^1$H NMR (MeOH-$d_4$): δ 8.50 (d, 4 H); 8.12 (m, 2 H); 7.75 (td, 4 H); 7.64 (s, 1 H); 7.47 (d, 4 H); 7.28 (m, 4 H); 6.71 (s, 2 H); 4.32 (s, 4 H); 4.16 (m, 8 H); 3.66 (t, 2 H); 3.48 (t, 2 H). HRMS (M+H): Calcd 910.2517, found 910.2491.

The response of the Formula 104 ligand to $Zn^{2+}$, the $K_d$ of Formula 104: $Zn^{2+}$ binding, and a fluorescence-dependent $pK_a$ fit were determined as described in Example Three. Representative graphs of these analyses are shown in FIG. 16.

EXAMPLE SIX

Synthesis and Characterization of Formula 105, referred to herein as "Coumazin-1"

FIG. 18 depicts the synthesis of Coumazin-1 (Formula 105), which comprises a Formula 1-based ligand, using the above-described general synthetic strategy involving the Mannich reaction. 2',7'-Dichloro-5 (6)-Carboxyfluorescein was prepared as described above, as were the 3',6'-Diacetyl-2',7'-dichloro-6-carboxyfluorescein pyridinium salts.

3',6'-Diacetyl-2',7'-Dichloro-6-(4-Hydroxybutyl)fluoresceinamide

3',6'-Diacetyl-2',7'-dichloro-6-carboxyfluorescein pyridinium salt (2.44 g, 4 mmol) was dissolved in 40 mL of dry $CH_2Cl_2$ and 800 µL of DMF and stirred under N2 in a dry ice-acetone bath. Oxalyl chloride (4 mL of a 2 M solution in $CH_2Cl_2$) was added over 2 h, and the reaction was stirred overnight. The solvents were then removed by rotary evaporation; the residue was taken up in $CH_2Cl_2$ and $NaHCO_3$ (336 mg, 4 mmol) was added. 4-Aminobutanol (400 µL) was dissolved in $CH_2Cl_2$ and added slowly via addition funnel. The reaction was stirred for 4 h at RT, then washed with 2×40 mL $H_2O$ and 1×50 mL brine, dried over $MgSO_4$ and evaporated. The glassy yellow residue was purified by flash chromatography on silica gel eluting with 98:2→96:4 $CHCl_3$:MeOH, and dried under vacuum to give 650 mg (27%) of a glassy colorless foam.

$^1$H NMR ($CDCl_3$): δ 8.08 (s, 2 H); 7.49 (s, 1 H); 7.14 (br s, 1 H); 7.11 (s, 2 H); 6.85 (s, 2 H); 3.62 (t, 2 H); 3.38 (m, 2 H); 2.38 (s, 6 H); 1.61-1.69 (m, 4 H). $^{13}$C NMR ($CDCl_3$): δ 168.22, 167.78, 165.49, 149.52, 148.58, 142.13, 130.10, 129.01, 127.35, 126.10, 122.97, 122.31, 117.14, 112.95, 80.54, 62.64, 40.54, 30.02, 26.29, 20.95.

3',6'-Diacetyl-2',7'-Dichloro-6-(4-(Coumarin-343-carboxybutyl)fluoresceinamide

3',6'-Diacetyl-2',7'-dichloro-6-(4-hydroxybutyl)fluoresceinamide (600 mg, 1 mmol) was combined with coumarin 343 (290 mg, 1.02 mmol) in dry $CH_2Cl_2$. Triphenyl phosphine (290 mg, 1.11 mmol) and diisopropyl azodicarboxylate (210 µL) were added, and the reaction was stirred at RT for 2.5 h. Most of the solvent was then removed by rotary evaporation, and the residue was diluted with diethyl ether and allowed to stand at RT overnight. The resulting yellow precipitate was filtered and washed with diethyl ether to give 781 mg (90%) of a yellow crystalline powder. $^1$H NMR ($CDCl_3$): δ 8.36 (s, 1 H); 8.26 (d, 1 H); 8.06 (d, 1 H); 7.99 (br t, 1 H); 7.78 (s, 1 H); 7.09 (s, 2 H); 6.95 (s, 1 H); 6.85 (s, 2 H); 4.30 (br s, 2 H); 3.50 (br t, 2 H); 3.36 (br s, 4 H); 2.74-2.86 (m, 4 H); 2.34 (s, 6 H); 1.98 (br s, 4 H); 1.83 (br s, 4 H). HRMS(M−H): Calcd 865.1562, found 865.1561.

Coumazin-1 (Formula 105)

Dipicolylamine (320 mg, 1.6 mmol) and paraformaldehyde (96 mg, 3.2 mmol) were combined in 20 mL of MeCN and heated to reflux for 45 min. 3',6'-Diacetyl-2',7'-Dichloro-6-(4-(Coumarin-343-carboxybutyl)fluoresceinamide (217 mg, 0.25 mmol) was suspended in 10 mL of MeCN and added to the refluxing solution, and 10 mL of $H_2O$ was then added. The reaction was removed from heat after 24 h, and the solvents were removed. Several drops of glacial acetic acid were added, followed by $H_2O$ and a red precipitate formed which was filtered to give 120 mg of the crude product. The filtrate was allowed to stand for 48 h at RT and then filtered to afford 54 mg additional product. $^1$H NMR ($CDCl_3$): δ 8.57 (d, 4 H); 8.39 (s, 1 H); 8.20 (d, 1 H); 8.02 (d, 1 H); 7.86 (br t, 1 H); 7.77 (s, 1 H); 7.64 (m, 4 H); 7.33 (d, 4 H); 7.17 (m, 4 H); 6.96 (s, 1 H); 6.62 (s, 2 H); 4.31 (br s, 2 H); 4.17 (s, 4 H); 4.00 (s, 8 H); 3.48 (br s, 2 H); 3.35 (br s, 4 H); 2.87 (t, 2 H); 2.76 (t, 2 H); 1.97 (br m, 4 H); 1.83 (br m, 4 H). HRMS(M+H): Calcd 1205.3726, found 1205.3770.

Coumazin-1 was subjected to esterase treatment for 16 hours in order to cleave it into its constituent fluorophores (FIG. 19). As discussed above, excitation of the coumarin fluorophore at 445 nm and measurement of emission at 488 nm yields information about the amount of sensor present, while excitation of the fluorescein-based fluorophore at 505 nm and measurement of emission at 535 nm affords information about the amount of $Zn^{2+}$ present. After esterase treatment, in the absence of zinc, little emission was observed for either fluorophore. Upon adding zinc, little emission was observed at 488 mm when the sample was excited at 445 nm, whereas an increase in emission at 535 nm was observed when the sample was excited at 505 nm, indicating that the metal-binding fluorophore was functional.

Further, the measurement of zinc levels by Coumazin-1 was observed to be ratiometric. As $ZnCl_2$ is titrated into an esterase-treated solution of Coumazin-1 in HEPES buffer (pH 7.5), the ratio of emission intensity at 534 nm (exc 505 nm) to 488 nm (exc 445 nm) increases from 0.5 to 4.1 (FIG. 20).

Table 3 compares the physical characteristics of the ligands of Formula 1, 104, and 105, determined as described in the above Examples.

TABLE 3

| Ligand | Φ | Φ ($Zn^{2+}$) | $K_d$ (nM) | $pK_a$ |
|---|---|---|---|---|
| Formula 1 | 0.38 | 0.87 | 0.7 ± 0.1 | 8.37 |
| Formula 104 | 0.21 | 0.64 | 0.20 ± 0.02 | 8.43 |
| Formula 105 | 0.01[a,b] | 002[a], 0.04[b] | — | — |

[a]excited in the coumarin absorption region,
[b]excited in the fluorescein absorption region.

EXAMPLE SEVEN

The synthesis of a subject ligand is outlined in FIG. 21. Dialkylation of m-anisidine (26) with picolyl chloride affords N,N-bis(2-pyridylmethyl)-m-anisidine (27) in fair yield. Subsequent removal of the methyl protecting group with boron tribromide ($BBr_3$) provides N,N-bis(2-pyridylmethyl)-3-aminophenol (28), one of the required fragments for the synthesis of compound 30. A variety of reagents was screened to catalyze the condensation of 28 with 2'-carboxy-5-chloro-2,4-dihydroxybenzophenone (29) to yield compound 30. Reactions in THF (200° C., sealed vessel) using $ZnCl_2$ and $AlCl_3$ failed to yield the desired product. Compound 30 was successfully isolated from the reaction of 28 and 29 in neat methane sulfonic acid ($CH_3SO_3H$). It is also possible to condense 27 directly with 29 in trifluoroacetic acid to give 30 without first deprotecting 27 to give 28. It is anticipated that this reaction will be used to prepare other subject ligands. The affinity of compound 30 for $Zn^{2+}$ was found to be weak.

For this Example Seven, dichloromethane ($CH_2Cl_2$), 1,2-dichloroethane (DCE) and chlorobenzene ($C_6H_5Cl$) are distilled from calcium hydride ($CaH_2$) under nitrogen. Acetonitrile ($CH_5CN$) is distilled from $CaH_2$ under nitrogen and dried over 3 Å molecular sieves. Nitrobenzene ($C_6H_5NO_2$), dimethylformamide (DMF), and ethyl acetate (EtOAc) is dried over 3 Å molecular sieves. Deuterated chloroform ($CDCl_3$) is dried over 3 Å molecular sieves. Di(2-picolyl)amine (DPA), 2'-carboxy-5-chloro-2,4-dihydroxybenzophenone (29), and are prepared as previously described. All other reagents are purchased and used as received. Flash column chromatography is performed with silica gel-60 (230-400 mesh) or Brockman I activated basic aluminum oxide (150 mesh). Thin layer chromatographic (TLC) analysis is performed with Merck F254 silica gel-60 plates or Merck F254 aluminum oxide-60 and is viewed by UV light, or is developed with ceric ammonium molybdate, ninhydrin or iodine stain. NMR spectra are recorded on a Varian 500 MHz spectrometer at ambient probe temperature, 283 K, and referenced to the internal $^1$H and $^{13}$C solvent peaks. Electrospray ionization (ESI), and electron impact (EI) mass spectrometry are performed in the MIT Department of Chemistry Instrumentation Facility using m-nitrobenzyl alcohol as the matrix.

N,N-Bis(2-pyridylmethyl)-m-anisidine (27)

Picolylchloride hydrochloride (12.0 g, 73.4 mmol) was dissolved in 3 mL of water, and 18 mL of 5 N NaOH was added to give a pink solution. An additional 18 mL of 5 N NaOH was added to the vigorously stirring solution, after m-anisidine (1.8 mL, 16.0 mmol) was combined with the solution of picolylchloride. An aliquot of cetyltrimethylammonium chloride (250 µL, 25 wt. % in water) was added as a phase transfer catalyst (PTC), and the reaction was stirred vigorously under Ar. Additional picolylchloride hydrochloride (5.6 g, mmol) was added to the solution after 48 h, and after 144 h, an additional portion of picolylchloride hydrochloride (10.0 g, mmol) and 15 mL of 5 N NaOH. After a total reaction time of 11 days, the product was extracted into $CH_2Cl_2$, and dried over $MgSO_4$, to give a brown solid after solvent removal. Flash chromotography on basic alumina with solvent gradient (24:1→4:1 $CH_2Cl_2$/EtOAc) yielded the product as a yellow solid (1.72 g, 35.2%). TLC $R_f$=0.33 (4:1 $CH_2Cl_2$/EtOAc). $^1H$ NMR ($CDCl_3$, 500 MHz) δ 3.69 (3 H, s), 4.85 (4H, s), 6.27 (1H, t, J=2.5 Hz), 6.30 (2 H, tt, J=2.0, 7.5 Hz), 7.08 (1 H, t, J=8.0 Hz), 7.17 (2 H, t, J=5.0 Hz), 7.31 (2 H, d, J=7.5 Hz), 7.67 (2 H, t, J=7.5 Hz), 8.61 (2 H, dd, J=1.0, 5.0 Hz). $^{13}C$ NMR ($CDCl_3$, 125 MHz) δ 55.23, 57.5, 99.26, 102.29, 105.75, 120.94, 122.20, 130.19, 137.01, 148.88, 158.93, 160.94. HRMS (ESI): Calcd for MH$^+$, 306.1606; Found 306.1606.

N,N-Bis(2-pyridylmethyl)-3-aminophenol (28)

A solution of N,N-Bis(2-pyridylmethyl)-m-anisidine (27, 500 mg, 1.64 mmol) in 20 mL of $CH_2Cl_2$ was frozen with liquid $N_2$, and 50 mL of 1.0 M $BBr_3$ (50 mmol) in $CH_2Cl_2$ was added via a cannula. The solution was allowed to slowly warm to room temperature, and stirred under Ar for 40 h. The reaction mixture was chilled to 40° C. via an isopropanol/dry ice bath, and MeOH was added slowly to quench the excess $BBr_3$. The quenched reaction mixture was diluted with ~300 mL of water and boiled for 45 min. After the aqueous solution was cooled, neutralized to pH ~6.5 with saturated $NaHCO_3$, and saturated with KCl, the product was extracted into $CH_2Cl_2$ to give a red solid after solvent removal. Flash chromotography on basic alumina (4:1 $CH_2Cl_2$/EtOAc) yielded the product as a yellow solid (190 mg, 39.8%). TLC $R_f$=0.27 (17:3 $CH_2Cl_2$/EtOAc). $^1H$ NMR ($CDCl_3$, 500 MHz) δ 4.81 (4H, s), 6.12 (1H, t, J=2.0 Hz), 6.23 (1 H, dd, J=2.5, 8.0 Hz), 6.30 (1 H, dd, J=2.0, 8.0 Hz), 7.04 (1 H, t, J=8.0 Hz), 7.11 (2 H, t, J=5.0 Hz), 7.29 (2 H, d, J=8.0 Hz), 7.64 (2 H, td, J=1.5, 7.5 Hz), 8.34 (2H, d, J=4.5 Hz). $^{13}C$ NMR ($CDCl_3$, 125 MHz) δ 57.28, 99.74, 104.26, 105.56, 121.19, 122.45, 130.69, 137.61, 149.06, 149.36, 158.56, 158.88. HRMS (ESI): Calcd for MH$^+$, 292.1450; Found 292.1444.

9-(o-Carboxyphenyl)-2-chloro-6-[bis(2-pyridylmethyl) amino]-3-xanthanone (30)

N,N-Bis(2-pyridylmethyl)-3-aminophenol (28, 300 mg, 1.03 mmol) and 2'-carboxy-5-chloro-2,4-dihydroxybenzophenone (29, 295 mg, 1.01 mmol) were combined in 5 mL of methane sulfonic acid ($CH_3SO_3H$). The resulting dark red solution was stirred for 48 hrs at 70° C. The reaction mixture was diluted with 250 mL of water, chilled to 0° C., and slowly neutralized with saturated $NaHCO_3$. The aqueous mixture was extracted thoroughly with $CH_2Cl_2$, and the combined organic extracts were dried over $MgSO_4$ to give a red solid after filtration and solvent removal. Flash chromatography on silica (93:7 $CHCl_3$/MeOH) yielded the product as a red solid (322 mg, 57. 1%). TLC $R_f$=0.47 (9:1 $CHCl_3$/MeOH). $^1H$ NMR ($CDCl_3$, 500 MHz) δ 4.84 (4 H, s), 6.43 (2 H, d, J=10.5 Hz), 6.56 (1 H, d, J=8.5 Hz), 6.73 (2 H, s), 7.14-7.24 (5 H, m), 7.56-7.69 (4 H, m), 8.02 (1 H, d, J=7.5 Hz), 8.54 (2 H, d, J=5.0 Hz). $^{13}C$ NMR ($CDCl_3$, 125 MHz) δ 19.86, 21.46, 56.57, 98.94, 103.81, 109.70, 111.85, 121.25, 122.88, 125.87, 126.11, 128.23, 128.78, 128.99, 129.41, 129.66, 129.93, 129.99, 134.20, 137.98, 149.35, 153.01, 157.20, 169.35. HRMS (ESI): Calcd for MH$^+$, 548.1377; Found 548.1372.

9-(o-Carboxyphenyl)-2-chloro-6-[bis(2-pyridylmethyl) amino]-3-xanthanone (30)

A mixture of N,N-di(pyridylmethyl)-m-anisidine (6 mg, 0.02 mmol) (27) and 2-carboxy-3'-chloro-4',6'-dihydroxybenzophenone (29) (9 mg, 0.03 mmol) in trifluoroacetic acid (0.5 mL) was stirred at 60 degrees C. for 12 h. Solvent was then removed by evaporation and residue chromatographed on silica gel using 10:1 ethyl acetate/methanol as eluent. This resulted in isolation of 20 mg of a fluorescent product which appeared to be a mixture of trifluoroacetate salts of the desired product. The material was therefore taken up in aqueous sodium carbonate which was then adjusted to pH 8. Extraction with chloroform and evaporation of the combined organic layers resulted in 11 mg of the desired product. The $^1H$ NMR of this material corresponds well to an authentic sample, with small additional impurity peaks. The electrospray mass spectrogram shows the expected molecular ion as well as expected fragment peaks.

9-(o-Carboxyphenyl)-2-chloro-6-[(2-pyridylmethyl) amino]-3-xanthanone

N,N-Bis(2-pyridylmethyl)-3-amino-4-methylphenol (2, 284 mg, 0.93 mmol) and 2'-carboxy-5-chloro-2,4-dihydroxybenzophenone (3, 272 mg, 0.93 mmol) were combined in 5 mL of methane sulfonic acid ($CH_3SO_3H$). The resulting dark red solution was stirred for 48 hrs at 70° C. The reaction mixture was diluted with 250 mL of water, chilled to 0° C., and slowly neutralized with saturated $NaHCO_3$. The aqueous mixture was extracted thoroughly with $CH_2Cl_2$, and the combined organic extracts were dried over $MgSO_4$ to give a red solid after filtration and solvent removal. Flash chromatography on silica (9:1 $CHCl_3$/MeOH) yielded the product as a red solid (149 mg, 34.1%). TLC $R_f$=0.15 (9:1 $CHCl_3$/MeOH). $^1H$ NMR ($CDCl_3$, 500 MHz) δ 2.09 (3 H, s), 4.50 (2 H, s), 6.34 (1 H, s) 6.47 (1 H, s), 6.78 (2 H, s), 7.18 (1 H, d, J=7.5 Hz), 7.27 (2 H, m), 7.33 (1 H, d, J=7.0 Hz), 7.64-7.72 (3 H, m), 8.10 (1 H, d, J=8.0 Hz), 8.61 (1 H, d, J=4.5 Hz). HRMS (ESI): Calcd for MH$^+$, 471.1112; Found 471.1219.

EXAMPLE EIGHT

Fluorescein-based Ligands

For this Example Eight, the following general experimental procedures are used. Silica gel-60 (230-400 mesh), Brockman I activated basic aluminum oxide (150 mesh), and octadecyl-functionalized silica gel (RPC 18) are used as the solid phases for flash chromatography. Thin layer chromatography (TLC) was performed using Merck F254 silica gel-60 plates, Merck F254 aluminum oxide-60 plates, or octadecyl-functionalized silica gel (RP 18) plates. TLC plates are viewed with UV light or are developed with 12 or ninhydrin stain when appropriate. Preparative TLC is performed using PLKSF silica gel plates with a thickness of 1000 µm purchased from Whatman Ltd. NMR spectra are obtained using either a Varian 300 MHz or a Bruker 400 MHz spectrometer operating at ambient probe temperature, 283 K, and referenced to an internal probe standard for $^1H$ and $^{13}C$ NMR. An external $CFCl_3$ reference was used for $^{19}F$ NMR. IR spectra are obtained using an Avatar 360 FTIR instrument operating under the manufacturer-supplied software. Electron impact (EI) and electrospray ionization (ESI) spectroscopy are performed in the MIT Department of Chemistry Instrumentation Facility.

2'-Carboxy-2,4-dihydroxybenzophenone

2'-Carboxy-2,4-dihydroxybenzophenone was prepared according to literature procedures. Smith, G. A.; Metcalfe, J. C.; Clarke, S. D *J. Chem. Soc. Perkin Trans* 2. 1993, 1195. $AlCl_3$ (28.00 g, 210 mmol) was added to a solution of phthalic anhydride (13.85 g, 93.5 mmol) and resorcinol (10.0 g, 90.8 mmol) in 225 ml nitrobenzene and purged with $N_2$. After stirring overnight, the solution was poured into a vigorously stirred biphasic solution of 750 ml hexanes and 1.0 L 0.5 M aqueous HCl. The solution was allowed to stir for 2 h and the light tan precipitate that formed was filtered and washed with 200 ml aqueous 0.1 M HCl and 200 ml hexanes. The crude material was crystallized as light green plates from hot MeOH/$H_2O$ (9.90 g, 42%). $^1$H NMR (acetone-$d_6$) δ 6.33 (1H, dd, J=9.0, 2.3 Hz), 6.39 (1H, d, J=2.3 Hz), 7.00 (1 H, d, J=9.0 Hz), 7.45 (1 H, d, J=7.5 Hz), 7.65-7.80 (2 H, m), 8.12 (1 H, d, J=6.7 Hz). FTIR (KBr, cm$^{-1}$) 1693, 1627, 1594, 1568, 1521, 1490, 1444, 1356, 1284, 1267, 1228, 1187, 1154, 1123, 1083, 1022, 981, 967, 930, 852, 813, 784, 769, 736, 713, 697, 665, 624, 592, 535, 458.

2' Carboxy-5-chloro-2,4-dihydroxybenzophenone $AlCl_3$ (40.0 g, 300 mmol) was added to a solution of phthalic anhydride (20.0 g, 135 mmol) and 4-chlororesorcinol (18.8 g, 130 mmol) in 225 ml nitrobenzene and purged with $N_2$. After stirring overnight, the solution was poured into a vigorously stirred biphasic solution of 750 ml hexanes and 1.0 L 0.5 M aqueous HCl. The solution was allowed to stir for 2 h and the light tan precipitate that formed was filtered and washed with 200 ml aqueous 0.1 M HCl and 300 ml hexanes. The crude product was crystallized from hot MeOH/$H_2O$ (12.1 g, 32%). $^1$H NMR (CD$_3$OD) δ 6.48 (1 H, s), 6.95 (1 H, s), 7.39 (1 H, dd, J=7.2 1.5), 7.62-7.52 (2 H, m), 8.12 (1 H, dd, J=1.2, 7.8). FTIR (KBr, cm$^{-1}$) 1691, 1615, 1571, 1488, 1453, 1419, 1288, 1219, 1155, 1141, 925, 894, 862, 772, 738, 709, 682, 649, 615, 590, 538.

7'-Chloro-4'-methylfluorescein dibenzoate

2'-Carboxy-5-chloro-2,4-dihydroxybenzophenone (10.00 g, 34.1 mmol), 2-methylresorcinol (4.25 g, 34.1 mmol), and $ZnCl_2$ (0.90 g, 6.6 mmol) were ground and melted at 200° C. As the liquid was heated for 50 minutes, it turned into a brick red solid. The solid was cooled to room temperature, ground into a powder and boiled in 200 ml 6 M aqueous HCl for 30 min. The dark red solid was then filtered, washed with deionized water, and dried. The crude 7'-chloro-4'-methylfluorescein was dissolved in 125 ml pyridine and benzoic anhydride (30.5 g, 135 mmol) was added. After refluxing for 2.5 h, the orange solution was poured into 250 ml deionized water. Upon cooling a light brown solid formed. The solid was filtered, dissolved in boiling toluene, filtered through activated charcoal, washed with 200 ml hot toluene, and dried. The solid was crystallized from hot toluene/EtOH (10.50 g, 52%). $^1$H NMR (CD$_2$Cl$_2$) δ 2.37 (3 H, s), 6.74 (1 H, d, J=8.7 Hz), 6.94 (1 H, d, J=8.7 Hz), 7.00 (1 H, s), 7.30 (1 H, d, J=7.5), 7.53-7.59 (4 H, m), 7.67-7.80 (4 H, m), 8.06 (1 H, d, J=7.5 Hz), 8.20-8.24 (4 H, m). FTIR (KBr, cm$^{-1}$) 1771, 1747, 1600, 1580, 1482, 1466, 1451, 1439, 1409, 1265, 1242, 1217, 1180, 1157, 1081, 1062, 1022, 710, 693.

7'-Chloro-4'-bromomethylfluorescein dibenzoate 1,1'-Azobis(cyclohexanecarbonitrile) (415 mg, 1.7 mmol) was added to a solution of 7'-chloro-4'-methylfluorescein (10.00 g, 17.0 mmol), 1,3-dibromo-5,5-dimethylhydantoin (4.86 g, 17.0 mmol),$^1$HOAc (300 μl, 5.3 mmol) in 400 ml chlorobenzene. The light yellow solution was heated at 40° C. for 50 hours and the solvent was removed by rotary evaporation. Light orange crystals of 7'-chloro-4'-bromomethylfluorescein dibenzoate were obtained by crystallization from hot toluene/EtOH (10.72 g, 94%). $^1$H NMR (CD$_3$OD) δ 4.80 (2 H, s), 6.90 (1 H, d, J=8.7 Hz), 7.02 (1 H, s), 7.08 (1 H, d, J=8.7 Hz), 7.33 (1 H, d, J=7.5 Hz), 7.51 (1 H, s), 7.54-7.61 (4 H, m), 7.69-7.80 (4 H, m), 8.07 (1 H, d, J=7.2 Hz), 8.22-8.27 (4 H, m). FTIR (KBr, cm$^{-1}$) 1771, 1746, 1600, 1580, 1482, 1466, 1451, 1439, 1409, 1265, 1242, 1217, 1180, 1157, 1081, 1062, 1022, 899, 796, 710, 693.

7'-Chloro-4'-fluoresceincarboxaldehyde

7'-Chloro-4'-bromomethylfluorescein dibenzoate (2.00 g, 3.0 mmol) and $NaHCO_3$ (2.52 g, 30 mmol) in 75 ml DMSO (freshly vacuum distilled from $CaH_2$) was heated to 150° C. for 3 h. The deep red solution was stirred for an additional 1 hr while cooling to 70° C. An orange precipitate formed as the solution was poured into 500 ml 4 M HCl. After stirring overnight, the mixture was extracted with CHCl$_3$ (4×150 ml) and the solvent was removed to leave a dark orange-brown liquid. A light yellow solid precipitated upon addition of 75 ml deionized water. Flash chromatography of the filtered and dried solid on silica gel (33:1 CHCl$_3$/MeOH) yielded a light yellow solid. The light yellow solid was dissolved in hot chlorobenzene on cooling 7'-chloro-4'-fluoresceincarboxaldehyde crystallized (207 mg, 18%). TLC silica (9:1 CHCl$_3$/MeOH) $R_f$=0.57. $^1$H NMR (CD$_2$Cl$_2$) δ 6.06 (1 H, s), 6.65 (1 H, d, J=8.7 Hz), 6.81 (1 H, s), 6.90 (1 H, d, J=8.7), 7.05 (1 H, s), 7.19 (1 H, d, J=7.2 Hz), 7.67-7.70 (2 H, m), 8.03 (1 H, d, J=6.9 Hz), 10.65 (1 H, s), 12.16 (1 H, s). FTIR (KBr, cm$^{-1}$) 1771, 1726, 1653, 1588, 1512, 1467, 1447, 1429, 1401, 1359, 1311, 1294, 1263, 1249, 1226, 1151, 1122, 1097, 1036, 1000, 892, 878, 841, 784, 772, 762, 727, 703, 646, 625, 543, 532, 486.

2'-chloro-5'-methyl-fluoroscein di-t-butyldimethylsilyl ether

Imidazole (0.58 g, 8.5 mmol) and 2'-chloro-5'-methyfluoroscein (1 gm, 2.6 mmol) were combined in DMF (200 ml) and stirred to form a red slurry. t-Butyldimethylsilyl chloride (1.19 g, 7.9 mmol) was added to the reaction, and the mixture was stirred for 12 h at room temperature. All but 50 ml of the DMF was removed, and the remaining solution was diluted with saturated brine (approx. 200 ml). The aqueous layer was extracted twice with EtOAc, and the two organic portions were combined and washed with brine. The organic portion was dried over magnesium sulfate, filtered, and the solvents removed to give a brown oil. The oil was filtered through a plug of silica gel and the solvents removed. Flash chromatography (9:1 hexanes/EtOAc0 yielded a yellow oil (0.3 g, 20%).

2'-Chloro-5'-bromomethylfluoroscein di-t-butyldimethylsilyl ether

2'-chloro-5'-methyl-fluoroscein di-t-butyldimethylsilyl ether (0.3 g, 0.49 mmol), 1,3-dibromo-5,5-dimethylhydantoin (0.16 g, 0.55 mmol), and 1,1'-azobis(cyclohexanecarbonitrile) (VAZO 88, 6.6 mg, 27 umol) were combined in $C_6H_5Cl$ (100 ml) and stirred. One drop acetic acid was added to the solution and the reaction was stirred at 40° C. for 60 h. The crude reaction was washed twice with hot water (100 ml, 80° C.) and the solvent removed. Flash chromatography on silica (7:1 hexanes/EtOAc) yielded a brown oil (0.15 g, 44%).

3-Bromomethyl-1-fluoro-4-nitro-benzene

5-Fluoro-2-nitrotoluene (9.3 g, 60 mmol), 1,3-dibromo-5,5-dimethylhydantoin (20 g, 70 mmol), and 1,1'-azobis(cyclohexanecarbonitrile) (VAZO 88, 600 mg, 2.5 mmol) were combined in $C_6H_5Cl$ (600 ml) and stirred. Acetic acid (300 ul, 5.24 mmol) was added to the solution and the solution was stirred at 40° C. for 96 h. The crude reaction mixture was washed three times with hot $NaHCO_3$ solution (200 ml, 80° C.), dried over magnesium sulfate, filtered and the solvent removed. The resulting crude red-orange solid was filtered through silica to yield a mixture that was about 1:1 brominated product and unbrominated starting material. The material was carried onto the next step without further purification. Pure material could be obtained from flash chromatography on silica (6:1 hexanes/EtOAc) to give a brown oil (3.84 g, 27%).

1-Fluoro-4-nitro-3-[bis(2-pyridylmethyl)aminoethyl]-benzene

3-Bromomethyl-1-fluoro-4-nitro-benzene (7 g, 34 mmol, from a 13.9 g mixture with 5-fluoro-2-nitrotoluene from the previous reaction), DPA (7.38 g, 36 mmol), $K_2CO_3$ (48.5 g, 351 mmol), and powdered 3 angstrom molecular sieves (4 g) were combined in 250 ml acetonitrile and stirred for 12 h. The crude reaction was filtered through celite and the solvent removed. The resulting brown oil was purified by flash chromatography on basic alumina with a solvent gradient ($CH_2Cl_2$:EtOAc 9:14→4:1→7:3), which yielded an orange oil (4.8 g, 40%).

4-Amino-1-fluoro-3[bis(2-pyridylmethyl)aminomethyl]-benzene

1-Fluoro-4-nitro-3-[bis(2-pyridylmethyl)aminoethyl]-benzene (1 g, 3 mmol) and Pd/C (2 g, 10% activated) were combined in methanol (200 ml) and stirred under hydrogen (1 atm) for 12 h. The crude reaction mixture was filtered through celite and the solvent removed. Flash chromatography on basic alumina with a solvent gradient ($CH_2Cl_2$:EtOAc 4:1→7:2:1 $CH_2Cl_2$:EtOAc:MeOH) yielded the product as a yellow oil (0.34 g, 37%).

2-[5-({2-[(Bis-pyridin-2-ylmethyl-amino)-methyl]-4-fluoro-phenylimino}-methyl)-2-chloro-6-hydroxy-3-oxo-9,9a-dihydro-3H-xanthen-9-yl]-benzoic acid (9, Zinpyr-5 Imine)

2'-Chloro-5'-fluoresceincarboxaldehyde (93 mg, 240 μmol) and 4-amino-1-fluoro-3[bis(2-pyridylmethyl)aminomethyl]-benzene (70 mg, 22 μmol) were combined in 6 mL of EtOAc and the resulting pink solution was stirred for 20 h at rt. Initial formation of a pink precipitate was observed after approximately 1 h. The reaction was filtered through a frit and the precipitate was washed with cold EtOAc, dissolved in 1:1 $CHCl_3$:MeOH and washed off the frit. The solvent was removed and product was used without further purification. (85 mg, 56%). $^1$H NMR ($CD_3OD$, 400 MHz) δ 3.88 (4H, s), 3.96 (2H, d), 6.66 (1H, s), 6.69 (1H, d), 6.80 (1H, d), 6.99 (1H, s), 7.15 (1H, t), 7.20 (2H, t), 7.34 (4H, m), 7.56 (2H, d), 7.68 (2H, td), 7.77 (1H, t), 7.83 (1H, t), 7.91 (1H, s), 8.08 (1H, d), 8.36 (2H, d), 9.25 (1H, s). $^{13}$C NMR (DMF-$d_{10}$, 400 MHz) δ 54.77, 60.75, 83.15, 105.479, 108.35, 109.99, 112.33, 115.04, 118.30, 123.32, 124.07, 125.38, 126.05, 127.76, 129.60, 131.62, 134.25, 136.93, 137.51, 150.08, 151.35, 152.22, 153.37, 156.91, 159.31, 160.18, 162.85, 165.12, 169.74. $^{19}$F NMR (DMF-$d_{10}$, 300 MHz) δ 56.30. FTIR (KBr, cm$^{-1}$) 3420, 305, 2920, 2849, 1763, 1634, 1594, 1481, 1359, 1271, 1224, 1178, 1151, 1106, 1037, 998, 871, 800, 761, 732, 613, 546, 487. HRMS (ESI) calcd MH$^+$, 699.1805; found, 699.1807.

2-[5-({2-[(Bis-pyridin-2-ylmethyl-amino)-methyl]-4-fluoro-phenylamino}-methyl)-2-chloro-6-hydroxy-3-oxo-9,9a-dihydro-3H-xanthen-9-yl]-benzoic acid (11, Zinpyr-5)

Zinpyr-5 imine (85 mg, 123 μmol) was dissolved in 10 mL of DCE, NaB(OAc)$_3$H (39 mg, 184 μmol) was added, and the reaction was stirred for 2.5 h. Over the course of 30 min the reaction evolved from cloudy yellow-orange to cloudy red-orange, and the reaction became clear after approximately 1 h. The reaction was quenched with 10 mL of saturated brine and the brine was extracted with $CHCl_3$ (3×10 mL). The combined organic layers were dried over $MgSO_4$, and the solvent was removed to yield a pink solid. $^1$H NMR of the crude material shows >90% purity. Low-pressure reverse phase chromatography (65:35 MeOH:0.1 N HCl) followed by solvent removal generated the HCl salt of Zinpyr-5. To obtain the free dye, the HCl salt was loaded onto a second RP column (100% $H_2O$) and was thoroughly washed with $H_2O$ until neutral pH was achieved. The product was flushed off the column (100% MeOH) and a portion of solvent was removed. The remaining solution was taken up in $H_2O$, washed with hexanes and dried to yield Zinpyr-5 as a red-pink solid (26 mg, 30%). $^1$H NMR (DMF-$d_{10}$) δ 3.80 (6H, m), 4.60 (2H, s), 6.86 (2H, s), 6.93 (1H, d), 6.96 (3H, m), 7.17 (3H, m), 7.45 (3H, t), 7.54 (2H, t), 7.83 (1H, t), 7.89 (1H, t), 8.02 (1H, s), 8.09 (1H, d), 8.38 (2H, d). $^{13}$C NMR (DMF-$d_{10}$) δ 57.50, 60.39, 83.51, 104.76, 110.72, 111.91, 113.01, 113.51, 116.99, 122.57, 123.62, 124.71, 125.24, 127.35, 128.19, 128.86, 130.84, 136.15, 136.92, 145.57, 149.37, 151.61, 152.81, 156.01, 159.08, 169.17. $^{19}$F NMR (DMF-$d_{10}$) δ 45.43. FTIR (KBr, cm$^{-1}$) 3422, 1664, 1574, 1508, 1460, 1375, 1342, 1307, 1222, 1153, 1009, 939, 886, 835, 765, 716, 630, 598, 549, 468. HRMS (ESI) calcd MH$^+$, 701.1962; found, 701.1963.

2-Nitro-5-chloro-benzylbromide

2-Nitro-5-chlorotoluene (6.0 g, 35.0 mmol), 1,3-dibromo-5,5-dimethyl hydantoin (10.6 g, 37.1 mmol), and 1,1-azobis-(cyclohexanecarbonitrile) (VAZO 88, 400 mg, 16 μmol) were combined in 275 mL of $C_6H_5Cl$ and stirred. Glacial acetic acid (200 μL) was added and the reaction was heated to 40° C. for 120 h. The reaction was washed with 150 mL of warm saturated bicarbonate, extracted with warm bicarbonate (4×150 mL) and washed with water (150 mL). The organic layer was dried over $MgSO_4$ and the solvent was removed to yield a pink-red oily solid that consists of 2-nitro-5-chlorotoluene (~40%) and the desired product (~60%) and can be carried on to the next reaction without further purification. Flash chromatography on silica gel (25:1 hexanes:EtOAc) yields the pure brominated product as a brown solid (38%). $^1$H NMR ($CDCl_3$, 300 MHz) δ 8.0 (1H, dd), 7.56 (1H, d), 7.45 (1H, dd), 4.79 (2H, s). $^{13}$C NMR ($CDCl_3$, 300 MHz) δ 28.43, 127.02, 129.61, 132.37, 134.64, 139.91, 145.96. FTIR (KBr, cm$^{-1}$) 1604, 1569, 1522, 1474, 1443, 1338, 1306, 1227, 1202, 1109, 1064, 908, 827, 757, 706.93, 827, 757, 707, 685, 524. HRMS (EI) calcd M$^+$, 248.9187; found, 248.9186.

2-Nitro-5-chloro-1-[bis(2-pyridylmethyl)aminomethyl]-benzene

2-Nitro-5-chloro-benzylbromide (~3.5 g, ~14.0 mmol; from a 9.3 g mixture containing ~40% 2-ntiro-5-chlorotoluene), di-(2-picolyl)amine (DPA, 3.32 g, 16.0 mmol), $K_2CO_3$ (2.6 g, 19 mmol), and molecular sieves (3.5 g) were combined in 100 mL of $CH_3CN$ and the resulting brown solution was stirred at rt for 24 h. The reaction was filtered through Celite and rotavaped to yield an impure brown oil. Flash chromatography on basic $Al_2O_3$ using gradient elution ($CH_2Cl_2$:EtOAc 9:1→4:1→1:1) yields the product as a brown solid (5.75 g, 64% based on the assumed composition of the starting mixture). $^1$H NMR ($CDCl_3$, 300 MHz) δ 3.65 (4H, s), 3.92 (2H, s), 6.94 (2H, m), 7.07 (1H, dd), 7.20 (2H, d), 7.44 (2H, t), 7.56 (2H, t), 8.28 (2H, d). $^{13}$C NMR ($CDCl_3$, 300 MHz) δ 55.22, 60.27, 121.89, 122.91, 125.48, 127.47, 130.76, 136.06, 136.67, 138.37, 147.49, 148.59, 157.83. FTIR (KBr, cm$^{-1}$) 1604, 1589, 1565, 1515, 1474, 1448, 1429, 1363, 1333, 1299, 773, 761, 747. HRMS (ESI) calcd MH$^+$, 369.1113; found, 369.1115.

2-Amino-5-chloro-1-[bis(2-pyridylmethyl)aminomethyl]-benzene

Pd on carbon (10% wt, 1.01 g) was placed in a 100 mL flask purged with Ar and 40 mL of MeOH was added. 2-Nitro-5- chloro-1-[bis(2-pyridylmethyl)aminomethyl]-benzene (569 mg, 1.55 mmol) was dissolved in 10 mL of MeOH and added to the reaction flask with a syringe. A balloon with $H_2$ was attached and the reaction was left to stir vigorously under $H_2$ for 1 h at rt. The reaction was purged with Ar, filtered through Celite and dried to yield a brown solid (380 mg, 72%) that was used without further purification. The product can be purified by flash chromatography on basic $Al_2O_3$ (20:4:2.5 $CH_2Cl_2$:EtOAc:isopropylamine) to give a brown solid (65%). $^1H$ NMR ($CDCl_3$, 300 MHz) δ 3.59 (2H, s), 3.80 (4H, s), 6.52 (1H, d), 7.00 (2H, m), 7.11 (2H, m), 7.38 (2H, t), 7.60 (2H, 5), 8.55 (2H, d). $^{13}C$ NMR ($CDCl_3$, 300 MHz) δ 57.18, 58.71, 116.62, 121.28, 121.98, 123.20, 123.67, 127.91, 130.29, 136.39, 144.94, 148.64, 158.22. HRMS (ESI) calcd $MH^+$, 339.1371; found, 339.1383.

2-[5-({2-[(Bis-pyridin-2-ylmethyl-amino)-methyl]-4-chloro-phenylamino}-methyl)-2-chloro-6-hydroxy-3-oxo-9,9a-dihydro-3H-xanthen-9-yl]-benzoic acid (10, Zinpyr-6 Imine)

2-Amino-5-chloro-1-[bis(2-pyridylmethyl)aminomethyl]-benzene (66 mg, 195 μmol) and 2'-chloro-5'-fluoresceincarboxaldehyde (77 mg, 195 μmol) were combined in 7 mL of EtOAc and stirred at rt to yield a cloudy orange-pink solution. A yellow precipitate formed over the course of 12 h. The reaction was filtered through a frit and the precipitate was washed with cold EtOAc, dissolved in 1:1 $CH_2Cl_2$:MeOH, washed off the frit, and the solvent was evaporated to afford a pink solid that was used without further purification (67 mg, 48%). $^1H$ NMR (DMF-$d_{10}$, 400 MHz) δ 3.10 (4H, s), 3.98 (2H, s), 6.80 (1H, m), 6.92 (3H, m), 7.24 (2H, m), 7.29 (1H, s), 7.50 (5H, m), 7.74 (2H, t), 7.86 (2H, m), 8.10 (1H, d), 8.50 (2H, d), 9.48 (1H, s). $^{13}C$NMR (DMF-$d_{10}$, 400 MHz) δ 54.37, 60.35, 82.00, 105.06, 107.94, 109.62, 114.63, 121.78, 122.78, 123.61, 124.91, 125.60, 128.83, 129.11, 130.23, 131.15, 132.44, 133.94, 135.82, 136.45, 137.00, 159.75, 159.95, 162.98, 169.24. FTIR (KBr, $cm^{-1}$) 3432, 3055, 2920, 2849, 1764, 1632, 1613, 1590, 1478, 1433, 1359, 1264, 1225, 1177, 1150, 1090, 1105, 1036, 1013, 871, 799, 762. HRMS (ESI) calcd $MH^+$, 715.1510; found, 715.1532.

2-[5-({2-[(Bis-pyridin-2-ylmethyl-amino)-methyl]-4-chloro-phenylamino}-methyl)-2-chloro-6-hydroxy-3-oxo-9,9a-dihydro-3H-xanthen-9-yl]-benzoic acid (12, Zinpyr-6)

Zinpyr-6 imine (67 mg, 95 μmol) was dissolved in 10 mL of DCE and stirred. $NaB(OAc)_3H$ (25 mg, 118 μmol) was added and the reaction was left to stir at rt. The cloudy orange solution became clear over the course of 5 h. The reaction was washed with 10 mL of saturated brine and the brine was extracted with $CHCl_3$ (3×10 mL). The combined organic layers were dried over $MgSO_4$ and the solvent was removed to give Zinpyr-6 as an orange solid (61 mg, 90%). The crude material is ~90% pure. An analytically pure sample was obtained by dissolving ~7 mg of the crude product in 300 μL DMF and adding 1:1 MeOH : 0.1% TFA (3 mL), which resulted in the immediate precipitation of Zinpyr-6 as an orange solid. $^1H$ NMR (DMF-$d_{10}$, 300 MHz) δ 3.75 (6H, m), 4.61 (2H, s), 6.73 (1H, d), 6.85 (1H, s), 6.92 (1H, d), 7.04 (1H, d), 7.20 (4H, m), 7.43 (2H, t), 7.56 (2H, t), 7.88 (2H, dt), 8.10 (1H, d), 8.38 (2H, dd). HRMS (ESI) calcd M–H, 715.1510; found, 715.1526.

General Spectroscopic Methods. PIPES (piperazine-N,N'-bis(2-ethanesulfonic acid) from Calbiochem, KCl (99.997%), and $ZnCl_2$ (99.999%) are purchased and used as received. All experiments for this Example Eight, with the exception of the $pK_a$ experiment, are conducted under stimulated physiological conditions using 50 mM PIPES, 100 mM KCl adjusted to pH 7 via drop-wise addition of KOH. Millipore water is used for all aqueous solutions, which are filtered through a 0.2 μm cellulose filter prior to use (buffered dye solutions should not be put through the filters because the dyes will get stuck). An Orion glass electrode, which is calibrated prior to each use, is used to determine solution pH. The accuracy of each micropipette is verified prior to use. Zinc solutions are prepared from 100 mM and 10 mM stock solutions in water (pH 5). The concentrations of the stock solutions is verified by spectrophotometric titration with 2,2':6',2"-terpyridine, which is was performed a minimum of three times per solution. In a typical titration, 0.5 μL aliquots of a 10 mM (nominal) Zn(II) solution in water is added to a 10 μM solution of terpyridine in 50 mM PIPES, 100 mM KCl, pH 7 prepared from a 100 mM stock solution in DMSO. The equivalence point at 321 nm and at 291 nm is determined and used to calculate the Zn(II) concentration. Stock solutions of Zinpyr-5 (0.76 mM) and Zinpyr-6 (0.41 mM) in DMSO are prepared, stored at –25° C., and thawed in the dark immediately prior to use. All spectral data are manipulated with the KaleidaGraph software package.

UV-Visible Spectroscopy. Excitation spectra are obtained using a Cary IE scanning spectrophotometer controlled by a Pentium PC running the manufacturer supplied software program. A circulating water bath is used during all acquisitions to maintain the temperature at 25.0° C.±0.1° C. All data are collected using a 600 nm/min scan speed and a 1 nm data interval. Samples are contained in 1-cm path length quartz cuvettes (3.5 mL volume). Molar absorptivity values are determined from a minimum of three titrations over a concentration range of 10 μM to 1 μM. All other manipulations are performed in triplicate and on different days to assure the authenticity of the results.

Fluorescence Spectroscopy. Emission spectra are obtained using a Hitachi F-3010 spectrofluorimeter linked to a Pentium PC running the SpectraCalc software package. A 150 W Xe lamp (Ushio Inc.) operating at a current of 5 A provides the excitation. A rhodamine quantum counter is used to normalize the spectra for excitation intensity, and manufacturer-supplied correction curves are used to normalize the emission spectra. Manufacturer supplied photomultiplier curves are used to correct for emission intensity. A circulating water bath is used during all experiments to regulate the temperature at 25.0° C.±0.1° C. All spectra are obtained using 3 nm slit widths and a 240 nm/min scan speed, and all samples are contained in a 1 cm×1 cm quartz cuvette with a 3.5 mL volume. All measurements are made in triplicate, with the exception of the Zinpyr-6 $pK_a$ titration, and on different days to assure the authenticity of the results.

Quantum Yield Measurements. The quantum yields of Zinpyr-5 and Zinpyr-6 are determined using a solution of fluorescein in 0.1 N NaOH (φ=0.95) as a reference. In a typical experiment, a 6 mL solution of 1 μM Zinpyr is prepared. For metal-free studies, 6 μL of 100 mM $K_4EDTA$ is added to chelate any adventitious metal ions. To determine the quantum efficiencies of the metal-bound dyes, either 2 μL (Zinpyr-5) or 6 μL (Zinpyr-6) of a 100 mM $ZnCl_2$ stock solution is added to a 1 μM Zinpyr solution. The concentration of the reference solution is adjusted to match the excitation spectra of the Zinpyr dye, and the appropriate excitation wavelength is determined from where the reference and probe excitation spectra intersect. Excitation is provided at 497 nm (Zinpyr-5 and Zinpyr-6, metal-free), 491 nm (Zinpyr-5, metal-bound), or 493 (Zinpyr-6, metal-bound). Emission spectra are integrated from 450-650 nm and the quantum yields were calculated using the standard equation. Godwin, H. A.; Berg, J. M. J. Am. Chem. Soc. 1996, 118, 6514-6515.

Studies of Protonation Constants that Effect Fluorescence. The apparent protonation constants that affect fluorescence are determined by plotting the integrated emission intensity versus pH from ~12.5 to 2. In a typical experiment, a 30 mL solution of 1 µM Zinpyr in 100 mM KCl, 10 mM KOH is adjusted to pH 12.5 by drop-wise addition of KOH. Aliquots of 6 N, 2 N, 1 N, 0.5 N, 0.5 N, 0.1 N, and 0.01 N HCl are added to achieve pH changes of approximately 2.5, and the emission spectrum is gathered at each interval. The overall volume change for each experiment is monitored so as not to exceed ~3%. Excitation is provided at 498 nm for Zinpyr-5 and at 500 nm for Zinpyr-6. Data is integrated from 505 nm to 650 nm, normalized and plotted against pH. The data were fit to the non-linear expression previously described. Godwin, H. A.; Berg, J. M. J. Am. Chem. Soc. 1996, 118, 6514-6515.

Metal Ion Selectivity Measurements. The metal ion selectivity of Zinpyr-5 and Zinpyr-6 for a number of divalent first-row transition metals, in addition to cadmium, is investigated using fluorescence spectroscopy. Aqueous metal ion solutions for Ca(II), Mg(II), Mn(II), Co(II), Ni(II) and Cd(II) are prepared from the chloride salts and Millipore water. The Cu(II) solution are prepared from copper sulfate and Fe(II) solutions are prepared immediately before use with ferrous ammonium sulfate and Millipore water that was thoroughly purged with Ar. In a typical experiment, 15 µL of a ~10 mM metal solution is added to a 1 µM Zinpyr solution (3 mL) and the emission spectra is recorded with excitation at 498 nm (Zinpyr-5) or 500 nm (Zinpyr-6). A 15 mL aliquot of 10 mM $ZnCl_2$ is then added and the emission spectra is obtained. The spectra are integrated from 505-650 nm (Zinpyr-5) or 450-650 nm (Zinpyr-6) and normalized.

Zn(II) Binding Studies (Fluorescence Spectroscopy). The dissociation constants, $K_d$, for Zn(II) binding were determined using a dual-metal buffering system, which affords concentrations of free Zn(II) in the nM range. Excitation was provided at 498 nm for Zinpyr-5 and at 500 nm for Zinpyr-6. The response was quantified by integrating the emission intensity from 505-650 nm and normalizing. The plot of response versus [Zn] was fit using the standard equation, response=$\{B\times[Zn]\}/\{K_d+[Zn]\}$, where B is a normalization factor and [Zn] indicates the concentration of free Zn(II) in solution.

Zn(II) Binding Studies (Absorption Spectroscopy). Metal binding titrations and Job plots are obtained for Zinpyr-5 and Zinpyr-6 to determine the stoichiometry of the metal-bound complexes. In a typical titration, 0.5 mL aliquots of a 10 mM $ZnCl_2$ solution are added to a 3 mL solution of Zinpyr (10 µM-20 µM). The absorbance changes at 512 nm (Zinpyr 5 and Zinpyr-6), 492 nm (Zinpyr-6), 491 nm (Zinpyr-5), and 462 nm (Zinpyr-6) are recorded, normalized and plotted against the equivalents of Zn(II) in solution. For the Job analysis, a 10 µM solution of Zn(II) in 50 mM PIPES, 100 mM KCl, pH 7 is prepared from a standardized 10 mM stock solution in water and a "remove and replace" titration is performed starting with a 10 µM Zinpyr solution (3 mL). A* is calculated for a minimum of three different wavelengths according to the equation $A^* = A_{observed} - \epsilon_{Zinpyr} \times [Zinpyr]$, where Zinpyr refers to the metal-free probe, and is plotted against the mol fraction of Zn(II) in solution.

The strategy employed for assembling Zinpyr-5 and Zinpyr-6 involves condensation of 2'-chloro-5'-fluoresceincarboxaldehyde with 5 or 6 and subsequent borohydride reduction using $NaB(OAc)_3H$ as the reducing agent. See FIG. 22. The overall yield for this syntheses is less than 1%. An alternative asymmetric fluorescein starting material, 2'-chloro-5'-bromomethylfluorescein di-t-butyldimethylsilyl ether, was employed in the syntheses of related compounds. Kikuchi, M. S. et al. J. Am. Chem. Soc. 2002, 124, 10650-10651. This starting material may be obtained in significantly greater quantities because the synthesis avoids the low yielding oxidation chemistry required for generation of the fluorescein carboxaldehyde. Despite the overall low yielding fluorescein synthesis for 2'-chloro-5'-fluorescein-carboxaldehyde, its condensation with a given ligand fragment offers a route to Zinpyr ligands that does not require deprotection following combination of the fluorophore and Zn(II) binding group because loss of the benzoate protecting groups occurs during the $DMSO/NaHCO_3$ oxidation. In some respects, this simplifies the final assembly of the subject compound. It should also be noted that the crude Zinpyr dyes obtained using the 2'-chloro-5'-fluoresceincarboxaldehyde platform are ~10% more pure than those obtained using the TBS protected fluorescein.

Fluorescence Properties of Zinpyr-5 and Zinpyr-6. Under stimulated physiological conditions, Zinpyr-5 and Zinpyr-6 have quantum efficiencies of 0.29 and 0.10 and emission maxima at 520 nm and 519 nm, respectively. Upon addition of excess Zn(II), Zinpyr-5 exhibits a 1.7-fold increase and Zinpyr-6 exhibits a 3.4-fold increase in quantum efficiency, affording values of 0.48 and 0.34, respectively. Upon Zn(II) binding, the emission maxima of both dyes undergo slight blue-shifts to 517 nm (Zinpyr-5) and 515 nm (Zinpyr-6). Blue-shifts of approximately 10 nm occur for the excitation maxima. For Zinpyr-5, the excitation maxima shifts 9 nm from 504 nm ($\epsilon$=82,500 $M^{-1}$ $cm^{-1}$) to 495 nm ($\epsilon$=91,000 $M^{-1}$ $cm^{-1}$) upon binding Zn(II). Zinpyr-6 shows a comparable shift, from 506 nm ($\epsilon$=88,600 $M^{-1}$ $cm^{-1}$) to 495 nm ($\epsilon$=98,000 $M^{-1}$ $cm^{-1}$). These hypsochromatic shifts reflect a perturbation of the fluorescein π-system and thus suggest that the phenol donor group of the fluorescein coordinates Zn(II). The brightness (φ×$\epsilon$) of Zinpyr-5 increases 1.8-fold from 23,900 $M^{-1}$ $cm^{-1}$ to 43,700 $M^{-1}$ $cm^{-1}$ upon Zn(II) coordination. The brightness of Zinpyr-6 increases 3.8-fold from 8,900 $M^{-1}$ $cm^{-1}$ to 33,000 $M^{-1}$ $cm^{-1}$.

The plots illustrating the pH dependent fluorescence changes for Zinpyr-5 and Zinpyr-6 are shown in FIG. 24. The fluorescence of Zinpyr-5 is only ~50% quenched at pH 12, and maximum emission is reached around pH 8 and is maintained throughout the physiological range. Three protonation events affect the fluorescence of Zinpyr-5 and have apparent $pK_a$ values of 10.9, 9, and 4.7. The first two protonation constants correspond to enhancement of fluorescence whereas the latter is associated with fluorescence quenching and the formation of a non-fluorescent isomer. The $pK_a$ of 10.9 suggests that tertiary amine in Zinpyr-5 binds a proton at physiological pH. The $pK_a$ of 9 is assigned to the aniline nitrogen and will be discussed below. At this time, the data for the Zinpyr-6 pH profile are only preliminary. These data suggest that the fluorescence of Zinpyr-6 is effectively quenched at high pH and increases in the physiological range, reaching a maximum around pH 5. Analysis of the preliminary results indicates that three protonation events affect fluorescence with estimated values of 10, 6.4, and 4.6. Like Zinpyr-5, the low $pK_a$ value of 4.6 corresponds to fluorescence quenching whereas the latter two values are associated with fluorescence enhancement.

The fluorescence response of Zinpyr-5 and Zinpyr-6 to various divalent first-row transition metals and Cd(II) is shown in FIG. 25. Both compounds exhibit similar behavior, although the magnitudes of the intensity changes that occur upon addition of Zn(II) differ significantly. Zinpyr-5 and Zinpyr-6 are Zn(II) and Cd(II) selective, and fluorescence enhancement upon addition of Zn(II) occurs in the presence of Ca(II), Mg(II) and Mn(II). Other divalent first-row transition metals such as Fe(II), Co(II), Ni(II), and Cu(II) do not cause a fluorescence change, and fluorescence enhancement does not occur when excess Zn(II) is added to solutions of the corresponding metal-bound complexes.

The binding affinities for Zinpyr-5 and Zinpyr-6 were determined using the dual-metal buffering system previously described. In this system, the concentrations of Ca(II) and EDTA remain constant at 2 mM and 1 mM, respectively, while the total Zn(II) concentration varies from 0-1 mM, which affords solutions that contain 0.17 nM to 25 nM of free Zn(II). FIG. 26 shows the emission response from titration of Zinpyr-5 and Zinpyr-6 with the dual-metal buffering system. Zinpyr-5 exhibits a ~1.6-fold increase in integrated emission and the Zn(II) complex has an apparent $K_d$ of 0.50±0.10 nM. The integrated emission intensity for Zinpyr-6 increases 2.5- to 3-fold and analysis of the response shows that the Zn(II) complex also has an apparent $K_d$ of 0.50±0.10 nM.

Optical Spectroscopy of Zinpyr-5 and Zinpyr-6. Titrations of Zinpyr-5 and Zinpyr-6 with Zn(II) and Job analyses were performed to characterize Zn(II) complexation. The difference spectra obtained from titration of Zinpyr-5 and Zinpyr-6 with Zn(II) show comparable features. An absorption decrease at 512 nm and increases at 492 nm and 462 nm occur upon addition of Zn(II). Titrations of Zinpyr-5 and Zinpyr-6 indicate 1:1 stoichiometry in solution and the Job analyses show a break at a mol fraction of 0.5, also indicative of 1:1 binding. Titrations and Job analyses of Zinpyr-5 with Mn(II) and Cu(II) were also performed and give analogous results.

Without intending to limit the scope of the invention in any way, the remaining discussion addresses the experimental results for the Zinpyr compounds. It is expected that the Zinpyr-5 and Zinpyr-6 ligands contain one metal binding site, which incorporates four nitrogen donors and the phenol oxygen atom of the fluorescein-based fluorophore, and that they operate by a photoinduced electron transfer (PET) mechanism. The lone pair on the secondary nitrogen atom is believed to donate an electron into the excited state of the fluorophore, which quenches fluorescence in the metal-free state. Upon coordination, the nitrogen lone pair is no longer available to donate into the fluorophore excited state, and emission is observed to occur. Investigations of these fluorescein-based ligands suggest that there is a relationship between the $pK_a$ of the donor nitrogen atom and the extent of PET quenching in the unbound sensor. The synthesis of Zinpyr-5 and Zinpyr-6 was undertaken to probe the notion of systematically tuning the electronic properties of the ligand, specifically to affect the $pK_a$ of the donor nitrogen atom, and thereby influence the off/on behavior of the ligand. The strategy evoked involved systematically altering the substituent para to the donor nitrogen atom from electron-donating to electron-withdrawing, and resulted in a series of sensors where $X_{para}$=OCH$_3$, H, F, Cl.

The physical characteristics of Zinpyr-3 (para-OCH$_3$) and Zinpyr-4 (para-H) have been reported elsewhere. Zinpyr-5 and Zinpyr-6 show changes in the optical spectra similar to Zinpyr-3 and Zinpyr-4 upon binding Zn(II). All four probes exhibit a hypsochromic shift of approximately 10 nm towards shorter wavelength upon addition of Zn(II), which is likely indicative of a perturbation to the fluorescein π-system caused by the coordination of Zn(II) to the phenol donor. The difference spectra for each probe reveal that addition of Zn(II) is accompanied by decreases in absorption at 462 nm and 492 nm, and an increase at 512 nm. Both Job analyses and metal binding titrations suggest formation of a 1:1 complex for each sensor, which is intuitively pleasing given the ligand design.

The $K_d$ values for Zinpyr-4,5,6 are all in the sub-nM range. Although the $K_d$ of Zinpyr-3 was not determined since its fluorescence change is negligible upon addition of Zn(II), we can assume it binds Zn(II) with comparable affinity. Like Zinpyr-4, Zinpyr-5 and Zinpyr-6 are Zn(II) and Cd(II) selective, and the fluorescence of the Zn(II) complexes is not compromised in a background of Ca(II), Mg(II), and Mn(II). In the presence of other divalent first-row transition metals such as Fe(II), Co(II), Ni(II) and Cu(II), no fluorescence change is observed upon addition of Zn(II) for these three dyes.

Each unbound sensor has an emission maximum at ~520 nm that blue-shifts ~5 nm upon addition of Zn(II). Zinpyr-3 and Zinpyr-4 have quantum efficiencies of 0.04 and 0.05, respectively. Zinpyr-6 exhibits similar behavior, having a quantum yield of 0.10. In contrast, the quantum yield of Zinpyr-5 is significantly higher, 0.29. These variations in quantum efficiency can be correlated to the $pK_a$ values for the nitrogen atoms that participate in PET. The $pK_a$ of the aniline nitrogen in Zinpyr-4 is 7.2, indicating that it favors deprotonation at physiological pH and that its lone pair can participate in PET quenching and thereby minimize the fluorescence of the unbound dye. The preliminary pH results for Zinpyr-6 suggest similar behavior, and account for its low quantum yield in the metal-free state. The $pK_a$ of the nitrogen atom appears to be slightly lower, approximately 6.5, which is expected given the electron-withdrawing nature of the chlorine atom. In contrast, the $pK_a$ of the corresponding nitrogen atom in Zinpyr-5 is 9. This nitrogen atom is presumably protonated at pH 7, rendering it unable to donate into the excited state of the fluorophore, which arguably explains the higher quantum yield observed for Zinpyr-5 (metal-free).

The Zn(II) complexes of both Zinpyr-4 and Zinpyr-5 have quantum efficiencies of 0.34, whereas the value for bound Zinpyr-5 is significantly higher, 0.48. Whereas Zinpyr-4 shows a ~5-fold and Zinpyr-6 shows a ~3-fold increase in integrated emission in response to the dual-metal buffering system, the increase for Zinpyr-5 is only 1.6-fold. Likewise, while Zinpyr-4 shows a 6.7-fold increase and Zinpyr-6 shows a 3.7-fold increase in brightness upon Zn(II) binding, the increase for Zinpyr-5 is only 1.8-fold.

7. REFERENCES

All publications and patents mentioned herein, including those items listed below, are hereby incorporated by reference in their entirety as if each individual publication or patent was specifically and individually indicated to be incorporated by reference. In case of conflict, the present application, including any definitions herein, will control.

Frederickson et al. *J. Neurosci. Meth*. 1987, 20, 91-103; Zalewski et al. *Biochem. J*. 1993, 296, 403-408; Mahadevan et al. *Aust. J. Chem*. 1996, 49, 561-568; Budde et al. *Neuroscience* 1997, 79, 347-358; Canzoniero et al. *Neurobiology of Disease* 1997, 4, 275-279; Fahrni et al. *J. Am. Chem. Soc*. 1999, 121, 11448-11458; Nasir et al. *JBIC* 1999, 4, 775-783; Belgodere et al. *Heterocycles* 1985, 23, 349-354; Romary et al. *J. Chem. Soc (C)* 1968, 2884-2887; da Mota et al. *J. Chem. Soc. (A)* 1969, 2036-2042; Hörlein, U. *Chemische Berichte* 1954, 87, 463-472; Houser et al. *J. Am. Chem. Soc*. 1995, 117, 10745-10746; Kovacs, Z.; Sherry, A. D. *Tet. Lett*. 1995, 51, 9269-9272; Prasad et al. *J. Chem. Soc. Perkin Trans*. 1991, 3329-3332; Vallee et al. *Physiol. Rev*. 1993, 73: 79-118; Frederickson, C. *Int. Rev. Neurobiol*. 1989, 31: 145-238; Huang, E. *Proc. Natl. Acad. Sci. U.S.A*. 1997, 94: 13386-13387; Nasir, et al. *JBIC* 1999, 4: 775-783; Frederickson et al. *Biol.*

Signals 1994, 3: 127-139; Budde et al. *Neuroscience* 1997, 79: 347-358; Harrison et al. *Neuropharmacology* 1994, 33: 935-952; Choi et al. *Ann. Rev. Neurosci.* 1998, 21: 347-375; Cuajungco et al. *Neurobiology of Disease* 1997, 4: 137-169; Palmiter et al. *EMBO J.* 1995, 14: 639-649; Palmiter, et al. *EMBO J.* 1996, 15: 1784-1791; Palmiter, et al. *Proc. Natl. Acad. Sci. USA* 1996, 93: 14934-14939; Ebadi, et al. *Methods Enzymol.* 1991, 205: 363-387; Ebadi, et al. *Neurochem. Int.* 1995, 27: 1-22; Ebadi, et al. *J. Neurochem.* 1996, 66: 2121-2127; Evans, I. *J. Org. Chem.* 1959, 24: 863; Palmiter, et al. *Proc. Natl. Acad. Sci. USA* 1992, 89: 6333-6337; Pountney, et al. *FEBS Lett.* 1994, 345: 193-197; Tsuji, et al. *EMBO J.* 1992, 11: 4843-4850; Uchida, et al. *Neuron* 1991, 7: 337-347; Slomianka, L. *Neuroscience* 1992: 48, 325-352; Atar, et al. *J. Biol. Chem.* 1995, 270: 2473-2477; de Silva et al. *Chem. Rev.* 1997, 97: 1515-1566; Tsien, R. Y. *Fluorescent and Photochemical Probes of Dynamic Biochemical Signals Inside Living Cells*; Czarnik, A. W., Ed.; American Chemical Society: Washington D.C., 1993; Vol. 538, pp 130-146; Czarnik, A. W. *Curr. Biol.* 1995, 2: 423-428; Frederickson, et al. *J. Neurosci. Meth.* 1987, 20: 91-103; Walkup et al. *J. Am. Chem Soc.* 2000, 122: 5644-5645; Lakowicz, J. R. *Principles of Fluorescence Spectroscopy*; 2nd ed.; Kluwe Academic/Plenum: New York, 1999; Gruenwedel, D. W. *Inorg. Chem.* 1968, 7: 495-501; Feig et al. *Inorg. Chem.* 1996, 25: 6892-6898; McBryde, W. A. E. *Talanta* 1974, 21: 979-1004; Walkup et al. *J. Am. Chem Soc.* 2000: 122: S1-S7; Burton et al. *J. Soc. Chem. Ind. London* 1948: 67: 345; Wolf, H. U. *Experientia* 1973, 29: 241-249; Anderegg et al. *Helv. Chim. Acta* 1977, 60: 123-140; Sen, et al. *J. Indian Chem. Soc.* 1929, 6, 505; Sen, et al. *J. Indian Chem. Soc.* 1929, 6, 51; Job, A., *Ann. Chem. (Paris)* 1928, 9, 113-203; Manhadevan, I. B. et al. Aust. J. Chem. 1996, 49, 561-568; Hirano, T. et al. J. Am. Chem. Soc. 2000, 122, 12399-12400; Thompson, R. B. et al. A. Anal. Chem. 1998, 70, 1749-1754; Tompson, R. B. et al. J. Neuro. Met. 2000, 96, 35-45; Walkup, G. K. et al. J. Am. Chem. Soc. 1997, 119, 3443-3450; Walkup, G. K. et al. J. Org. Chem. 1998, 63, 6727-6731; Godwin, H. A. et al. J. Am. Chem. Soc. 1996, 118, 6514-6515; Burdette, S. C. Ph. D. Thesis, MIT, October 2002; Zlokarnik et al, *Science* 1998, 279, 84-88; Takakusa et al, *Chem. Eur. J.*, 2003, 9 (7), 1479; Packard et al, *Biophys Chem* 1997, 67, 167-76; Takakusa et al, *Anal. Chem.* 2001, 73 (5), 939-42; Mizukami et al, *FEBS Lett* 1999, 453, 356-60; Jones et al, *Anal. Biochem.* 1997, 251, 144-52; Packard et al, *PNAS*, 1996, 93, 11640-45; Valeur et al, *J. Phys. Chem.* 1992, 96, 6545-49; Sumner et al, *Analyst* 2002, 127, 11-16; Burdette, S. C. et al. Inorg. Chem. 2002, 41, 6816-6823; Kikuchi, M. S. et al. J. Am. Chem. Soc. 2002, 124, 10650-10651; Burdette, S. C. et al. J. Am. Chem. Soc. 2001, 123, 7831-7841; Walkup, G. K. et al. J. Am. Chem. Soc. 2000, 122, 5644-5645; Tanaka, M. et al. J. Org. Chem. 2001, 66, 7008-7012; U.S. Pat. Nos. 6,013,802; 6,083,758; 6,063,637; 5,986,094; 5,756,771; 4,510,251; and U.S. patent application Ser. Nos. 09/901,466, filed Jul. 9, 2001, and 10/124,742, filed Apr. 17, 2002.

8. EQUIVALENTS

The invention now being fully described, it will be apparent to one of ordinary skill in the art that many changes and modifications may be made thereto without requiring more than routine experimentation or departing from the spirit or scope of the appended claims.

While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

We claim:

1. A compound comprising a first fluorophore, a second fluorophore and a cleavable linker covalently linking the first fluorophore and the second fluorophore, wherein the fluorescence of the first and second fluorophores are substantially quenched by one another before the cleavable linker is cleaved, and wherein the first fluorophore is represented by the following structure:

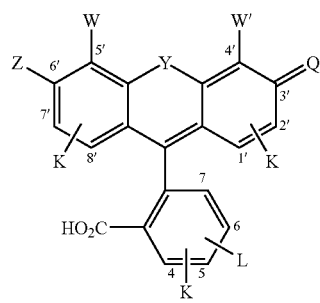

or a tautomer thereof, wherein, independently for each occurrence:
Y is O, S, Se, NR, or $C(CH_3)_2$, wherein R is an alkyl;
Q is O, S or Se;
Z is V, QH, or QU' wherein U' is a hydroxyl-protecting group;
W and W' are each independently K or V;
K is hydrogen, halogen, linear or branched alkyl, alkenyl, linear or branched aminoalkyl, linear or branched acylamino, linear or branched acyloxy, linear or branched alkoxycarbonyl, linear or branched alkoxy, linear or branched alkylaryl, linear or branched hyrdoxyalkyl, linear or branched thioalkyl, acyl, aryloxy, arylalkoxy, alkynyl, cyano, sulihydryl, carbamoyl, trifluoromethyl, lower alkylthio, lower alkylamino, nitro, amine, hydroxyl, carbonyl, formyl or sulfonyl;
L is the cleavable linker covalently bonded to either the 5 or 6 position of the indicated aromatic ring;
L comprises an ester; and
V is a chemical moiety comprising at least one Lewis base capable of coordinating to a metal ion; and
wherein one or more fluorescence properties of the first fluorophore change measurably upon coordination of said Lewis base to a metal ion.

2. The compound of claim 1, wherein Q is O and Z is OH, OU' or V.

3. The compound of claim 1, wherein V further comprises at least two Lewis bases that are together capable of forming a chelating agent upon coordination to a metal ion.

4. The compound of claim 3, wherein independently for each occurrence:
(a) when V is in W, V occurs only once in the compound or occurs only one other time in the compound in W' or Z; or
(b) when V is in W', V occurs only once in the compound or occurs only one other time in the compound in W; or
(c) when V is in Z, V occurs only once in the compound or occurs only one other time in the compound in W.

5. The compound of claim 4, wherein V occurs only once in the compound in W or W'.

6. The compound of claim 4, wherein V occurs only once in the compound in Z.

7. The compound of claim 4, wherein the Z is V, wherein V is directly bonded to the 6' carbon of the indicated aromatic ring through a nitrogen atom.

8. The compound of claim 4, wherein V occurs twice in the compound in W or W' and is the same in W and W'.

9. The compound of claim 4, wherein the Lewis bases are nitrogen atoms.

10. The compound of claim 1, wherein Q is O, Z is OH, and the atom of K directly bonded to each the 2' carbon and the 7' carbon of the indicated aromatic ring is a Cl atom.

11. The compound of claim 1, wherein said L is —C(=O)NH—(CH$_2$)$_n$—O—, wherein n is an integer from 2 to 4 inclusive.

12. The compound of claim 1, wherein said second fluorophore is represented by the following formula:

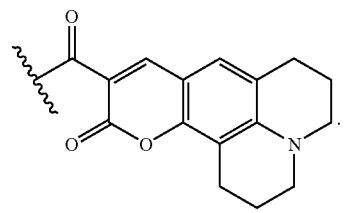

13. The compound of claim 1, wherein V is independently for each occurrence selected from the group consisting of:

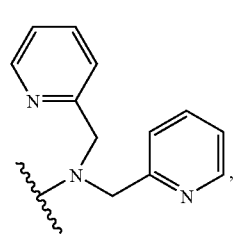
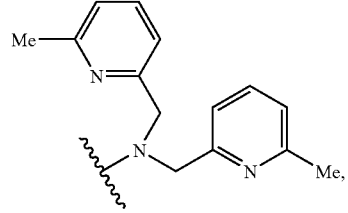

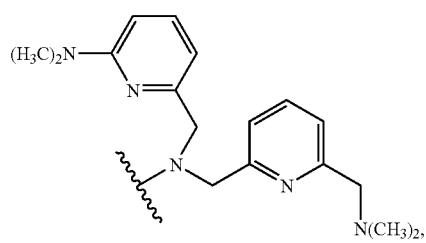

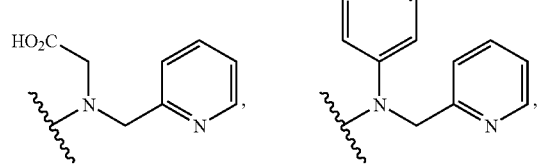

-continued

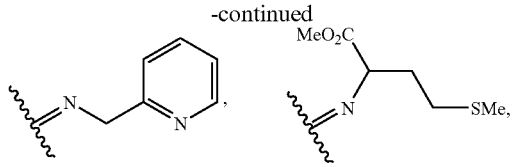

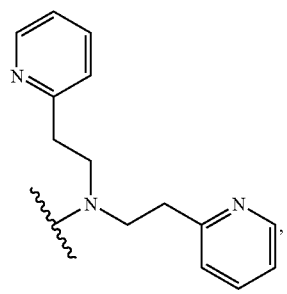

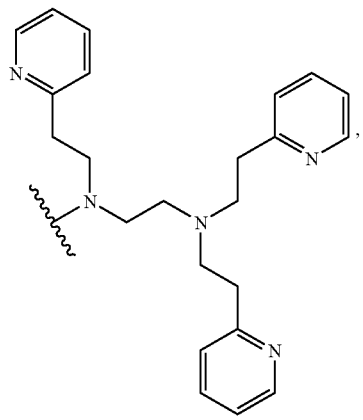

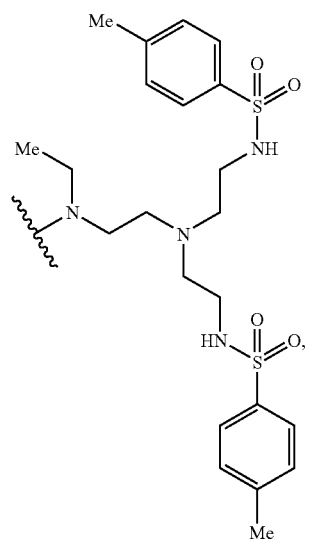

-continued
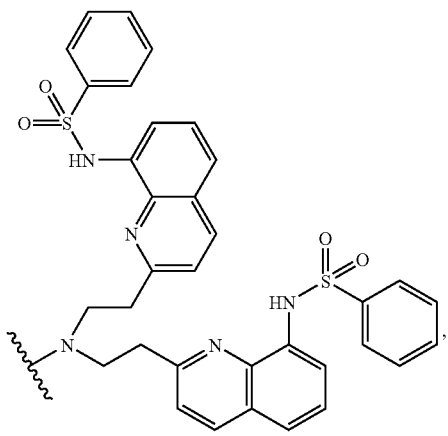
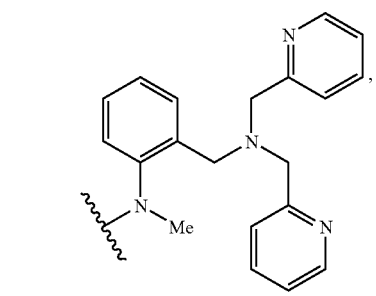
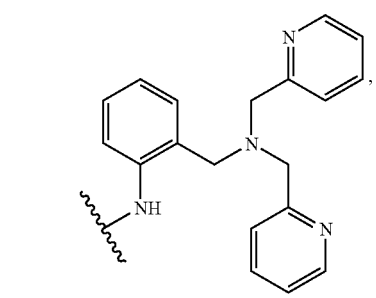
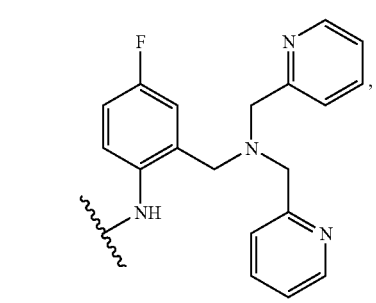
-continued
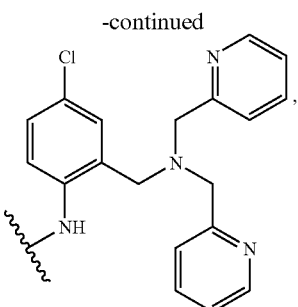
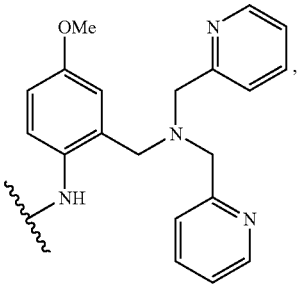
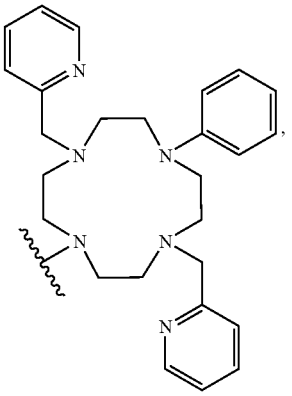
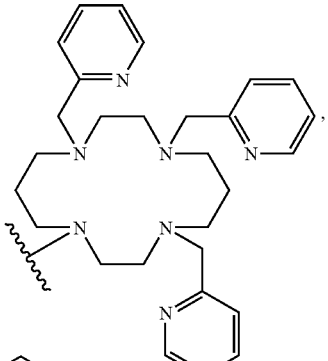
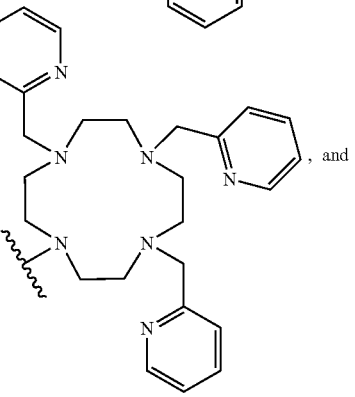, and -continued

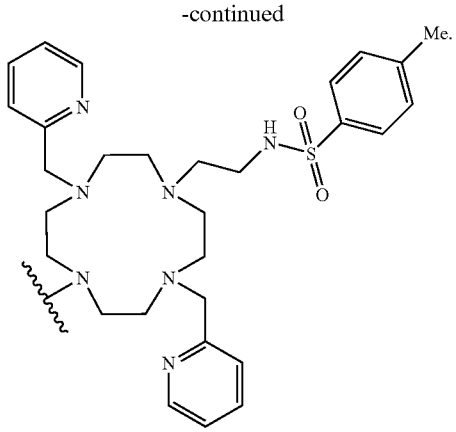

14. The compound of claim 1, wherein K is lower alkoxyl, phenoxy, or benzyloxy.

15. A compound comprising (a) a first fluorophore comprising at least one Lewis base capable of forming a coordination bond with a metal ion, wherein one or more fluorescence properties of the first fluorophore changes upon coordination of said Lewis base to a metal ion; (b) a second fluorophore; (c) a cleavable linker covalently linking the first fluorophore and the second fluorophore, wherein the cleavable linker comprises an ester and said ester is intended to be cleaved during use of the compound; and (d) the fluorescence of the first and second fluorophores are substantially quenched by one another before the cleavable linker is cleaved.

16. The compound of claim 15, wherein the first fluorophore further comprises at least two Lewis bases that are together capable of forming a chelating agent upon coordination to a metal ion.

17. The compound of claim 16, wherein the first fluorophore further comprises at least one additional Lewis base that is capable of forming a chelating agent together with the other Lewis bases upon coordination of each to a metal ion.

18. The compound of claim 16, wherein the brightness of the first fluorophore in the presence of a metal ion to which the first fluorophore is capable of coordinating is after cleavage of the cleveable linker at least twice as great as before cleavage.

19. The compound of claim 16, wherein the cleavable linker is cleavable by a naturally occurring biological activity.

20. The compound of claim 19, wherein the naturally occurring biological activity is enzymatic.

21. The compound of claim 16, wherein the first fluorophore comprises a fluorescein-based ligand.

22. The compound of claim 21, wherein the second fluorophore does not contain two nitrogen atoms that are capable of forming a chelating agent for coordination to a metal ion.

23. The compound of claim 21, wherein the binding affinity of the first fluorophore to at least one type of transition metal cation is at least two times as great as the binding affinity of the second fluorophore to the same type of metal ion.

24. The compound of claim 23, wherein the binding affinity of the first fluorophore to at least one type of transition metal cation is at least five times as great as the binding affinity of the second fluorophore to the same type of metal ion.

25. The compound of claim 24, wherein the type of metal ion is $Zn^{2+}$.

26. The compound of claim 24, wherein the first fluorophore and the second fluorophore both fluoresce at about 450 nm or above.

27. A method of detecting, and optionally quantifying the concentration of, a metal ion in a sample or a patient, comprising:
   (a) adding to a sample or administering to a patient a compound of any one of claims 1-9, 15-20, 21-26, 10, 11, 12, 13, or 14;
   (b) measuring fluorescence of the first fluorophore of the compound in the sample or the patient after cleavage of the cleavable linker has occurred for at least some measurable portion of the compound added to the sample or administered to the patient; and
   (c) determining whether the metal ion is present in the sample or patient, and optionally the concentration of the metal ion in the sample or patient.

28. The method of claim 27, further comprising measuring fluorescence of the second fluorophore of the compound in the sample or the patient after cleavage of the cleavable linker has occurred for at least some measurable portion of the compound added to the sample or administered to the patient.

29. The method of claim 28, further comprising before measuring the fluorescence of the first and second fluorophore, causing the cleavable linker to cleave for at least some measurable portion of the compound added or administered.

30. The method of claim 28, wherein the concentration of the metal ion is determined.

31. The method of claim 28, wherein the compound is added to a sample and the sample comprises cells.

32. A diagnostic kit for a metal ion, comprising:
   (a) a compound of any one of claims 1-9, 15-20, 21-26, 10, 11, 12, 13, or 14; and
   (b) instructions for using the compound to detect a metal ion in a sample or a patient.

* * * * *

UNITED STATES PATENT AND TRADEMARK OFFICE
CERTIFICATE OF CORRECTION

PATENT NO. : 7,399,639 B2
APPLICATION NO. : 10/429898
DATED : July 15, 2008
INVENTOR(S) : Stephen J. Lippard et al.

It is certified that error appears in the above-identified patent and that said Letters Patent is hereby corrected as shown below:

In column 1, lines 6-8, replace:

"The subject invention was made in part with support from the U.S. Government. Accordingly, the U.S. Government has certain rights in this invention."

with

--This invention was made with government support under grant number R01 GM065519 awarded by the National Institutes of Health. The government has certain rights in this invention.--

Signed and Sealed this
Twelfth Day of July, 2011

David J. Kappos
*Director of the United States Patent and Trademark Office*